US011364253B2

(12) United States Patent
Acharya et al.

(10) Patent No.: US 11,364,253 B2
(45) Date of Patent: *Jun. 21, 2022

(54) IMMUNODULATING SMALL MOLECULES

(71) Applicant: AyuVis Research, Inc., Fort Worth, TX (US)

(72) Inventors: Suchismita Acharya, Euless, TX (US); Pragnya Das, Secane, PA (US); Beamon Agarwal, Secane, PA (US)

(73) Assignee: AYUVIS RESEARCH, INC., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/460,211

(22) Filed: Jul. 2, 2019

(65) Prior Publication Data
US 2020/0022995 A1 Jan. 23, 2020

Related U.S. Application Data

(60) Provisional application No. 62/693,023, filed on Jul. 2, 2018.

(51) Int. Cl.
| | |
|---|---|
| *A61K 31/702* | (2006.01) |
| *A61K 31/7034* | (2006.01) |
| *A61K 31/7036* | (2006.01) |
| *A61K 31/7048* | (2006.01) |
| *A61K 31/7056* | (2006.01) |
| *A61K 9/00* | (2006.01) |
| *A61P 37/02* | (2006.01) |

(52) U.S. Cl.
CPC .......... *A61K 31/702* (2013.01); *A61K 9/0043* (2013.01); *A61K 9/0073* (2013.01); *A61K 31/7034* (2013.01); *A61K 31/7036* (2013.01); *A61K 31/7048* (2013.01); *A61K 31/7056* (2013.01); *A61P 37/02* (2018.01)

(58) Field of Classification Search
None
See application file for complete search history.

(56) References Cited

U.S. PATENT DOCUMENTS

| | | | | |
|---|---|---|---|---|
| 4,404,365 A | * | 9/1983 | Miner .................. | C07H 15/203 536/118 |
| 5,736,522 A | * | 4/1998 | Watanabe ............ | C07H 17/075 514/25 |
| 2002/0031524 A1 | | 3/2002 | Kralovec | |
| 2008/0014281 A1 | | 1/2008 | Shibata et al. | |
| 2017/0281667 A1 | | 10/2017 | Acharya et al. | |

OTHER PUBLICATIONS

Villar, J. et al. "Current incidence and outcome of the acute respiratory distress syndrome." Current opinion in critical care 2016, 22, 1-6.
Williams, J. et al. "Nanoparticle drug delivery system for intravenous delivery of topoisomerase inhibitors." Journal of Controlled Release 2003, 91, 167-172.
Wynn, J. L. et al. "Defective innate immunity predisposes murine neonates to poor sepsis outcome but is reversed by TLR agonists." Blood 2008, 112, 1750-8.
Xia, W. et al. "Biological activities of chitosan and chitooligosaccharides." Food Hydrocolloids 2011, 25, 170-179.
Yao, L. et al. "Vitamin D attenuates hyperoxia-induced lung injury through down regulation of Toll-like receptor 4." Int J Mol Med 2017, 39, 1403-1408.
Adanitsch, F. et al. "Synthetic glycan-based TLR4 agonists targeting caspase-4/11 for the development of adjuvants and immunotherapeutics." Chemical Science 2018, 9, 3957-3963.
Balany, J. et al. "Understanding the Impact of Infection, Inflammation, and Their Persistence in the Pathogenesis of Bronchopulmonary Dysplasia." Front Med (Lausanne) 2015, 2, 90.
Bhandari, A. et al. "Biomarkers in bronchopulmonary dysplasia." Paediatr Respir Rev 2013, 14, 173-9.
Bhandari, A. et al. "Long-term pulmonary outcomes of patients with bronchopulmonary dysplasia." Semin Perinatol 2013, 37, 132-7.
Bhandari, A. et al. "Pitfalls, problems, and progress in bronchopulmonary dysplasia." Pediatrics 2009, 123, 1562-73.
Bhandari, V. "Postnatal inflammation in the pathogenesis of bronchopulmonary dysplasia. Birth defects research. Part A", Clinical and molecular teratology 2014, 100, 189-201.

(Continued)

*Primary Examiner* — Traviss C McIntosh, III
(74) *Attorney, Agent, or Firm* — Edwin S. Flores; Daniel J. Chalker; Chalker Flores, LLP

(57) ABSTRACT

The present invention includes novel compositions and methods for treating comprising a compound with the Formula I:

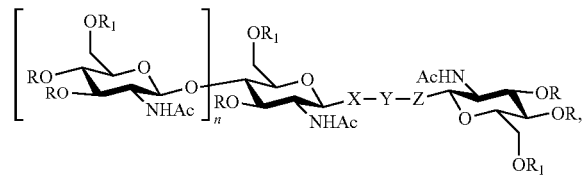

Formula-I where n=0-5; X=NH, O, S, $CH_2$; Y=Phenyl, a phenyl group substituted with at least one methyl, a phenyl group substituted with at least one nitro, a phenyl group substituted with at least one nitrogen, a phenyl group substituted with at least one boron, aryl, substituted aryl, heteroaryl, four to six membered cycloalkyl, four to six membered heterocycloalkyl; R=H, $C(O)R_2$, $SO_2R_2$; $R_1$=H, $C(O)R_2$, $SO_2R_2$; $R_2$=Ethyl, methyl, isopropyl, n-propyl, t-butyl, n-butyl, $NH_2$, $NR_3R_4$, $R_3$, $R_4$=Ethyl, methyl, isopropyl, n-propyl, t-butyl, n-butyl, three to six membered cycloalkyl and Z=NH, O, S, $CH_2$ or none, wherein the amount of the compound is selected to either inhibit or activate the immune response.

64 Claims, 19 Drawing Sheets

(56) References Cited

OTHER PUBLICATIONS

Bhandari, V. et al. "Developmental regulation of NO-mediated VEGF-induced effects in the lung." Am J Respir Cell Mol Biol 2008, 39, 420-30.
Bhandari, V., "Drug therapy trials for the prevention of bronchopulmonary dysplasia: current and future targets." Front Pediatr 2014, 2, 76.
Bhandari, V., "Molecular mechanisms of hyperoxia-induced acute lung injury." Frontiers in bioscience : a journal and virtual library 2008, 13, 6653-61.
Cavaillon, J. M. et al. "Endotoxin tolerance: is there a clinical relevance?" Journal of endotoxin research 2003, 9, 101-7.
Choo-Wing R, S. M. et al. "Hyperoxia and interferon-γ-induced injury in developing lungs occur via cyclooxygenase-2 and the endoplasmic reticulum stress-dependent pathway" Am J Respir Cell Mol Biol 2013, 48, 749-757.
Cross, A. S. "Endotoxin tolerance-current concepts in historical perspective." Journal of endotoxin research 2002, 8, 83-98.
Densmore, J. C. et al. "Endothelium-derived microparticles induce endothelial dysfunction and acute lung injury." Shock 2006, 26, 464-71.
Jensen, E. A. et al. "Epidemiology of bronchopulmonary dysplasia. Birth defects research." Part A, Clinical and molecular teratology 2014, 100, 145-57.
Kapur, R. et al. "Low levels of interleukin-10 in patients with transfusion-related acute lung injury." Annals of Translational Medicine 2017, 5, 339.
Kim, H. M. et al. "Crystal Structure of the TLR4-MD 2 Complex with Bound Endotoxin Antagonist Eritoran." Cell 2007, 130, 906-917.
Lee, H.-S. et al. "Effect of recombinant IL-10 on cultured fetal rat alveolar type II cells exposed to 65%-hyperoxia." Respiratory Research 2011, 12, 68-68.
Li, H. D. et al. "Exogenous interleukin-10 attenuates hyperoxia-induced acute lung injury in mice." Experimental physiology 2015, 100, 331-40.
Li, N. et al. "Liposome coated with low molecular weight chitosan and its potential use in ocular drug delivery." International Journal of Pharmaceutics 2009, 379, 131-138.
Li, Z.; Choo-Wing, R. et al. "A potential role of the JNK pathway in hyperoxia-induced cell death, myofibroblast transdifferentiation and TGF-beta1-mediated injury in the developing murine lung." BMC Cell Biol 2011, 12, 54.
Luster, A. D. "The role of chemokines in linking innate and adaptive immunity." Current Opinion in Immunology 2002, 14, 129-135.
McEvoy, C. T. et al. "Bronchopulmonary dysplasia: NHLBI Workshop on the Primary Prevention of Chronic Lung Diseases." Annals of the American Thoracic Society 2014, 11 Suppl 3, S146-53.
Menden, H. L. et al. "Nicotinamide Adenine Dinucleotide Phosphate Oxidase 2 Regulates LPS-lnduced Inflammation and Alveolar Remodeling in the Developing Lung." Am J Respir Cell Mol Biol 2016, 55, 767-778.
Metlitskikh et al. 'Synthesis of bis(glycosylamino)alkanes and bis(glycosylamino)arenes', Russian Chemical Bulletin, Dec. 2005, vol. 54, pp. 2890-2898; p. 2891.
Minami, S. et al. "Chitin and chitosan activate complement via the alternative pathway." Carbohydrate Polymers 1998, 36, 151-155.
Moore, K. W. et al. "Evolving principles in immunopathology: interleukin 10 and its relationship to Epstein-Barr virus protein BCRF1." Springer seminars in immunopathology 1991, 13, 157-66.
Murphey, E. D. et al. "Endotoxin pretreatment improves bacterial clearance and decreases mortality in mice challenged with *Staphylococcus aureus*." Shock (Augusta, Ga.) 2008, 29, 512-8.
Natarajan, G. et al. "Outcomes of extremely low birth weight infants with bronchopulmonary dysplasia: impact of the physiologic definition." Early Hum Dev 2012, 88, 509-15.
Naus et al. 'Copper-Assisted Arylation of 1-Thiosugars: Efficient Route to Triazene Substituted Arylthioglycosides', Synlett, Oct. 7, 2003 (Oct. 7, 2003), vol. 14, pp. 2117-2122; p. 2119.
Okawa, Y. et al. "Comparative study of protective effects of chitin, chitosan, and N-acetyl chitohexaose against Pseudomonas aeruginosa and Listeria monocytogenes infections in mice."
Panda, S. K. et al. "Chitohexaose Activates Macrophages by Alternate Pathway through TLR4 and Blocks Endotoxemia." PLoS Pathog 2012, 8, e1002717.
PCT/2019/040313 International Search Report [ISA/US] dated Dec. 3, 2019.
Qiao, Y. et al. "Chitosan oligosaccharides protect mice from LPS challenge by attenuation of inflammation and oxidative stress." International Immunopharmacology 2011, 11, 121-127.
Raju, T. N. K. et al. "Adults born preterm: a review of general health and system-specific outcomes." Acta Paediatr 2017, 106, 1409-1437.
Romero, C. D. et al. "The Toll-Like Receptor 4 Agonist Monophosphoryl Lipid A Augments Innate Host Resistance to Systemic Bacterial Infection." Infection and Immunity 2011, 79, 3576-3587.
Rubenfeld, G. D. et al. "Incidence and outcomes of acute lung injury." N Engl J Med 2005, 353, 1685-93.
Russell, R. B. et al. "Cost of hospitalization for preterm and low birth weight infants in the United States." Pediatrics 2007, 120, e1-9.
Salim, A. et al. "Acute respiratory distress syndrome in the trauma intensive care unit: Morbid but not mortal." Arch Surg 2006, 141, 655-8.
Sauerzapfe, B. et al. "Characterization of recombinant fusion constructs of human β1,4-galactosyltransferase 1 and the lipase pre-propeptide from *Staphylococcus hyicus*." Journal of Molecular Catalysis B: Enzymatic 2008, 50, 128-140.
Smith, V. C. et al. "Trends in severe bronchopulmonary dysplasia rates between 1994 and 2002." J Pediatr 2005, 146, 469-73.
Solov et al. "Compounds with Therapeutic Potential in Gram-Negative Sepsis." Marine Drugs 2013, 11, 2216-2229.
Sun H, C.-W. R. et al. "A critical regulatory role for macrophage migration inhibitory factor in hyperoxia-induced injury in the developing murine lung." PLoS ONE 2013, 8.
Sun H, C.-W. R. et al. "Small molecular modulation of macrophage migration inhibitory factor in the hyperoxia-induced mouse model of bronchopulmonary dysplasia." Respir Res 2013, 14.
Sureshbabu, A. et al. "Conditional overexpression of TGFbeta1 promotes pulmonary inflammation, apoptosis and mortality via TGFbetaR2 in the developing mouse lung." Respir Res 2015, 16, 4.
Sureshbabu, A. et al. "Inhibition of RPTOR Prevents Hyperoxia-induced Lung Injury by Enhancing Autophagy and Reducing Apoptosis in Neonatal Mice." Am J Respir Cell Mol Biol 2016.
Syed, M. A. et al. "Role of Nitric Oxide Isoforms in Vascular and Alveolar Development and Lung Injury in Vascular Endothelial Growth Factor Overexpressing Neonatal Mice Lungs." PLoS One 2016, 11, e0147588.
Thoelen, S.; Van Damme, P.; Mathei, C.; Leroux-Roels, G.; Desombere, I.; Safary, A.; Vandepapeliere, P.; Slaoui, M.; Meheus, A., Safety and immunogenicity of a hepatitis B vaccine formulated with a novel adjuvant system. Vaccine 1998, 16, 708-14.
Trembath, A. et al. "Predictors of bronchopulmonary dysplasia." Clin Perinatol 2012, 39, 585-601.

\* cited by examiner

| Compound Number | Structure | Concentration (μM) | % inhibition over control | | % activation over control | |
|---|---|---|---|---|---|---|
| | | | TLR4 | TLR2 | TLR4 | TLR2 |
| 1 | 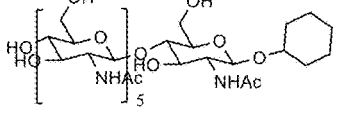 | 1-10 | +++ | | | |
| | | 75-100 | +++ | | | |
| 2 | 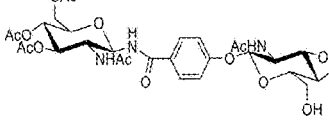 | 1 | ++ | + | | |
| | | 100 | +++ | +++ | | |
| 3 | 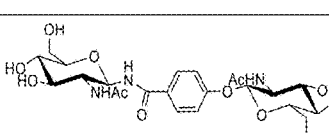 | 1 | ++ | ++ | | |
| | | 100 | +++ | +++ | | |
| 6 | 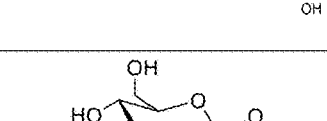 | 1 | ++ | | | |
| | | 100 | +++ | | | |
| 7 | 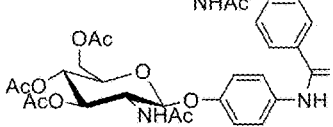 | 1 | +++ | ++ | | |
| | | 100 | +++ | +++ | | |
| 8 | 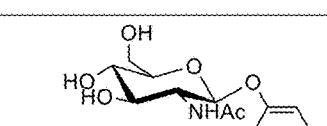 | 1 | +++ | + | | |
| | | 100 | | | ++ | ++ |
| 11 | 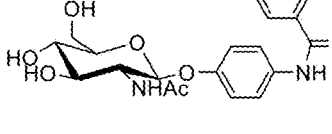 | 1 | + | | | |
| | | 100 | + | | | |
| 14 | 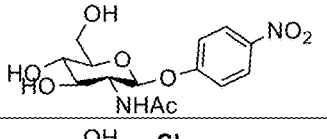 | 1 | +++ | | | |
| | | 100 | +++ | | | |
| 17 | 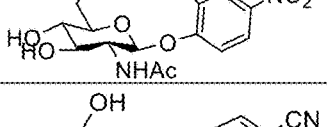 | 1 | | ++ | | |
| | | 100 | | | +++ | ++ |
FIG. 1

| # | Structure | Conc | Col3 | Col4 | Col5 | Col6 |
|---|---|---|---|---|---|---|
| 23 | 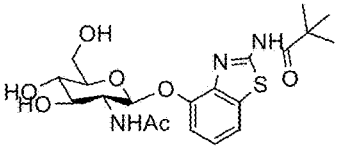 | 1 | + | | + | |
| | | 100 | + | | ++ | |
| 26 | 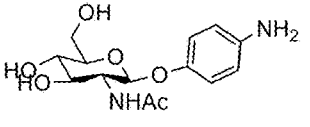 | 1 | | | | |
| | | 100 | | | | |
| 27 | 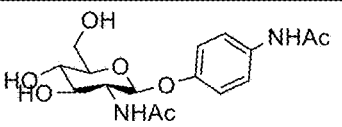 | 1 | | + | | |
| | | 100 | | ++ | | |
| 28 | 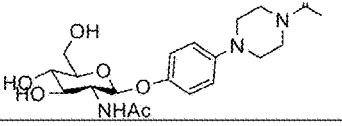 | 1 | + | | | |
| | | 100 | | | ++ | |
| 29 | 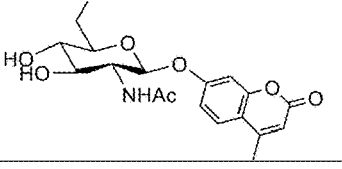 | 1 | | | | ++ |
| | | 100 | | | + | + |
| 30 | 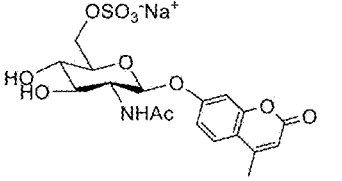 | 1 | + | | | |
| | | 100 | | | + | |
| 32 | 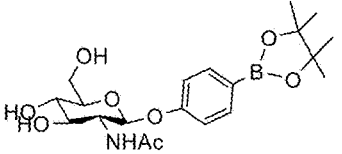 | 1 | +++ | +++ | | |
| | | 100 | +++ | + | | |
| 35 | 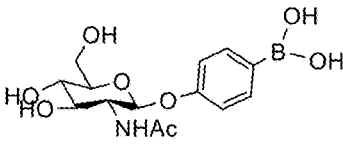 | 1 | +++ | | | |
| | | 100 | | | ++ | |
| 38 | 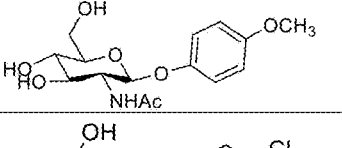 | 1 | | | | |
| | | 100 | | ++ | + | |
| 39 | 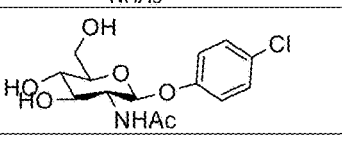 | 1 | | | | |
| | | 100 | | | + | |
FIG. 1 (continued)

| 40 |  | 1 | | | | |
| | | 100 | | | + | |

+ means % of inhibition or activation is in the range of 15-25%
++ means % of inhibition or activation is in the range of 25-75%
+++ means % of inhibition or activation is in the range of 75-95%

| Bacteria | MIC₉₀ (µg/mL) | | | | | ΣFIC AVR45 | ΣFIC AVR48 |
|---|---|---|---|---|---|---|---|
| | Colistin | AVR-45 | AVR-48 | MIC of AVR45 w/MIC of colistin | MIC of AVR48 w/ ¼ MIC of colistin | | |
| P. aeruginosa | 4 | 100 | 200 | 25 | 3.1 | 1.1 Additive | 0.5 Synergistic |
| MRSA *(MIC₅₀) | 200* | 100* | 100* | 6.25* | 3.1* | 1.0 Additive | 1.0 Additive |
| E. Coli | 8 | 100 | 200 | ND | 6.25 | ND | 0.9 Additive |

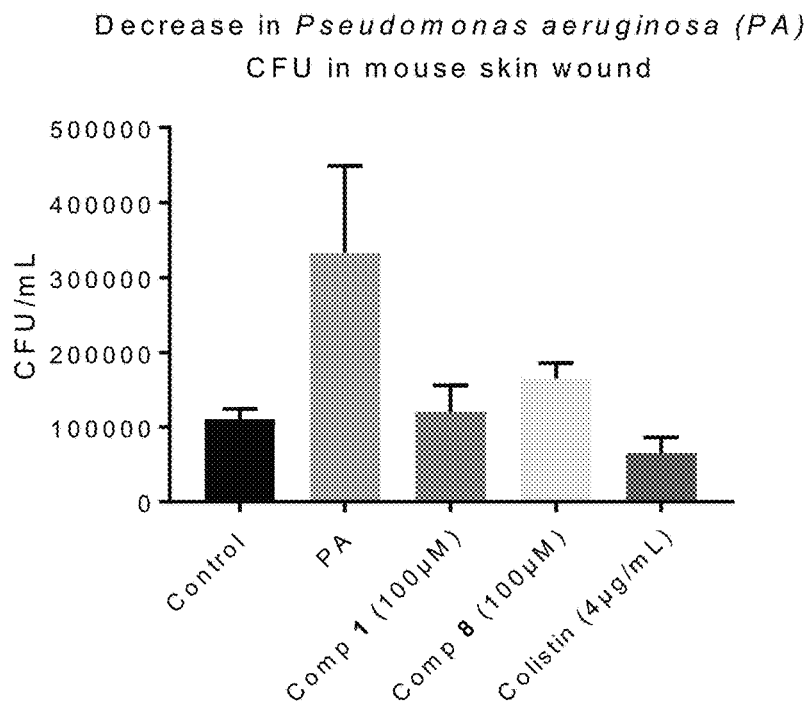
FIG. 21
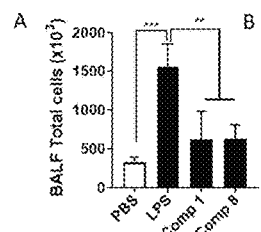 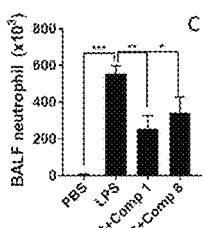 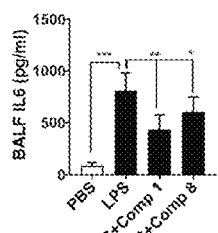 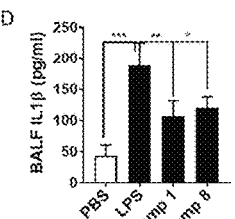 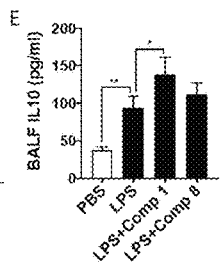
FIG. 22A     FIG. 22B     FIG. 22C     FIG. 22D     FIG. 22E
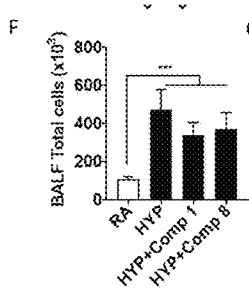 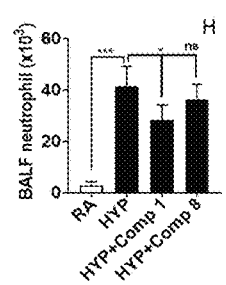 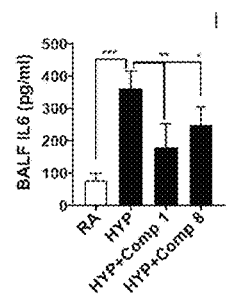 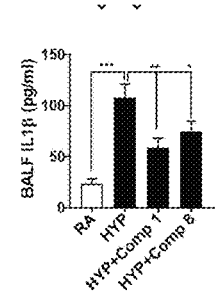 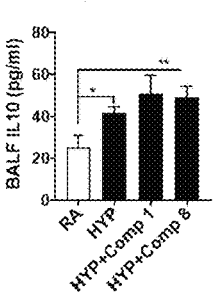
FIG. 22F     FIG. 22G     FIG. 22H     FIG. 22I     FIG. 22J

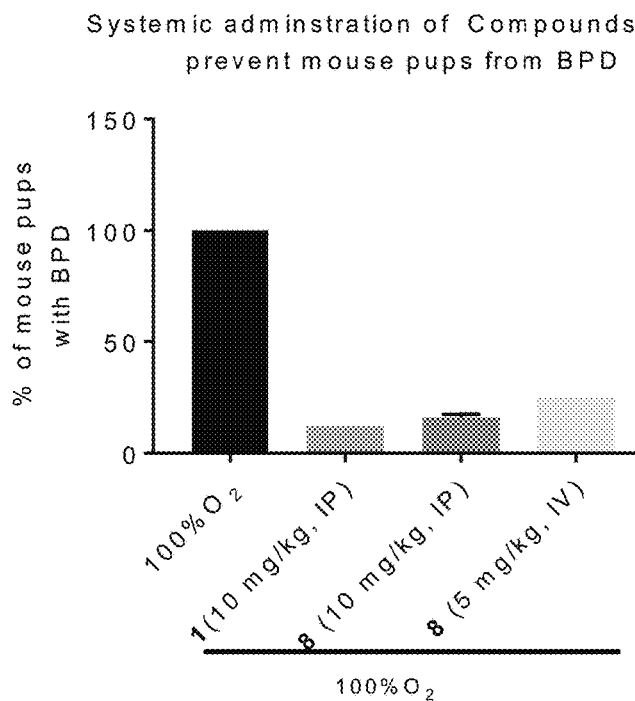
FIG. 24
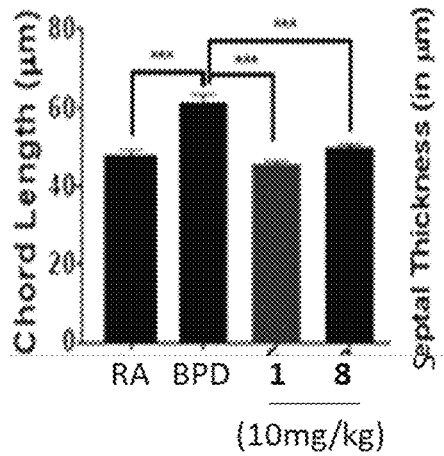 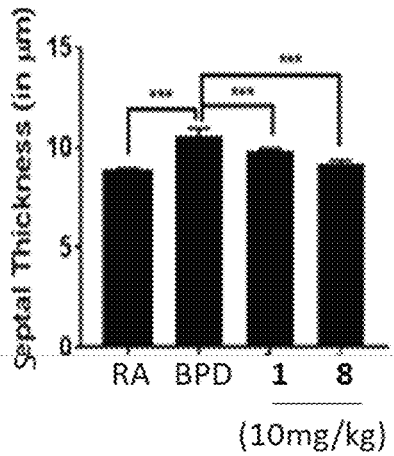 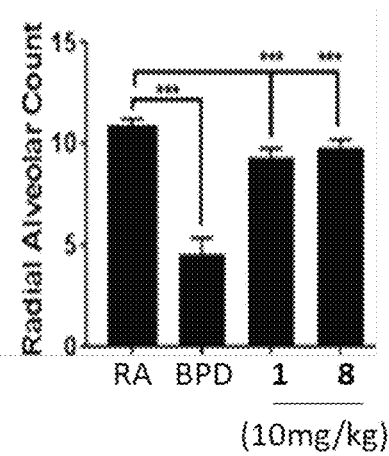
FIG. 25A  FIG. 25B  FIG. 25C
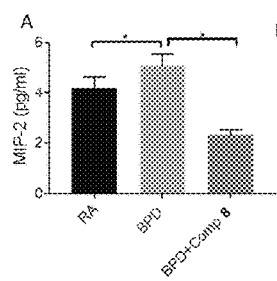 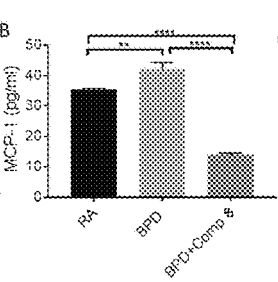 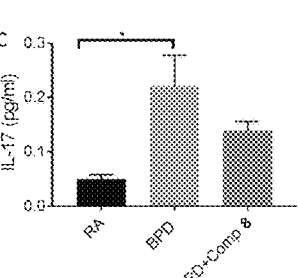 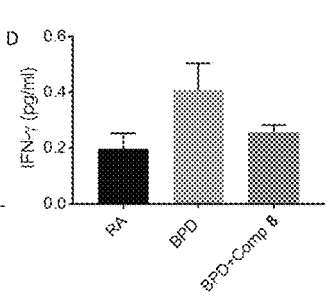
FIG. 26A  FIG. 26B  FIG. 26C  FIG. 26D

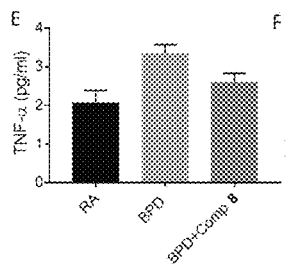
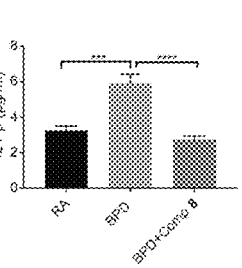
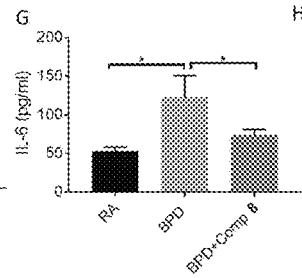
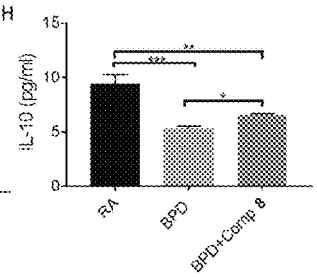
FIG. 26E  FIG. 26F  FIG. 26G  FIG. 26H
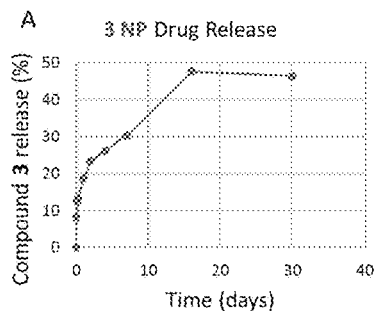
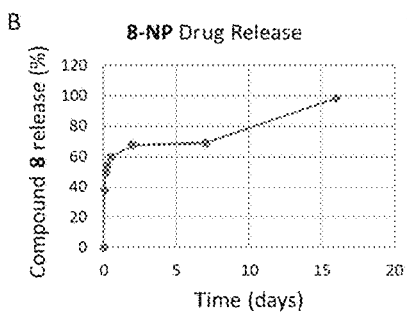
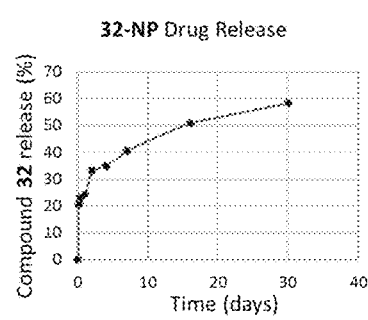
FIG. 27A  FIG. 27B  FIG. 27C
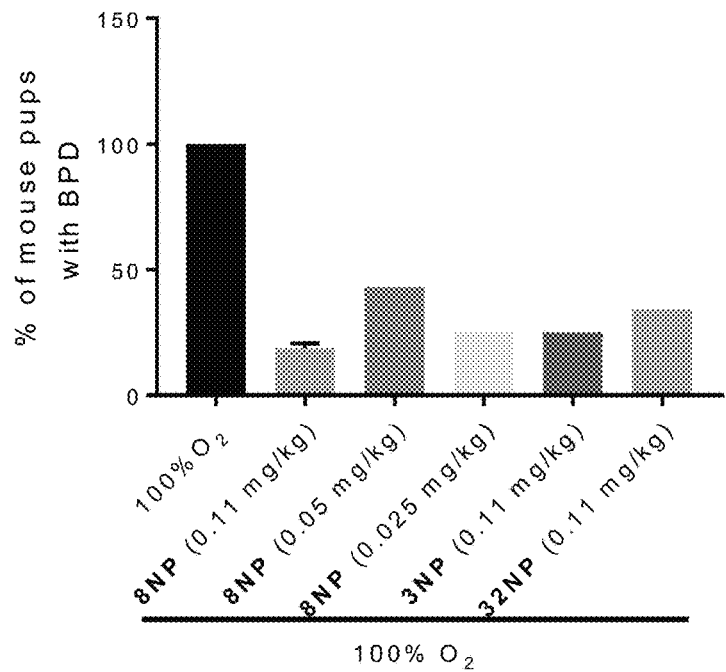
FIG. 28

IMMUNODULATING SMALL MOLECULES

CROSS-REFERENCE TO RELATED APPLICATIONS

This application claims priority to U.S. Provisional Application Ser. No. 62/693,023, filed Jul. 2, 2019, the entire contents of which are incorporated herein by reference.

STATEMENT OF FEDERALLY FUNDED RESEARCH

This research is partly funded by NIH/NIAID federal grant 1 R43 AI129164-01 awarded to AyuVis Research.

TECHNICAL FIELD OF THE INVENTION

The present invention relates in general to the field of novel immunomodulatory molecules, and more particularly, to carbohydrate derived Toll-like Receptor modulators. In one embodiment, this invention relates generally to compounds capable of stimulating or modulating an immune response in a subject. More particularly the invention pertains to novel combinations of antigens with small molecules to be used in vaccine therapies. The compounds in one embodiment can be used as adjuvants for prophylactic and therapeutic vaccines for infectious diseases and cancer. In another embodiment, they can be used as immunotherapeutics for cancer, infectious diseases, allergy/asthma, lung injury, bronchopulmonary dysplasia either alone or in combination with existing therapies. In a further embodiment, the invention pertains generally to methods of identifying small molecule immunomodulators, and, more particularly, to assays for detection of immunopotentiator and immunosuppressant by measurement of immunological markers, such as cytokines, chemokines, and/or growth factors.

BACKGROUND OF THE INVENTION

Without limiting the scope of the invention, its background is described in connection with diseases associated with inflammation and immune modulation.

Immunity. When the immune system is challenged by a foreign antigen it responds by launching a protective response. This response is characterized by the coordinated interaction of both the innate and acquired immune systems. These systems, once thought to be separate and independent, are now recognized as two interdependent parts that when integrated fulfil two mutually exclusive requirements: speed (contributed by the innate system) and specificity (contributed by the adaptive system).

The innate immune system serves as the first line of defense against invading pathogens, holding the pathogen in check while the adaptive responses are matured. It is triggered within minutes of infection in an antigen-independent fashion, responding to broadly conserved patterns in the pathogens (though it is not non-specific, and can distinguish between self and pathogens). Crucially, it also generates the inflammatory and co-stimulatory milieu (sometimes referred to as the danger signal) that potentiates the adaptive immune system and steers (or polarizes it) towards the cellular or humoral responses most appropriate for combating the infectious agent (discussed in more detail below).

The adaptive response becomes effective over days or weeks, but ultimately provides the fine antigenic specificity required for complete elimination of the pathogen and the generation of immunologic memory. It is mediated principally by T and B cells that have undergone germline gene rearrangement and are characterized by an exquisite specificity and long-lasting memory. However, it also involves the recruitment of elements of the innate immune system, including professional phagocytes (macrophages, neutrophils etc.) and granulocytes (basophils, eosinophils etc.) that engulf bacteria, viruses and even relatively large protozoal parasites. Once an adaptive immune response has matured, subsequent exposure to the pathogen results in its rapid elimination (usually before symptoms of infection become manifest) because highly specific memory cells have been generated that are rapidly activated upon subsequent exposure to their cognate antigen.

Interdependence of Innate and Adaptive Responses. It is now thought that the earliest events following pathogen invasion are affected by cellular components of the innate immune system. The response is initiated when resident tissue macrophages and dendritic cells (DCs) encounter pathogen and become activated by signals generated by interaction between pattern-recognition receptors (PRRs) and the pathogen-associated molecular patterns (PAMPs) shared by large groups of microorganisms. The activated macrophages and DCs are stimulated to release various cytokines (including the cytokines and chemokines such as TNF-$\alpha$, IL-1$\beta$, Il-6, IL-8, MIP-1$\alpha$ and MIP-1$\beta$), which constitute the "danger signal" and triggers an influx of Natural Killer (NK) cells, macrophages, immature dendritic cells into the tissues.

Loaded with antigen, the activated DCs then migrate to lymph nodes. Once there, they activate immune cells of the adaptive response (principally naïve B- and T-cells) by acting as antigen-presenting cells (APCs). The activated cells then migrate to the sites of infection (guided by the "danger signal") and once there further amplify the response by recruiting cells of the innate immune system (including eosinophils, basophils, monocytes, NK cells and granulocytes). This cellular trafficking is orchestrated by a large array of cytokines (particularly those of the chemokine subgroup) and involves immune cells of many different types and tissue sources (Luster 2002).

Polarization of the Adaptive Immune Response. The adaptive immune response is principally affected via two independent limbs: cell-mediated (type 1) immunity and antibody-mediated or humoral (type 2) immunity.

Type 1 immunity involves the activation of T-lymphocytes that either act upon infected cells bearing foreign antigens or stimulate other cells to act upon infected cells. This branch of the immune system therefore effectively contains and kills cells that are cancerous or infected with pathogens (particularly viruses). Type 2 immunity involves the generation of antibodies to foreign antigens by B-lymphocytes. This antibody-mediated branch of the immune system attacks and effectively neutralizes extracellular foreign antigens.

Both limbs of the immune system are important in fighting disease and there is an increasing realization that the type of immune response is just as important as its intensity or its duration. Moreover, since the type 1 and type 2 responses are not necessarily mutually exclusive (in many circumstances an effective immune response requires that both occur in parallel), the balance of the type1/type 2 response (also referred to as the Th1:Th2 response ratio/balance by reference to the distinct cytokine and effector cell subsets involved in the regulation of each response—see below) may also play a role in determining the effectiveness (and repercussions) of the immune defense.

In many circumstances the immune response is skewed heavily towards a type 1 or type 2 response soon after exposure to antigen. The mechanism of this type1/type 2 skewing or polarization is not yet fully understood, but is known to involve a complex system of cell-mediated chemical messengers (cytokines, and particularly chemokines) in which the type1/type 2 polarization (or balance) is determined, at least in part, by the nature of the initial PRR-PAMP interaction when the DCs and macrophages of the innate immune system are first stimulated and subsequently by the cytokine milieu in which antigen priming of naïve helper T cells occurs.

Two cytokines in particular appear to have early roles in determining the path of the immune response. Interleukin-1 (IL-1), secreted by macrophages, drives the type 1 response by stimulating the differentiation of Th1 cells, the helper cells that oversee the type 1 response. Another macrophage cytokine, interleukin-10 (IL-10) inhibits this response, instead driving a type 2 response.

The type 1 and type 2 responses can be distinguished inter alia on the basis of certain phenotypic changes attendant on priming and subsequent polarization of naïve helper T cells. These phenotypic changes are characterized, at least in part, by the nature of the cytokines secreted by the polarized helper T cells.

Th1 cells produce so-called Th1 cytokines, which include one or more of TNF-α, IL-1, IL-2, IFN-gamma, IL-12 and/or IL-18. The Th1 cytokines are involved in macrophage activation and Th1 cells orchestrate Type 1 responses. In contrast, Th2 cells produce so-called Th2 cytokines, which include one or more of IL-4, IL-5, IL-10 and IL-13. The Th2 cytokines promote the production of various antibodies and can suppress the type 1 response.

The involvement of Th1 and Th2 cells and cytokines in type 1:type 2 immune response polarization has given rise to the terms Th1 response and Th2 response being used to define the type 1 and type 2 immune responses, respectively. Thus, these terms are used interchangeably herein.

There is an increasing realization that the type of immune response is just as important in therapy and prophylaxis as its intensity or its duration. For example, an excess Th1 response can result in autoimmune disease, inappropriate inflammatory responses and transplant rejection. An excess Th2 response can lead to allergies and asthma. Moreover, a perturbation in the Th1:Th2 ratio is symptomatic of many immunological diseases and disorders, and the development of methods for altering the Th1:Th2 ratio is now a priority.

Vaccine adjuvants. Immune response to certain antigens that are otherwise weakly antigenic can be enhanced through the use of vaccine adjuvants. Such adjuvants potentiate the immune response to specific antigens and are therefore the subject of considerable interest and study within the medical community.

Research has permitted development of vaccines possessing antigenic epitopes that were previously impossible to produce. For example, currently available vaccine candidates include synthetic peptides mimicking streptococcal, gonococcal, and malarial antigens. These purified antigens are generally weak antigens, however, that require adjuvants in order to evoke protective immunity. However, conventional vaccine adjuvants possess a number of drawbacks that limit their overall use and effectiveness. Again, this is fine for vaccines but no other uses.

Substances that stimulate immune cells in vitro, exhibit similar immunostimulatory effects in vivo. These compounds, such as recombinant cytokines, pathogen products (e.g. toxins, lipids, proteins/peptides, carbohydrates and nucleic acids) and other mammalian-derived immunostimulatory molecules (e.g. heat shock proteins, complement, immune complexes and proteoglycans) all induce a measurable pro-inflammatory response both in vitro and in vivo.

Historically, the classic adjuvants have been Freund's complete or incomplete (i.e., without mycobacteria) adjuvants. Edmund Coley described the potential of Coley's toxin for cancer immuno-therapy. Other materials, such as mineral oil and aluminum hydroxide, have also been used as adjuvants, but they invariably suffer from disadvantages. For example, mineral oil is known to produce tissue irritation and to be potentially oncogenic. Alum, the only approved adjuvant in the United States, can induce granulomas at the inoculation site and does not effectively induce cell-mediated immunity. Moreover, many of the adjuvants currently available have limited utility because they contain components, which are not metabolizable in humans. Additionally, most adjuvants are difficult to prepare in that they may require time consuming procedures and the use, in some cases, of elaborate and expensive equipment to formulate a vaccine and adjuvant system.

Immunological adjuvants are described in "Current Status of Immunological Adjuvants", Ann. Rev. Immunol., 1986, 4, pp. 369-388, and "Recent Advances in Vaccine Adjuvants and Delivery Systems" by Derek T O'Hagan and Nicholas M. Valiente. See also U.S. Pat. Nos. 4,806,352; 5,026,543; and 5,026,546 for disclosures of various vaccine adjuvants appearing in the patent literature.

TLR4 agonist as immune stimulant. The use of immunomodulatory strategies aimed at improving resistance to bacterial infections could be beneficial in a variety of clinical scenarios in which the host is predisposed to infectious complications. Among those are patients with severe burns or major trauma, patients that have undergone major surgical procedures, or patients that have received immunosuppressive therapies for cancer or organ transplantation. The attractiveness of interventions that can improve the host response to infection is further enhanced by the increasing incidence of antibiotic resistance among bacteria, especially those that commonly cause nosocomial infections.

Immunocompromised patients have a higher risk of developing bacterial infections in the central nervous system (CNS) (Safdieh, Mead et al. 2008). The list of the pathogens includes many organisms with low pathogenicity in the immunocompetent host. Moreover, the distribution of the pathogens also differs from the immunocompetent host and depends on the nature of the immune defect. Patients with a decrease in B-lymphocyte function or with a loss of splenic function have an increased risk of meningitis caused by encapsulated bacteria, while patients with an impaired T-lymphocyte-macrophage system are more susceptible to CNS infections caused by intracellular pathogens. One additional cause of this increased susceptibility to CNS infections probably is a decreased local immune defense.

Bacterial lipopolysaccharide (LPS; endotoxin) is a component of the Gram-negative bacterial cell wall that has known immunomodulatory properties (Broad, Jones et al. 2006). LPS is recognized by Toll-Like receptor 4 (TLR4), which is expressed on a variety of leukocytes and activates both TRIF- and MyD88-dependent signaling pathways. Activation of TLR4 signaling induces the production of numerous proinflammatory mediators such as cytokines, chemokines, and nitric oxide that facilitate the cardinal features of inflammation such as increased vascular permeability, edema formation, and leukocyte recruitment. Interestingly, prior exposure to LPS induces a state in which a subsequent challenge with LPS or bacteria results in markedly decreased production of proinflammatory mediators (Cavaillon, Adrie et al. 2003). The altered immunological phenotype that is elicited by priming with LPS has historically been referred to as endotoxin tolerance (Cross 2002). The induction of endotoxin tolerance has been shown to be highly effective in reducing both morbidity and mortality associated with subsequent challenge with a normally lethal dose of LPS (Murphey, Fang et al. 2008). Because LPS priming attenuates proinflammatory cytokine production in response to LPS or bacterial challenge, many investigators previously characterized LPS tolerance as a state of immunosuppression. However, few studies have examined the effects of LPS treatment on the host response to live bacterial infections. Studies have demonstrated that mice primed with LPS have improved resistance to bacterial infections (Wy, Goto et al. 2000, Wynn, Scumpia et al. 2008). However, the clinical applicability of LPS as a therapeutic or prophylactic agent is precluded by toxicity and a narrow therapeutic index in humans.

Monophosphoryl Lipid A (MPLA), an endotoxin derivative that is used as a vaccine adjuvant in humans (Thoelen, Van Damme et al. 1998) is a TLR4 agonist. Pretreatment of MPLA prevents hypothermia, improves survival, and improves bacterial clearance in mice with systemic infection (Romero, Varma et al. 2011). The protective effects of MPLA are mediated through TLR4. Post-infection treatment with MPLA enhances bacterial clearance but does not attenuate inflammatory cytokine production or prevent hypothermia.

TLR7/8 agonist as immune stimulant. The transmembrane Toll-like receptors (TLR) have binding domains specific for different microbial and viral components (Takeda, Kaisho et al. 2003). TLR7/8 recognize single-stranded viral RNA (Diebold, Kaisho et al. 2004, Heil, Hemmi et al. 2004). Upon ligation of the receptor-ligand pair, intracellular signaling is initiated and downstream transcription factors activate genes of proinflammatory cytokines (TNF, IL-1), type I interferons (IFNα) and co-stimulatory molecules (CD80, CD86) (Lore, Betts et al. 2003, Russo, Cornella-Taracido et al. 2011, Desmet and Ishii 2012). The activation of these genes promotes maturation of dendritic cells (DCs), facilitating the presentation of antigen and stimulation of the ensuing adaptive immune response. The exact immune response generated depends upon the precise stimuli and resultant transcriptional and cellular changes. Cell-mediated immunity executed by $CD8^+$ T lymphocytes is enabled through accessory Th1 cells and the cytokines IFNα, IL-2 and IL-12 (Pennock, White et al. 2013). However, if innate, proinflammatory cytokines such as IL-1 and TNFα are produced in excess both local and systemic inflammation results. Accordingly, to create a safe adjuvant, that augments the immune response to a given antigen, the proper combination of these signals must be generated.

Several TLR7/8 agonists, including R848 and R837, have been investigated as potential vaccine adjuvants. Some of these agonists have found success as topically administered agents, but demonstrate dose-limiting toxicity when given orally or intravenously before ever reaching efficacious concentrations. This profile renders the current TLR7/8 agonists ineffective as systemic vaccine adjuvants (Pockros, Guyader et al. 2007). These agents were designed to be more potent than CL075 (TLR7/8 agonist) and induce lower inflammatory cytokine levels, thereby overcoming their issues as systemic adjuvants.

Acute Respiratory Distress Syndrome (ARDS) is a severe form of respiratory failure that develops in association with a variety of insults including massive hemorrhage, systemic infection, inhalation of noxious agents, bacterial infections, burns and blast trauma and has an overall mortality of 30-40%. It is estimated that 200,000 individuals develop ARDS each year in the United States (Rubenfeld, Caldwell et al. 2005, Villar, Blanco et al. 2016). One of the major complications of trauma-based morbidity in military combat is the development of ARDS, occurring in 8-82% of selected patient populations. These include patients with pulmonary contusions, severe trauma (Injury Severity Score>25), head injury, notable blood transfusion requirement, and major orthopedic injuries such as long-bone and pelvic fractures. The presence of ARDS is associated with a significant increase in morbidity, an increased use of hospital resources, and up to a 4.3-fold increase in mortality (Salim, Martin et al. 2006).

To date, there is no specific cure for ARDS. Current therapies only include supportive care, using a mechanical ventilator to support the lung until it fully recovers. Thus, new therapies for this disease are desperately needed.

Another such disease is Bronchopulmonary dysplasia (BPD), which is the most common chronic respiratory disease in infants and is a devastating condition that disrupts the developmental program of the lung secondary to preterm birth. BPD occurs secondary to an interaction between genetic and environmental factors (hyperoxia, invasive mechanical ventilation and sepsis) (Bhandari and Bhandari 2009, Bhandari and Bhandari 2011, Jensen and Schmidt 2014). Although the definition of BPD has evolved over the past decade, it is currently defined as the need for oxygen ($O_2$) supplementation for 28 days of life and a "physiologic" assessment of the supplemental $O_2$ requirement at 36 weeks postmenstrual age (Bhandari and Bhandari 2011, Trembath and Laughon 2012, Bancalari and Claure 2016). It is estimated that 10,000-15,000 new cases of BPD occur each year in the United States, and significantly, 97% of all BPD cases occur in infants with a birth weight less than 1250 grams (Bhandari and Bhandari 2011). Despite many advances in neonatal ventilation techniques, widespread use of surfactant and antenatal corticosteroids, as well as aggressive fluid management, the incidence of BPD has remained the same (Smith, Zupancic et al. 2005) or even increased slightly (Bhandari and Bhandari 2011, Trembath and Laughon 2012). Management of BPD takes a considerable toll on health services. Among preterm infants, the single costliest complication of hospitalization during infancy is BPD, with an average cost per discharge of $116,000 (Russell, Green et al. 2007). Additionally, BPD is associated with significant pulmonary and neurodevelopmental sequelae that continue to have health ramifications into adulthood (Bhandari and Bhandari 2011, Natarajan, Pappas et al. 2012, Bhandari and McGrath-Morrow 2013, Raju, Buist et al. 2017). It is thus important to understand the long-term consequences of BPD, as they are likely to have a significant impact on treatment and cost and application of health care during the lifetime of those born prematurely.

The pathologic hallmarks of BPD include: hyperoxia-induced pulmonary inflammation (Bhandari 2014, Balany and Bhandari 2015, Harijith and Bhandari 2016), increased cell death (Li, Choo-Wing et al. 2011, Choo-Wing R 2013, Sureshbabu, Syed et al. 2015, Sureshbabu, Syed et al. 2016), dysregulated angiogenic factors (Bhandari, Choo-Wing et al. 2008, Sun H 2013, Sun H 2013, Syed, Choo-Wing et al. 2016) culminating in impaired alveolarization and dysregulated vascularization of the lung (Balany and Bhandari 2015). Respiratory distress syndrome (RDS) and hyperoxia exposure are common antecedents of BPD. The current standard-of-care therapeutic approach to treat RDS in premature neonates is exogenous surfactant and supplemental oxygen, however, there is no specific and effective method of prevention or treatment of BPD (Bhandari 2014). According to the National Institute of Child Health and Human Development/National Heart, Lung and Blood Institute (NICHD/NHLBI), the identification of potential drugs to target BPD in preterm infants has been categorized as a "research priority" (McEvoy, Jain et al. 2014). The National Institutes of Health (NIH) workshop conducted under the auspices of the NHLBI of the NIH on the primary prevention of chronic lung diseases focused on BPD (McEvoy, Jain et al. 2014). In terms of "promising near-term opportunities for primary BPD prevention research," specifically, "clinical research priorities and specific clinical trials for BPD prevention," it was disappointing to note that only two specific drugs were named—caffeine and inhaled nitric oxide (iNO) (Bhandari 2014).

Reducing inflammation via activation of the anti-inflammatory cytokine IL-10 will be therapeutic for acute lung injury (ALI), ARDS and BPD, which are characterized by overproduction of pro-inflammatory cytokines TNF-α, IL-6, i-NOS and ROS as a result of bacterial infection, trauma, excess exposure to oxygen and noxious gases. These mediators induce endothelial and epithelial injury in lung, vascular leakage, edema, and vasodilatation, subsequently causing the development of ALI and ARDS (Densmore, Signorino et al. 2006). IL-10 primarily produced by T-helper 2 cells, B cells, monocytes, macrophages and keratinocytes is known to reduce the synthesis of pro-inflammatory cytokines and terminate inflammatory responses (Moore, Rousset et al. 1991). Low levels of IL-10 are found in patients with transfusion-related ALI (Kapur, Kim et al. 2017). Importantly, treatment with IL-10 alleviated lung injury induced by ischemia-reperfusion, lipopolysaccharide (LPS) (Bi, Wang et al. 2008), bleomycin and ozone; absence of endogenous IL-10 enhanced ALI induced by carrageenan. In addition to this, it was also reported that, pre-incubation of cultured fetal rat alveolar type II cells with recombinant IL-10 prior to 65% hyperoxia exposure decreased cellular necrosis and increased cell proliferation (Lee and Kim 2011). As reported by us (Bhandari 2008), and others (Li, Zhang et al. 2015), exogenous IL-10 treatment alleviated hyperoxia-induced ALI in mice, possibly by regulating neutrophil recruitment and the subsequent generation of cytokines, NO and matrix metalloproteinases.

Acne vulgaris is a common disorder that affects 17 million people in the U.S. alone. Although acne is rarely life threatening, it is a disease that can have a significant effect on patients' physical and psychological well-being. The pathogenesis of acne is multifactorial, including hormonal, microbiological, and immunological mechanisms. One of the factors that contributes to the pathogenesis of acne is *Propionibacterium acnes*, part of normal skin flora that can be significantly increased in the pilosebaceous units of patients with acne (Leyden, McGinley et al. 1975). Although *P. acnes* is a gram-positive bacterium, it is variably and weakly Gram-positive. It is described as diphtheroid or coryneform because it is rod-shaped and slightly curved. A number of unique features of the *P. acnes* cell wall and outer envelope further distinguishes it from other Gram-positive bacteria. *P. acnes* synthesizes phosphatidylinositol, this is unlike almost all other bacteria, but is made by virtually all eukaryotes. The peptidoglycan of *P. acnes* is distinct from most Gram-positive bacteria, containing a cross-linkage region of peptide chains with L, L-diaminopimelic acid and Dalanine in which two glycine residues combine with amino and carboxyl groups of two L, L-diaminopimelic acid residues (Kamisango, Saiki et al. 1982).

*P. acnes* contributes to the inflammatory nature of acne by inducing monocytes to secrete proinflammatory cytokines including TNF-α, IL-1β, and IL-8 (Vowels, Yang et al. 1995). In particular, IL-8 along with other *P. acnes*-induced chemotactic factors may play an important role in attracting neutrophils to the pilosebaceous unit. In addition, *P. acnes* releases lipases, proteases, and hyaluronidases which contribute to tissue injury (Hoeffler, Ko et al. 1976, Hoeffler 1977). For these reasons, *P. acnes* has been a major target of therapy in inflammatory acne.

The mechanism by which *P. acnes* activates monocyte cytokine release is unknown but is thought to involve pattern recognition receptors (PRRs)3 of the innate immune system. Recently identified Toll-like receptors (TLRs) are one example of PRR. Toll receptors were first identified in Drosophila, and mammalian homologues were found to mediate immune response to microbial ligands (Medzhitov, Preston-Hurlburt et al. 1997, Yang, Mark et al. 1998). Although it has been suggested that TLRs can discriminate between Gram-positive and Gram-negative organisms (Underhill, Ozinsky et al. 1999), bacterial ligands from Gram-positive bacteria have been identified that can activate monocytes via TLR2 or TLR4 (Takeuchi, Hoshino et al. 1999).

Reported evidence suggest that, *P. acnes* induces inflammatory cytokines in monocytes through a TLR2-dependent pathway. The expression of TLR2 in acne lesions indicates that activation of TLR2 can contribute to inflammation at the site of disease activity. Thus, a need remains for improved compositions and methods of treating these conditions.

Psoriasis. Interleukin (IL)-10 is an important immunoregulatory cytokine. One of its main biological function seems to be the limitation and termination of inflammatory responses. Remarkably, a relative deficiency in IL-10 expression is found in psoriasis, a frequent inflammatory skin disease, characterized by a type 1 cytokine pattern. Induction of IL-10 expression was found by conventional antipsoriatic therapies, suggesting that IL-10 may be a key cytokine in psoriasis and that application of this cytokine may have therapeutic effects. In first clinical trials over 3-7 weeks in patients with established psoriasis IL-10 was well tolerated and clinical efficient. In a long-term trial in patients with psoriasis in remission, IL-10 therapy decreased the incidence of relapse and prolonged the disease-free interval. Laboratory investigations suggest that IL-10 exerts its antipsoriatic activity by effects on different cell populations including antigen presenting cells and T-cells. IL-10 led to a lasting type 1/type 2 cytokine balance shift. Direct effects of IL-10 on keratinocytes, however, are unlikely to have contributed to the clinical response, since IL-10 unresponsiveness of keratinocytes was found in vitro. IL-10 seems to have major importance in psoriasis (Asadullah, Volk et al. 2002)

So far, IL-10 as a cytokine is therapeutically has been used as a recombinant protein i.e., a large molecule. Therefore, it's quite expensive to produce, must be administered by injection, which is quite inconvenient for the patient, and the induction of neutralizing antibodies, which might limit their effect, has to be excluded for long term application. Identification of molecules mediating the effects of this cytokine which are suitable for pharmacological intervention with small molecules will, therefore, of increasing interest. Induction of IL-10 cytokine production with low molecular weight compounds represent novel therapeutic approaches.

Arthritis. Rheumatoid arthritis (RA) is an autoimmune disorder that is characterized by a chronic synovitis which often leads to joint destruction. It is now established that proinflammatory cytokines such as TNF-β, IL-1, GM-CSF, and IL-6 are all produced by the synovial membrane in RA, and are considered to be important participants in the pathophysiology of the disease (Di Giovine, Nuki et al. 1988, Hirano, Matsuda et al. 1988, Miyasaka, Sato et al. 1988, Harris 1990).

Both mRNA and protein for IL-10 are present in the RA and osteoarthritis (OA) synovium, and that IL-10 is an important participant in the cytokine network of the rheumatoid synovial membrane, playing an immunoregulatory role in inflammatory and possibly T cell cytokine production. Reciprocally, IL-10 itself is regulated by IL-1 and TNF-α, thus IL-10 appears to be an important component of the complex cytokine network of rheumatoid synovitis. Finally, exogenous IL-10 was shown to inhibit both TNF-α and IL-β production by RA synovial membrane cultures. These findings raise the possibility of new therapeutic strategies of IL-10 upregulating agents for the treatment rheumatoid arthritis (Katsikis, Chu et al. 1994).

Lung cancer. Worldwide, lung cancer is the most common cause of cancer-related deaths in men and women. Lung cancer mortality rates have been rising in recent decades. Chronic inflammatory disease, such as chronic obstructive pulmonary disease (COPD), has been identified as a risk factor for lung cancer. Since TLR4 is also actively involved in the immune response against cancers, researchers have postulated that TLR4 exerts both a defensive role in normal cells and a negative role in cancer cells (Starska, Forma et al. 2012). However, the available evidence is still not conclusive on the link between TLR4 and lung cancer. A study of functional TLR-4 and mutated TLR4 in mice found that mice with the former had less lung capillary permeability, less weight loss, leukocyte inflammation, and primary tumor formation. Thus, the authors, Bauer et al, postulated that TLR4 inhibits lung carcinogenesis by inhibiting tumor progression. (Bauer, Dixon et al. 2005) The researchers proved TLR4 activation could protect the lungs from being inflamed during any potential tumorigenesis. (Bauer, Fostel et al. 2009) Elsewhere, a lower level of TLR4 in the nasal epithelium of a smoker compared with a nonsmoker was observed, with a profound reduction in patients with severe COPD. (MacRedmond, Greene et al. 2007) This finding suggests the potential role of TLR4 for airway inflammation and lung cancer progression. In vitro studies have also found that TLR4 is constantly expressed and upregulated on human lung cancer cells. (Zhang, He et al. 2009) In one study, the level of TLR4 was significantly linked with the production of immunosuppressive cytokines, production of proangiogenic chemokine, and with resistance to apoptosis by lung cancer cells. (He, Liu et al. 2007) Despite the reported significance of TLR-9 in lung cancer progression, (Droemann, Albrecht et al. 2005, Wang, Rayburn et al. 2006, Manegold, Gravenor et al. 2008, Ren, Wen et al. 2008) a positive correlation (P,0.05) of TLR4, but not TLR-9, with tumor differentiation in lung cancer patients was reported. (Zhang, He et al. 2009).

Angiogenesis. Posterior segment neovascular ocular diseases, as exemplified by proliferative diabetic retinopathy (PDR), exudative age-related macular degeneration (AMD) and retinopathy of prematurity (ROP), are a growing and huge health threat which require new effective therapies. Retinal neovascularization associated with PDR is the leading cause of blindness in working age adults. Choroidal neovascularization (CNV) is responsible for 200,000 new cases of exudative AMD each year in the US rendering this neovascular pathology the leading cause of legal blindness in non-third world nations. The projected number of people with AMD in 2020 is 196 million, increasing to 288 million in 2040 [Wong et al, The Lancet Global Health 2014, 2, e106-e116]. Pathological angiogenesis associated with ROP is the major cause of blindness in children under the age of seven [Harrell et al, Neonatal Network 2007, 26, 371-378].

Toll Like Receptor (TLR2/4) signaling may be associated with pathologic changes in retinal diseases [Cho et al, Investigative Ophthalmology & Visual Science 2009, 50, 5614-5618], including AMD eyes by oxidized lipids, lipofuscin and by drusen components. Once activated, TLR4 could contribute to the pathogenesis of AMD by multiple mechanisms such as release of TNF-α, interleukin-1β, and other pro-inflammatory mediators. TLR4 activation suppresses Wnt signaling, leading to reduced growth factor expression, secretion, and increased photoreceptor death in response to oxidative stress as well as can also lead to oxidative damage of photoreceptor outer segments. TLR4 has a direct effect on several inflammation-related signaling pathways including MAPK, NFk-B and Jak1/Stat1 and shown to mediate neuronal toxicity through caspase-3, neuronal iNOS and ERK1/2, JNK1/2 and p38. Interestingly, TLR4-mediated microglial activation by endogenous photoreceptor proteins in retinal inflammation can aggravate retinal cell death. Finally, release of high-mobility group box-1 in ischemic neural tissue has been shown to initiate TLR4-dependent responses that contribute to retinal neovascularization [He et al, Arteriosclerosis, Thrombosis, and Vascular Biology. 2013; 33:330-338].

Accordingly, there exists a need for more effective treatments for inflammation and in particular for both dry and wet AMD pathogenesis. The compounds and methods described herein, therefore demonstrated that inhibition of TLR2/4 activity is of therapeutic value in ROP, DR, AMD and other retinal diseases. The compounds of present innovation are small molecules that can synergistically inhibit angiogenesis, inflammation and accelerate phagocytosis with therapeutic potential to treat these diseases.

SUMMARY OF THE INVENTION

The compounds of present invention possess chemical structures with easier synthetic route compared to MPLA and other TLR4 agonists (Adanitsch, Shi et al. 2018). The compounds of the present invention are found unexpectedly as TLR4, TLR6, TLR7 and TLR8 agonists. They enhance bacterial and viral clearance as well as decrease inflammatory cytokine production after post infection treatment demonstrating a balance in Th1 and Th2 cytokine production by these compounds, which is not shown by MPLA. Pretreatment of some of the compounds of present invention stimulated the human monocytes into macrophages and increase the intracellular phagocytosis of bacteria thus possess immune stimulant activity. Post treatment by some of the compounds of present invention decreased inflammatory cytokines in mouse models of BPD, ARDS, and prevent tissue injury thus possess anti-inflammatory activity. The compounds of the present invention are found unexpectedly as TLR2, TLR4, TLR7, TLR8 and TLR9 antagonists. Treatment with some of these compounds of present invention arrest the lung cancer cell proliferation and decrease new tube formation in endothelial cells thus possess anti-cancer and anti-angiogenic activities respectively.

In one embodiment, the present invention includes a compound with the Formula I:

Formula-I

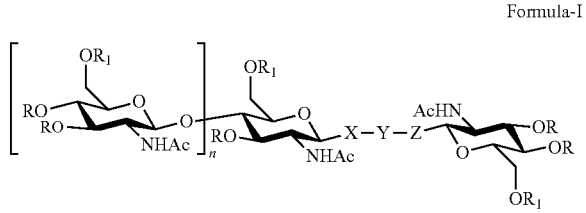

where n=0-5; X=NH, O, S, CH$_2$; Y=Phenyl, or a phenyl group substituted with at least one methyl, a phenyl group substituted with at least one nitro, a phenyl group substituted with at least one nitrogen, a phenyl group substituted with at least one boron, or aryl, substituted aryl, heteroaryl, four to six membered cycloalkyl, four to six membered heterocycloalkyl; R=H, C(O)R$_2$, SO$_2$R$_2$; R$_1$=H, C(O)R$_2$, SO$_2$R$_2$; R$_2$=Ethyl, methyl, isopropyl, n-propyl, t-butyl, n-butyl, NH$_2$, NR$_3$R$_4$; R$_3$, R$_4$=Ethyl, methyl, isopropyl, n-propyl, t-butyl, n-butyl, three to six membered cycloalkyl and Z=NH, O, S, CH$_2$, or none. In one aspect, an amount of the compound is varied or selected to to either inhibit or activate the immune response. In one aspect, the compound has the formula:

1

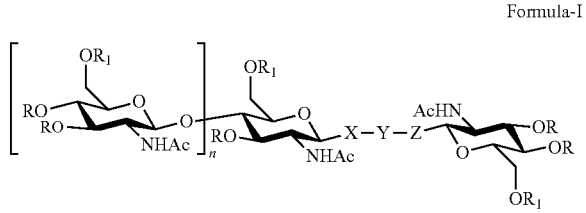

2

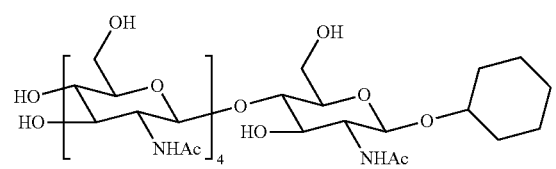

3

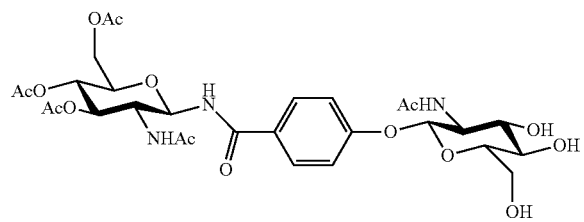

4

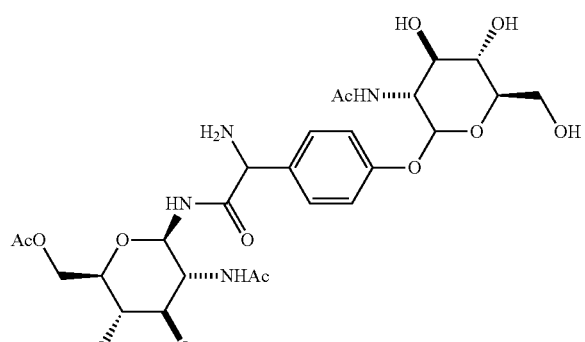

5

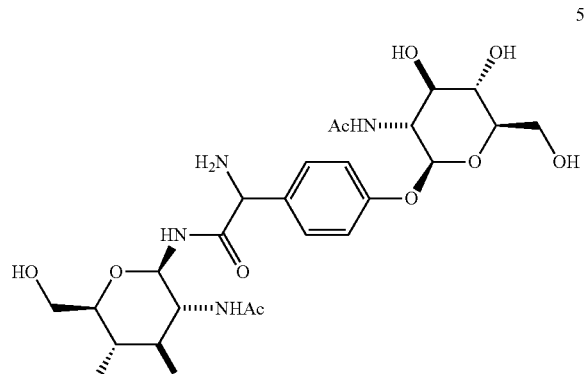

6

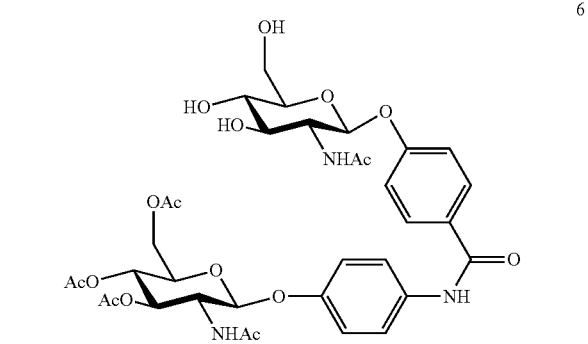

7

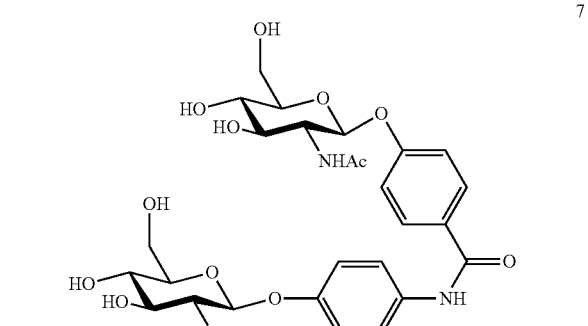

8

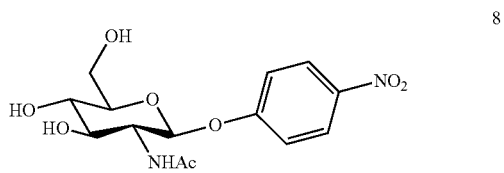

-continued 9
10
11
12
13
14
15
16
17
18
19
20
21
22
23

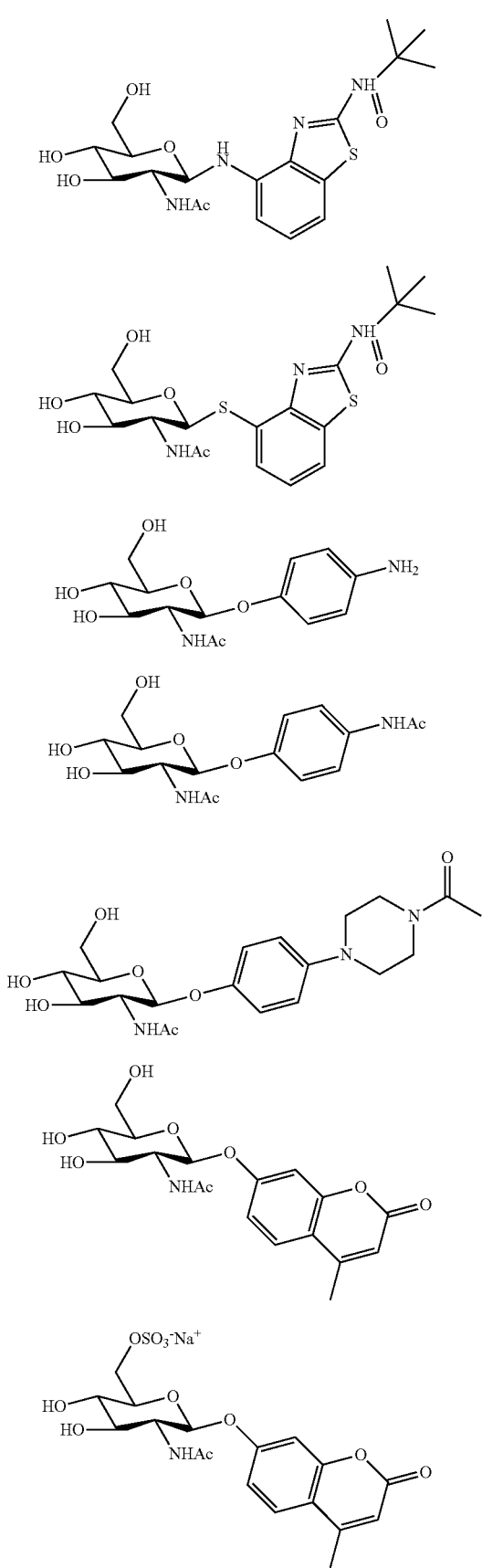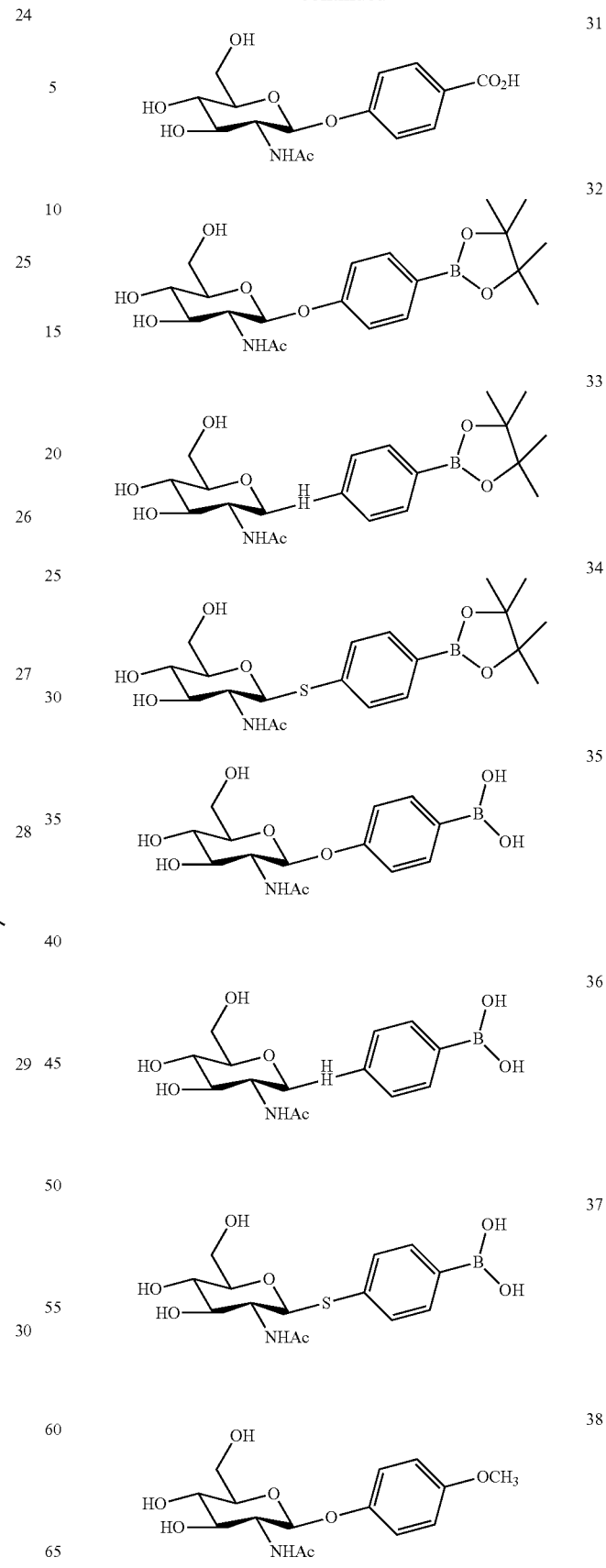

-continued
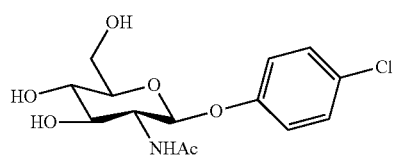
39
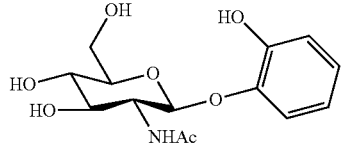
40
In one aspect, the compound inhibits a TLR4, a TLR2, or both a TLR2 and TLR4 receptor and has the formula, and concentration below:
| Compound Number | Structure | Concentration (μm) | % inhibition over control TLR4 | TLR2 |
|---|---|---|---|---|
| 1 | 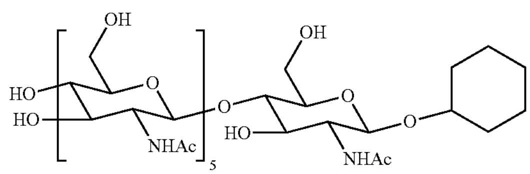 | 1-10<br>75-100 | +++<br>+++ | |
| 2 | 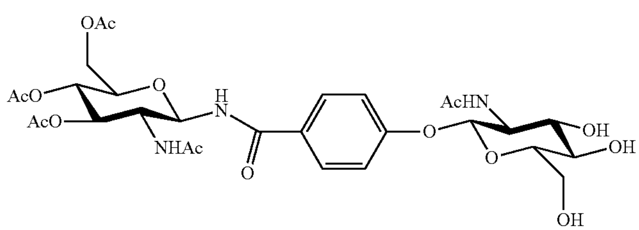 | 1-10<br>75-100 | ++<br>+++ | +<br>+++ |
| 3 | 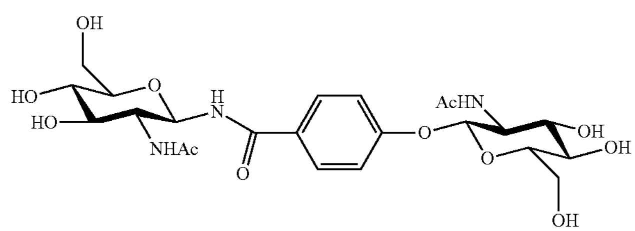 | 1-10<br>75-100 | ++<br>+++ | ++<br>+++ |
| 6 | 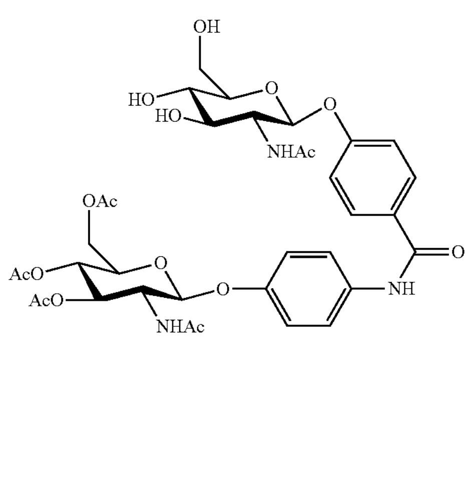 | 1-10<br>75-100 | ++<br>+++ | |

| Compound Number | Structure | Concentration (μm) | % inhibition over control TLR4 | TLR2 |
|---|---|---|---|---|
| 7 | (structure) | 1-10<br>75-100 | +++<br>+++ | ++<br>+++ |
| 11 | (structure) | 1-10<br>75-100 | +<br>+ | |
| 14 | (structure) | 1<br>100 | +++<br>+++ | |
| 23 | (structure) | 1-10<br>75-100 | +<br>+ | |
| 32 | (structure) | 1-10<br>75-100 | +++<br>+++ | +++<br>+ |
| 35 | (structure) | 1-10<br>75-100 | +++ | |

-continued

| Compound Number | Structure | Concentration (μm) | % inhibition over control | |
|---|---|---|---|---|
| | | | TLR4 | TLR2 |
| 38 | [structure: 4-methoxyphenyl 2-acetamido-2-deoxy-β-D-glycopyranoside] | 1-10<br>75-100 | | <br>++ |

In another aspect, the compound inhibits the immune response at a first concentration, and activates the immune response at a second concentration, wherein the compound is formulated into a low or a high dose composition comprising:

| Compound Number | Structure | Concentration (μM) | % inhibition over control | | % activation over control | |
|---|---|---|---|---|---|---|
| | | | TLR4 | TLR2 | TLR4 | TLR2 |
| 8 | [structure: 4-nitrophenyl 2-acetamido-2-deoxy-β-D-glycopyranoside] | 1-10<br>75-100 | +++ | +<br>++ | ++ | ++ |
| 17 | [structure: benzofurazan glycoside] | 1-10<br>75-100 | ---<br>----- | ++<br>+++ | | ++ |
| 28 | [structure: 4-(4-acetylpiperazinyl)phenyl glycoside] | 1-10<br>75-100 | + | | ++ | |
| 29 | [structure: 4-methylumbelliferyl glycoside] | 1-10<br>75-100 | | <br>+ | | ++<br>+ |

-continued

| Compound Number | Structure | Concentration (μM) | % inhibition over control TLR4 | % inhibition over control TLR2 | % activation over control TLR4 | % activation over control TLR2 |
|---|---|---|---|---|---|---|
| 30 | 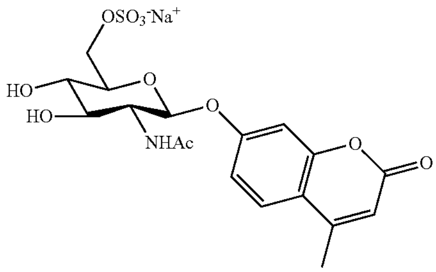 | 1-10<br>75-100 | | | + | + |
| 35 | 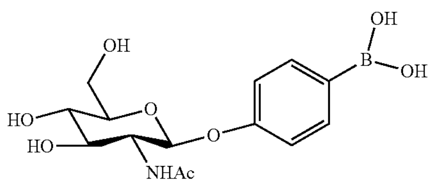 | 1-10<br>75-100 | +++ | | ++ | |

In another aspect, the compound has the formula:

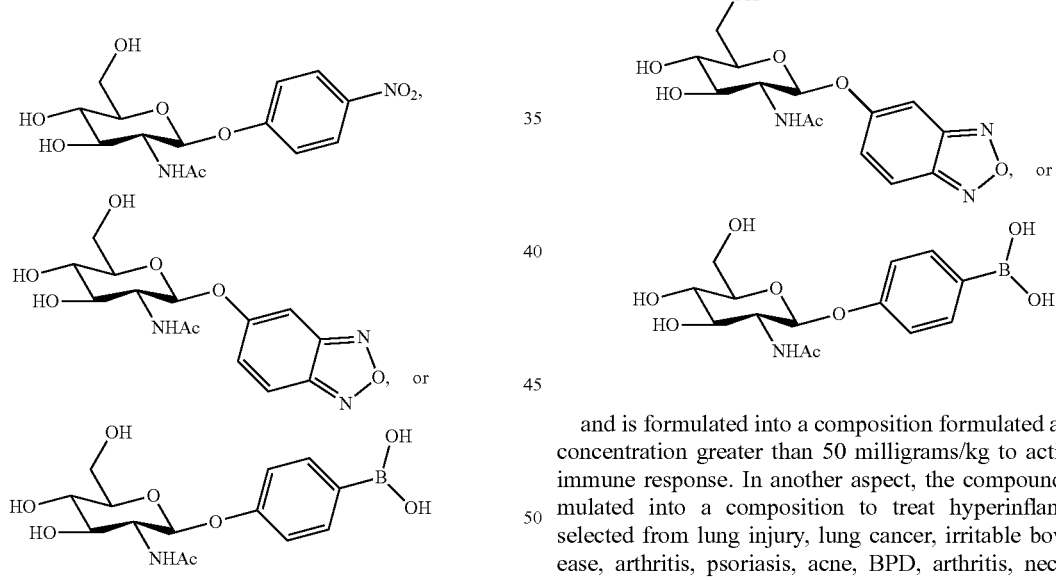

and is formulated into a composition at a low concentration of between 0.1-50 milligrams/kg to inhibit an immune response.

In another aspect, the compound has the formula and is formulated into a composition formulated at a high concentration greater than 50 milligrams/kg to activate an immune response. In another aspect, the compound is formulated into a composition to treat hyperinflammation selected from lung injury, lung cancer, irritable bowel disease, arthritis, psoriasis, acne, BPD, arthritis, necrotizing enterocolitis or sepsis, and is provided at a low concentration to inhibit an immune response, wherein the compound is selected from:

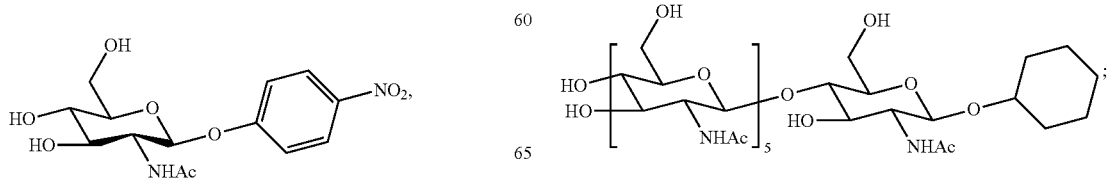

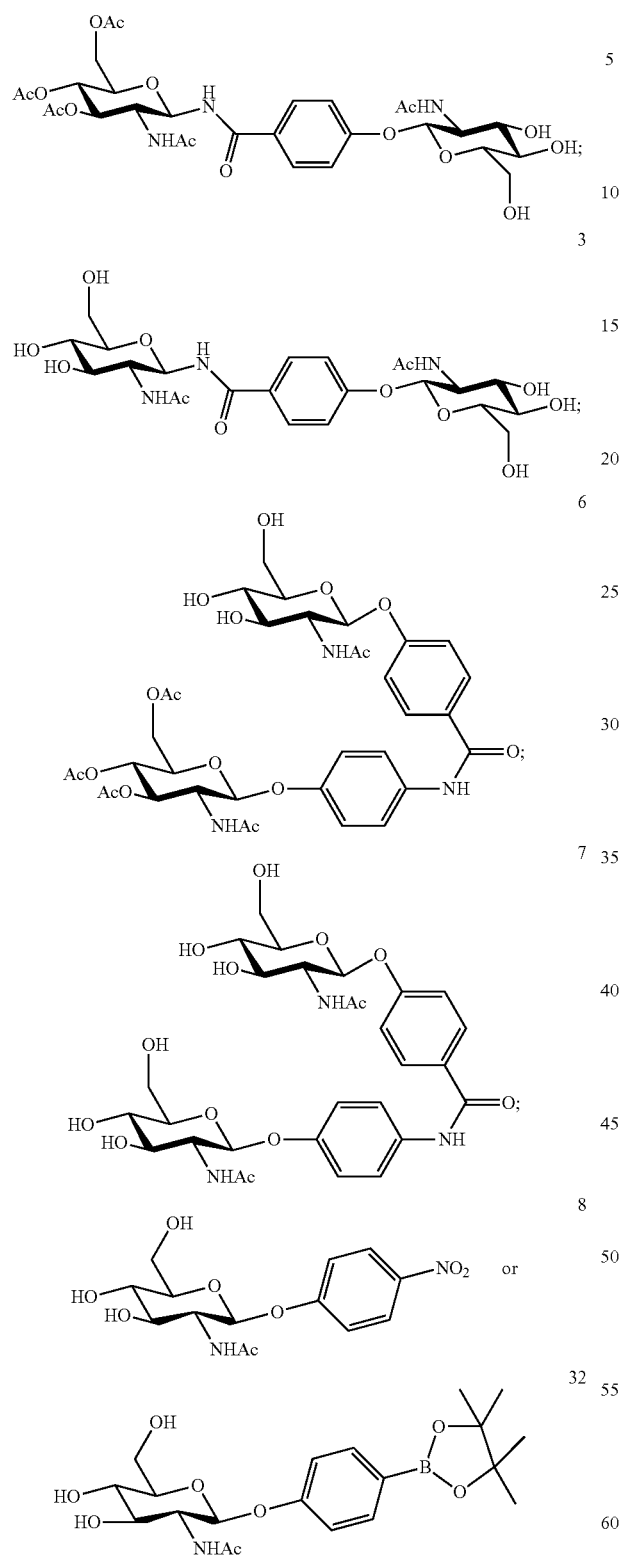
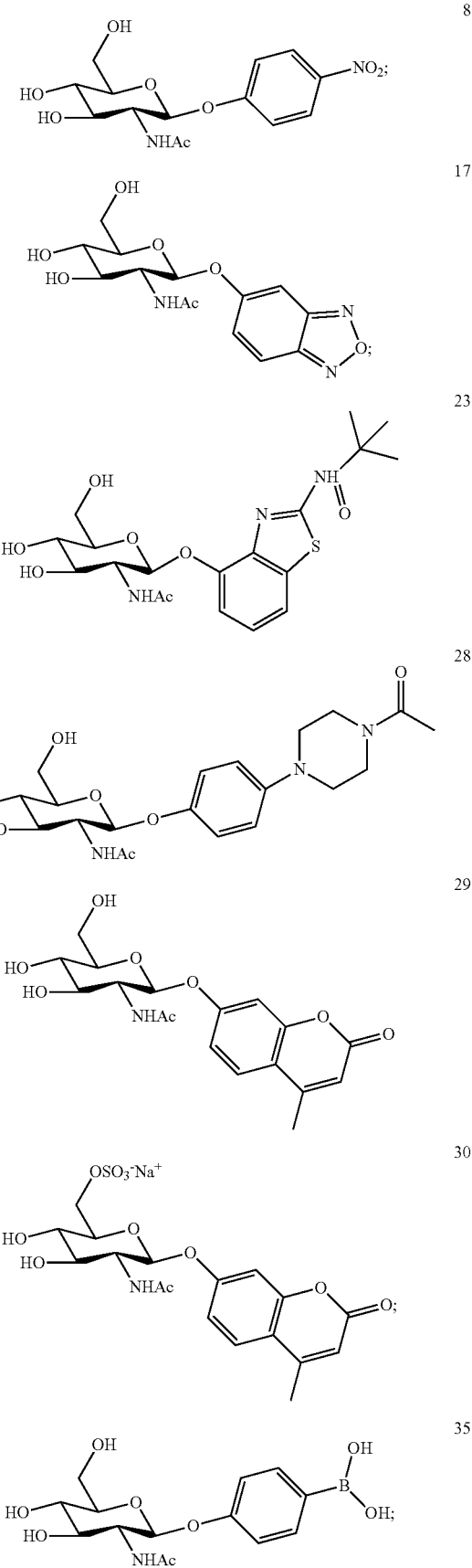
In another aspect, the compound is formulated into a composition to activate the immune response as a vaccine adjuvant, antimicrobial, antibacterial, antiviral or immune stimulator, wherein the compound is selected from:

-continued

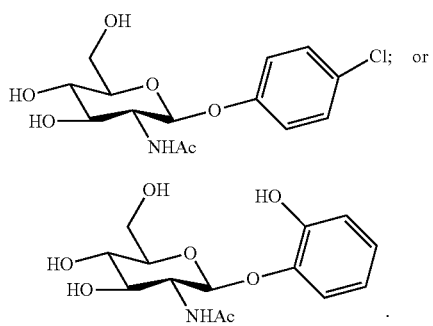

39 ... or

40

In another aspect, the compound is formulated into a pharmaceutical composition comprising one or more pharmaceutically acceptable excipients, buffers, or salts. In another aspect, the compound is formulated into a pharmaceutical composition adapted for pulmonary, alveolar, enteral, parenteral, intravenous, topical, or oral administration. In another aspect, the compound is formulated into an aerosol, a nebulizer, or an inhaler. In another aspect, the compound is used in a composition further comprising one or more liposomes, polymers, surfactants, salts, or buffers. In another aspect, the compound is used in a composition further comprising an additional therapeutic agent selected from the group consisting of corticosteroids, bronchodilators, anticholinergics, vasodilators, diuretics, anti-hypertensive agents, acetazolamide, antibiotics, antivirals, immunosuppressive drugs, and surfactants. In another aspect, the compound is provided in an amount that competitively inhibits inflammation and activates macrophages to protect lung tissue damage or limit lung tissue injury. In another aspect, the compound is provided in an amount that is a TLR4 modulator and upregulates IL-10. In another aspect, the compound is provided in an amount that is a TLR2, TLR4, TLR7 and TLR8 inhibitor and downregulates IL-1β. In another aspect, the compound is a TLR9 inhibitor and down regulates IFN-α.

In another aspect, each of the one or more compounds is able to bind directly to an active site of TLR4. In another aspect, the compound binds to TLR2, TLR6, TLR7 and TLR8 but not to TLR1 and TLR5. In another aspect, the compound is formulated into a pharmaceutical composition comprising one or more pharmaceutically acceptable excipients, buffers, or salts. In another aspect, the compound is formulated into a pharmaceutical composition adapted for pulmonary, alveolar, enteral, parenteral, intravenous, topical, or oral administration. In another aspect, the compound is formulated into an aerosolized form. In another aspect, the compound is adapted for use in a nebulizer or an inhaler. In another aspect, the composition further comprises one or more liposomes, polymers, surfactants, salts, or buffers. In another aspect, the composition further an additional therapeutic agent selected from the group consisting of corticosteroids, bronchodilators, anticholinergics, vasodilators, diuretics, anti-hypertensive agents, acetazolamide, antibiotics, anti-virals, anti-cancer, immunosuppressive drugs, and surfactants. In another aspect, the compound competitively inhibits inflammation and activates alternate pathway of macrophages to protect lung tissue damage or limit lung tissue injury. In another aspect, the compounds selectively kill lung cancer cells and not the normal lung epithelial cells. In another aspect, the compounds are not cytotoxic to peripheral blood monocyte, human umbilical vascular endothelial cells (HUVECs). In another aspect, the compounds decrease VEGF induced angiogenesis in HUVECs.

A method of treating a pulmonary disorder comprising identifying a subject in need of treatment for a pulmonary disorder; and providing the subject with an effective amount of a compound with the Formula (Formula I):

Formula-I

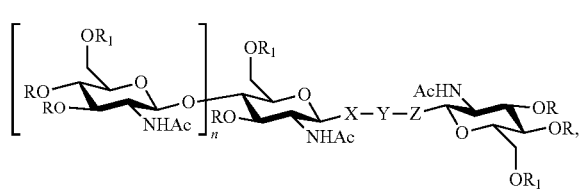

where n=0-5; X=NH, O, S, CH$_2$; Y=Phenyl, or a phenyl group substituted with at least one methyl, a phenyl group substituted with at least one nitro, a phenyl group substituted with at least one nitrogen, a phenyl group substituted with at least one boron, aryl, substituted aryl, heteroaryl, four to six membered cycloalkyl, four to six membered heterocycloalkyl; R=H, C(O)R$_2$, SO$_2$R$_2$; R$_1$=H, C(O)R$_2$, SO$_2$R$_2$; R$_2$=Ethyl, methyl, isopropyl, n-propyl, t-butyl, n-butyl, NH$_2$, NR$_3$R$_4$, R$_3$, R$_4$=Ethyl, methyl, isopropyl, n-propyl, t-butyl, n-butyl, three to six membered cycloalkyl and Z=NH, O, S, CH$_2$ or none. In one aspect, the amount of the compound in a formulation or composition is varied or selected to either inhibit or activate the immune response.

In one aspect, the compound is 1 or 2 or 3 or 13. In another aspect, the subject is a human. In another aspect, the pulmonary disorder is Acute Respiratory Distress Syndrome (ARDS), Adult Respiratory Distress Syndrome (Adult RDS), hyperoxic lung injury, or Bronchopulmonary dysplasia (BPD). In another aspect, the pulmonary disorder is chronic obstructive pulmonary disease (COPD), exacerbated COPD, Cystic Fibrosis, Asthma, severe Asthma, exacerbated Asthma, allergic Asthma, Acute lung injury, Idiopathic pulmonary fibrosis, Airway remodeling, Bronchiolitis obliterans syndrome or Lung cancer. In another aspect, the compound is formulated into a pharmaceutical composition adapted for pulmonary, alveolar, enteral, parenteral, intravenous, topical, or oral administration. In another aspect, the compound is administered by a nebulizer or an inhaler. In another aspect, the compound is inhaled in an aerosolized form. In another aspect, the compound is inhaled in an aerosolized form that comprises droplets less than 10 micrometers in diameter, wherein the droplets comprise the compound in a suitable pharmacologically acceptable liquid carrier. In another aspect, the compound is inhaled in a powder form comprising particles less than 10 micrometers in diameter. In another aspect, the subject is a premature infant born at an age of about 24 to about 32 weeks gestation. In another aspect, the subject is an infant and the weight of the infant at birth is about 1500 grams or less. In another aspect, the subject is an infant and the weight of the infant at birth is about 1000 grams or less. In another aspect, the subject is an infant and the at least one additional agent or therapy is selected from the group consisting of oxygen therapy, ventilator therapy, and a bronchodilator. In another aspect, the method further comprises administering an additional therapeutic agent selected from the group consisting of corticosteroids, bronchodilators, anticholinergics, vasodilators, diuretics, anti-hypertensive agents, acetazolamide, antibiotics, immunosuppressive drugs, surfactants and supplemental oxygen. In another aspect, the compound is provided in an amount sufficient to competitively inhibit inflammation and activate an alternate pathway of macrophages activation that protects lung tissue damage or limits lung tissue injury. In another aspect, the compound is a TLR4 modulator and upregulates IL-10. In another aspect, the compound is a TLR2, TLR4, TLR7 and TLR8 inhibitor and downregulates IL-1β. In another aspect, the compound is a TLR9 inhibitor and down regulates IFN-α. In another aspect, the compound inhibits cancer cell proliferation and induces cancer cell death. In another aspect, the compound inhibits angiogenesis. In another aspect, the compound is provided in an amount sufficient to competitively inhibit inflammation and angiogenesis and protect from ocular angiogenesis related injury.

A method of suppressing inflammation via inhibiting TLR2, TLR4, TLR7, TLR8 and TLR9 pathways and up-regulating the anti-inflammatory cytokine IL-10 comprising: identifying a subject in need of treatment for a pulmonary disorder; and providing the subject with an effective amount of a compound with the Formula I:

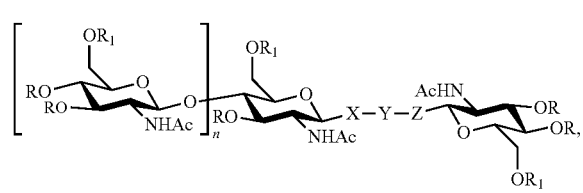

Formula-I wherein n=0-5; X=NH, O, S, $CH_2$; Y=Phenyl, a phenyl group substituted with at least one methyl, a phenyl group substituted with at least one nitro, a phenyl group substituted with at least one nitrogen, a phenyl group substituted with at least one boron, aryl, substituted aryl, heteroaryl, four to six membered cycloalkyl, four to six membered heterocycloalkyl; R=H, C(O)$R_2$, $SO_2R_2$; $R_1$=H, C(O)$R_2$, $SO_2R_2$; $R_2$=Ethyl, methyl, isopropyl, n-propyl, t-butyl, n-butyl, $NH_2$, $NR_3R_4$, $R_3$, $R_4$=Ethyl, methyl, isopropyl, n-propyl, t-butyl, n-butyl, three to six membered cycloalkyl and Z=NH, O, S, $CH_2$ or none, wherein the compound suppresses inflammation via inhibiting TLR4/TLR2 pathways and up-regulates the anti-inflammatory cytokine IL-10 in vivo. In certain aspects, the amount of the compound is formulated in an amount that is selected to either inhibit or activate the immune response as set forth in the tables hereinabove. In one aspect, the composition improves pulmonary barrier function in vivo. In another aspect, the subject is a premature infant born at an age of about 24 to about 32 weeks gestation. In another aspect, the subject is an infant and the weight of the infant at birth is about 1500 grams or less. In another aspect, the subject is an infant and the weight of the infant at birth is about 1000 grams or less. In another aspect, the subject is an infant and the at least one additional agent or therapy is selected from the group consisting of oxygen therapy, ventilator therapy, and a bronchodilator. In another aspect, the compound is administered by a nebulizer or an inhaler. In another aspect, the compound is inhaled in an aerosolized form. In another aspect, the compound is inhaled in an aerosolized form that comprises droplets less than 10 micrometers in diameter, wherein the droplets comprise the compound in a suitable pharmacologically acceptable liquid carrier. In another aspect, the compound is inhaled in a powder form comprising particles less than 10 micrometers in diameter. In another aspect, the subject has a pulmonary disorder selected from chronic obstructive pulmonary disease (COPD), exacerbated COPD, Cystic Fibrosis, Asthma, severe Asthma, exacerbated Asthma, allergic Asthma, Acute lung injury, Idiopathic pulmonary fibrosis, Airway remodeling, or Bronchiolitis obliterans syndrome. In another aspect, the subject has sepsis or acute lung injury (ALI). In another aspect, the compound is formulated into a pharmaceutical composition adapted for pulmonary, alveolar, enteral, parenteral, intravenous, topical, or oral administration.

A compound with the Formula I:

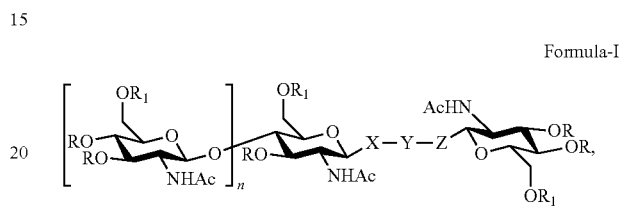

Formula-I wherein n=0-5; X=NH, O, S, $CH_2$; Y=Phenyl, or a phenyl group substituted with at least one methyl, a phenyl group substituted with at least one nitro, a phenyl group substituted with at least one nitrogen, a phenyl group substituted with at least one boron, aryl, substituted aryl, heteroaryl, four to six membered cycloalkyl, four to six membered heterocycloalkyl; R=H, C(O)$R_2$, $SO_2R_2$; $R_1$=H, C(O)$R_2$, $SO_2R_2$; $R_2$=Ethyl, methyl, isopropyl, n-propyl, t-butyl, n-butyl, $NH_2$, $NR_3R_4$, $R_3$, $R_4$=Ethyl, methyl, isopropyl, n-propyl, t-butyl, n-butyl, three to six membered cycloalkyl, Z=None In one aspect, the compound is selected from:

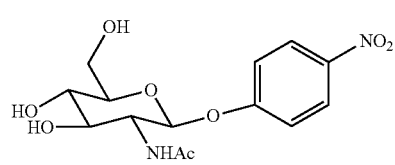

8

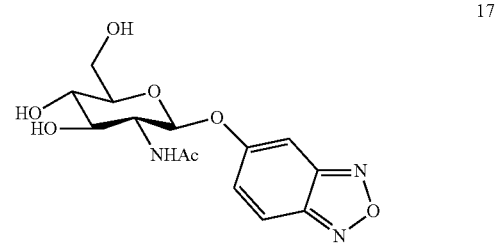

17

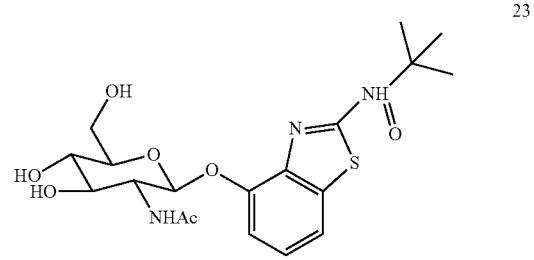

23

-continued

28
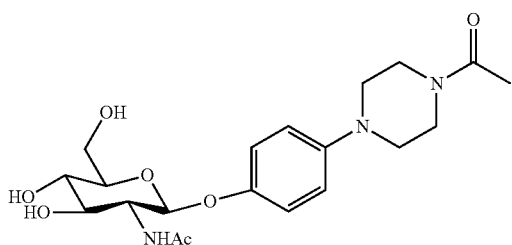

29
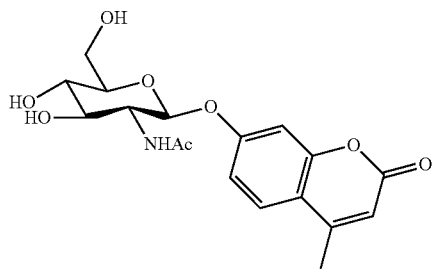

32
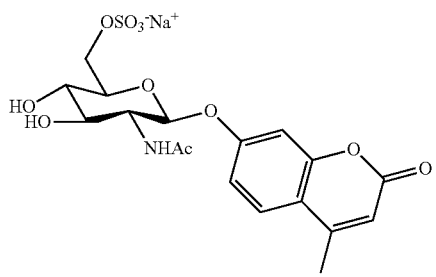

35
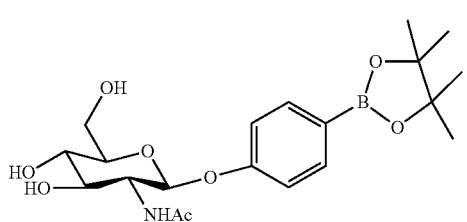

38
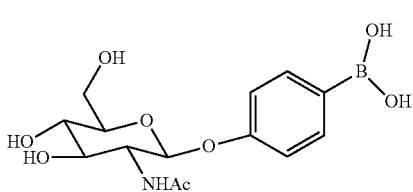

39
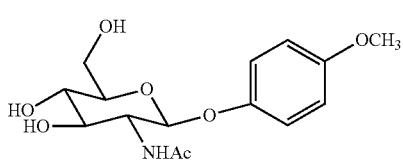

-continued

40
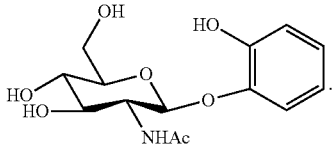

In another embodiment, the present invention includes a method of stimulating a Th1 immune response by agonizing TLR4, TLR6, TLR7 and TLR8, increasing phagocytosis of bacteria, or enhancing bacterial clearance comprising: identifying a subject in need of stimulating a Th1 immune response, increasing phagocytosis of bacteria, or enhancing bacterial clearance, and providing the subject with an effective amount of a compound with the Formula I:

Formula-I

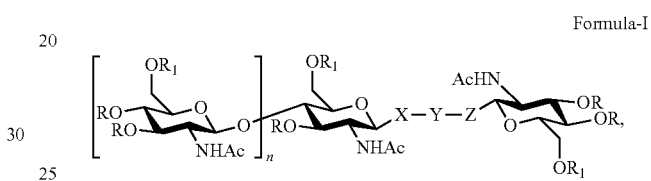

where n=0-5; X=NH, O, S, CH$_2$; Y=Phenyl, a phenyl group substituted with at least one methyl, a phenyl group substituted with at least one nitro, a phenyl group substituted with at least one nitrogen, a phenyl group substituted with at least one boron, aryl, substituted aryl, heteroaryl, four to six membered cycloalkyl, four to six membered heterocycloalkyl; R=H, C(O)R$_2$, SO$_2$R$_2$; R$_1$=H, C(O)R$_2$, SO$_2$R$_2$; R$_2$=Ethyl, methyl, isopropyl, n-propyl, t-butyl, n-butyl, NH$_2$, NR$_3$R$_4$, R$_3$, R$_4$=Ethyl, methyl, isopropyl, n-propyl, t-butyl, n-butyl, three to six membered cycloalkyl; Z=None, herein the amount is sufficient to stimulate the Th1 immune response, increase the phagocytosis of bacteria, virus or enhance bacterial or virus clearance. In one aspect, the bacterial clearance is to treat at least one of: systemic bacterial infection, a sepsis, a lung infection, an atopic dermatitis, or a skin wound infection. In one aspect, the viral clearance is to treat at least one of: systemic viral infection, a sepsis, a lung viral infection, an atopic dermatitis, or a skin wound infection. In certain aspects, the amount of the compound is formulated in an amount that is selected to either inhibit or activate the immune response as set forth in the tables hereinabove. In another aspect, the compound is a TLR2, TLR4, TLR7 and TLR8 inhibitor and downregulates IL-1β. In another aspect, the compound is a TLR9 inhibitor and down regulates IFN-α. In another aspect, the compound inhibits cancer cell proliferation and induces cancer cell death. In another aspect, the compound inhibits angiogenesis. In another aspect, the compound is provided in an amount sufficient to competitively inhibit inflammation and angiogenesis and protect from ocular angiogenesis related injury.

BRIEF DESCRIPTION OF THE DRAWINGS

For a more complete understanding of the features and advantages of the present invention, reference is now made to the detailed description of the invention along with the accompanying figures and in which:

FIG. 21 shows that compounds with TLR4 agonist activity decrease the CFU count of *Pseudomonas aeruginosa* in mice skin wound model.

FIGS. 22A, 22B, 22F, and 22G shows the total and neutrophil cell counts in bronchoalveolar lavage (BAL) fluid of LPS and hyperoxia-induced lung injury in mice treated with or without compounds 1 and 8. FIGS. 22C-E, 22H-J show ELISA assays for IL-6, IL-1β and IL-10 in BAL fluid of LPS and hyperoxia-induced lung injury in mice treated with or without compounds 1 and 8.

FIGS. 22A-J and 23A-F are expressed as mean±SE (n=6-8,*p<0.05 p<0.01 and *p<0.001). The statistical significance was assessed using a one-way ANOVA followed by Tukey post hoc analysis.

FIG. 24 shows compounds 1 and 8 prevent mouse pups from hyperoxia induced BPD via both intraperitoneal (IP) and intravenous (IV) route of dosing when formulated as saline solution.

FIGS. 25A to 25C show the improvement in chord length, septal thickness and radial alveolar count of mouse lungs in room air (RA), BPD and treated groups with either compound 1 compound 8 via IP injection. n=4-8, ***p<0.001, ANOVA.

FIG. 26 A-G shows treatment with 10 mg/kg of compound 8 decreases the inflammatory cytokines and chemokines (MIP-2, MCP-1, IL-17, IFN-Y, TNF-α, IL-1β, and IL-6) using ELISA.

FIG. 26H shows treatment with 10 mg/kg of compound 8 increase the anti-inflammatory cytokine IL-10 using ELISA. n=4-8, ***p<0.001, ANOVA.

FIG. 27A-C shows the slow drug release profile of PLGA encapsulated nanosuspensions 3NP, 8NP and 32 NP in saline solution.

FIG. 28 shows nanosuspension formulations 3NP, 8NP and 32NP prevent mouse pups from hyperoxia induced BPD via intranasal inhalation route of dosing.

DETAILED DESCRIPTION OF THE INVENTION

Figure 1:
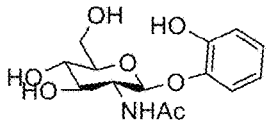
FIG. 1 is a table that shows compounds with TLR2 and TLR4 inhibitory and activating activity in THP-1 cells at low and high concentrations.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below.

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention includes novel compounds and/or amounts of the compounds, in which the immune-stimulating or inhibiting activity was assessed. Further, the immune-stimulating or inhibiting activity was also assessed for the structurally distinct TLR7/8 agonists/antagonists. The compounds of present innovation are small molecules that can modulate TLR pathways, upregulate IL-10 and downregulate inflammatory cytokines with therapeutic potential to treat BPD, ARDS, ILD, and COPD. The compounds of present innovation are small molecules that can inhibit TLR2 pathway with therapeutic potential to treat psoriasis, acne and other inflammatory diseases. The compounds of present innovation are small molecules that upregulate IL-10 with therapeutic potential to treat Rheumatoid Arthritis (RA) and osteoarthritis (OA). The compounds of present innovation are small molecules that can inhibit TLR4 pathway with therapeutic potential to treat lung cancer.

The present invention includes composition and methods that use carbohydrate derived toll like receptor antagonists to simultaneously suppress lung inflammation while improving pulmonary endothelial barrier function useful in BPD, ARDS, COPD, cystic fibrosis and pneumonia. One such compound has the following Formula (Formula I):

Formula-I

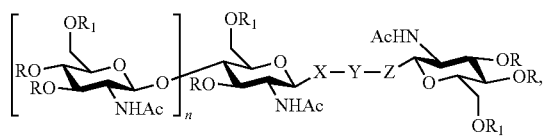

where n=0-5;

X=NH, O, S, CH$_2$;

Y=Four to six membered cycloalkyl, a phenyl group substituted with at least one methyl, a phenyl group substituted with at least one nitro, a phenyl group substituted with at least one nitrogen, a phenyl group substituted with at least one boron, aryl, substituted aryl, heteroaryl, cycloalkyl;

R=H, C(O)R$_2$, SO$_2$R$_2$;

R$_1$=H, C(O)R$_2$, SO$_2$R$_2$; and

R$_2$=Alkyl, substituted alkyl, aryl, substituted aryl, NHR$_3$

R$_3$=H, ethyl, methyl, isopropyl, n-propyl, t-butyl, n-butyl,

Z=NH, O, S, CH$_2$ or none.

The present inventors have made the following representative compounds:

1

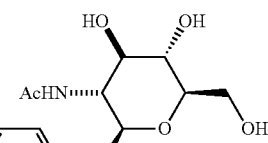

2

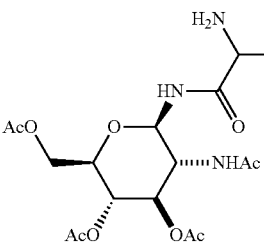

3

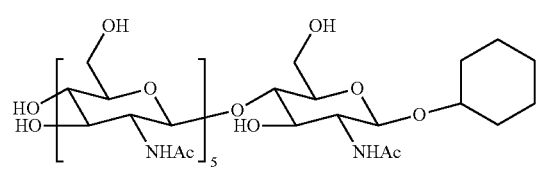

4

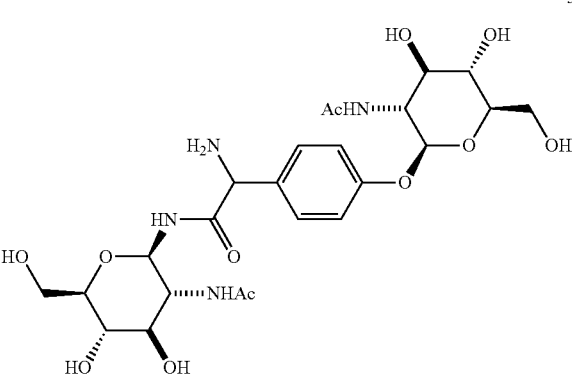

5

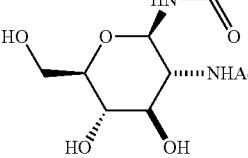

6

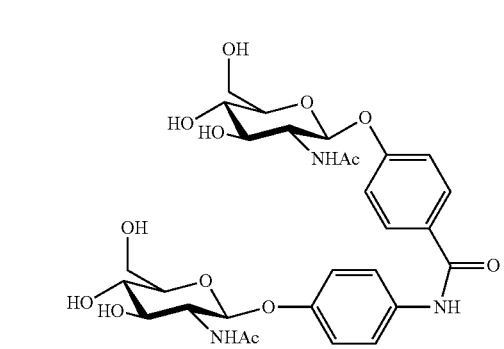

7

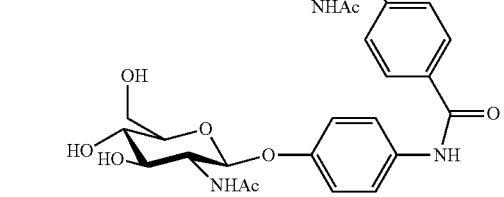

8

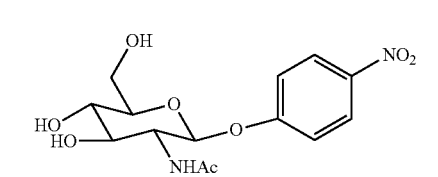

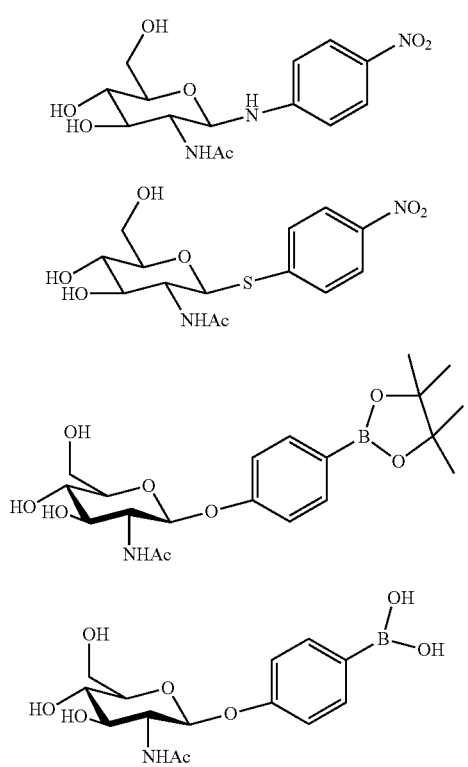

The compounds of the present invention find particular uses in the delivery of particles of low density and large size for drug delivery to the pulmonary system. Biodegradable particles have been developed for the controlled-release and delivery of compounds, such as those disclosed herein. Langer, R., Science, 249: 1527-1533 (1990).

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The present invention can be formulated for delivery to any part of the respiratory tract, e.g., Gonda, I. "Aerosols for delivery of therapeutic and diagnostic agents to the respiratory tract," in Critical Reviews in Therapeutic Drug Carrier Systems 6:273-313, 1990, relevant portions incorporated herein by reference. On one non-limiting example, the deep lung or alveoli are the primary target of inhaled therapeutic aerosols for systemic drug delivery of the present invention.

Inhaled aerosols have been used for the treatment of local lung disorders including asthma and cystic fibrosis and have potential for the systemic delivery of the compounds of the present invention. Pulmonary drug delivery strategies present many difficulties for the delivery of macromolecules, including: excessive loss of inhaled drug in the oropharyngeal cavity (often exceeding 80%), poor control over the site of deposition, irreproducibility of therapeutic results owing to variations in breathing patterns, the often too-rapid absorption of drug potentially resulting in local toxic effects, and phagocytosis by lung macrophages.

Considerable attention has been devoted to the design of therapeutic aerosol inhalers to improve the efficiency of inhalation therapies and the design of dry powder aerosol surface texture. The present inventors have recognized that the need to avoid particle aggregation, a phenomenon that diminishes considerably the efficiency of inhalation therapies owing to particle aggregation, is required for efficient, consistent deep lung delivery.

In one example for a formulation for pulmonary delivery, particles containing the active compound(s) of the present invention may be used with local and systemic inhalation therapies to provide controlled release of the therapeutic agent. The particles containing the active compound(s) permit slow release from a therapeutic aerosol and prolong the residence of an administered drug in the airways or acini, and diminish the rate of drug appearance in the bloodstream. Due to the decrease in use and increase in dosage consistency, patient compliance increases.

The human lungs can remove or rapidly degrade hydrolytically cleavable deposited aerosols over periods ranging from minutes to hours. In the upper airways, ciliated epithelia contribute to the "mucociliary escalator" by which particles are swept from the airways toward the mouth. It is well known that, in the deep lung, alveolar macrophages are capable of phagocytosing particles soon after their deposition. The particles containing the active compound(s) provided herein permit for an effective dry-powder inhalation therapy for both short- and long-term release of therapeutics, either for local or systemic delivery, with minimum aggregation. The increased particle size consistency is expected to decrease the particles' clearance by the lung's natural mechanisms until drugs have been effectively delivered.

PLGA encapsulated nanosuspension with extended drug release profile Nanoparticle formulation. Nanoparticle formulation can be carried out through a single or double emulsion technique. For example, for a single emulsion technique, 10 mg of compounds 0r was dissolved in 3 ml of chloroform containing 100 mg of PLGA to form an oil phase. This solution was then added dropwise into 20 ml of 5% PVA solution (water phase) and emulsified at 50 W for 5 minutes to form the compound loaded nanoparticles. The final emulsion was stirred overnight to allow solvent evaporation. The nanoparticles were washed and collected by ultracentrifugation and lyophilized before use.

For example of a double emulsion technique, 30 mg of poly(D,L-lactide-co-glycolide) (PLGA) were dissolved in 1 mL of chloroform at 4° C. Concurrently, 2 mL of a 2% w/v poly(vinyl alcohol) (PVA)/distilled deionized water solution was formed. Upon solubilization of the PVA in water, 1 mL of ethanol or methanol was added as a non-solvent to the PVA solution. The active compound was then added to the PVA/ethanol solution at a concentration of 1 mM and stirred. A stock solution of active agent, e.g., 10 mg/ml, is formed by the dissolution of curcumin into water under alkaline conditions using, e.g., 0.5 M NaOH. The active agent is added to the PLGA/Chloroform solution at concentrations of 0.5, 1.0, and 2.0 mg/mL per 150 microliters of aqueous volume. Formation of the primary emulsion is done by vortexing the active agent-PLGA/cholorform solution for 20 seconds, followed by tip sonication at 55 W for 1 minute on a Branson Sonifier model W-350 (Branson, Danbury, Conn.). The primary emulsion is then added to a BS3/PVA/ethanol solution to initiate formation of the secondary emulsion. Completion of the secondary emulsion is done through vortexing for 20 seconds and tip sonication at 55 W for 2 minutes. Stabile activated nanoparticles are then aliquoted into 1.5 mL Eppendorf tubes and centrifuged for 5 minutes at 18,000 g. The chloroform and residual PVA supernatant were aspirated off and particles were resuspended by tip sonication in, e.g., 1 mL of phosphate buffered saline (PBS) pH 7.2. Following resuspension, nanoparticles were placed at −80° C. for 1 hour and lyophilized overnight. Lyophilization can be carried out in an ATR FD 3.0 system (ATR Inc, St. Louis, Mo.) under a vacuum of 250 µT. After lyophilization nanoparticles are stored at 4° C. Upon use nanoparticles were weighed into eppendorf tubes and resuspended in 1 mL of PBS pH 7.4.

The present invention includes composition and methods that use carbohydrate derived toll like receptor 2 and 4 (TLR2/4) antagonists to suppress skin inflammation useful in Acne, and related bacterial infections. Examples of inflammatory conditions that can be treated with the present invention include sepsis, ankylosing spondylitis, psoriasis, psoriatic arthritis, Behcet's disease, arthritis, inflammatory bowel disease (IBD), and/or allergies. Some of these diseases are associated with a "cytokine storm", and can be treated with the composition provided in the amounts taught herein. Such compounds have the following Formula (Formula I):

Formula-I

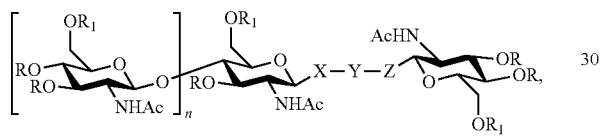

where n=0-5;
X=NH, O, S;
Y=Phenyl group substituted with at least one methyl, a phenyl group substituted with at least one nitro, a phenyl group substituted with at least one nitrogen, a phenyl group substituted with at least one boron, phenyl, aryl, substituted aryl, heteroaryl, cycloalkyl;
R=H, C(O)R$_2$, SO$_2$R$_2$;
R$_1$=H, C(O)R$_2$, SO$_2$R$_2$; and
R$_2$=Alkyl, substituted alkyl, aryl, substituted aryl, NHR$_3$
R$_3$=H, ethyl, methyl, isopropyl, n-propyl, t-butyl, n-butyl;
Z=NH, O, S, CH$_2$ or none.

The present inventors have made the following representative compounds:

3

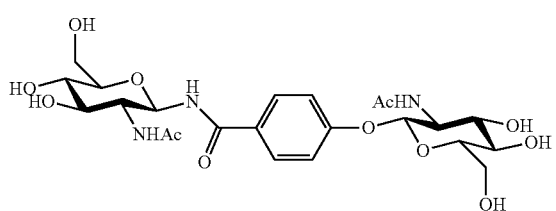

6

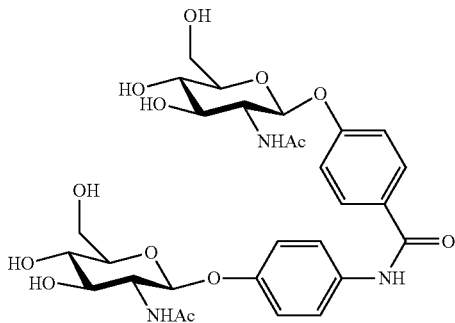

8

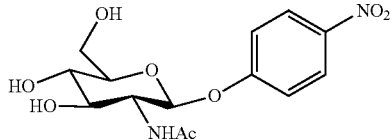

17

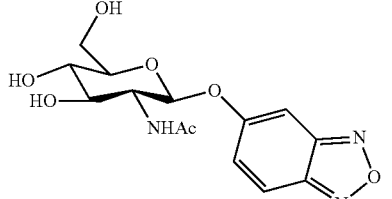

28

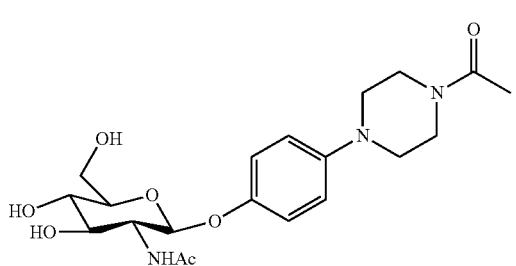

33

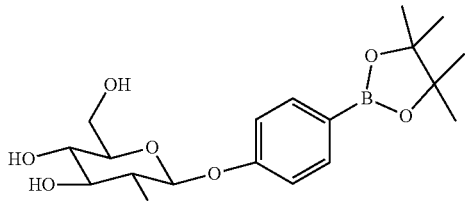

38

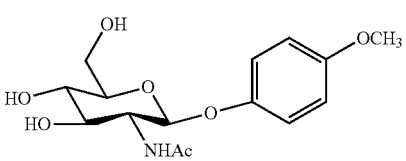

The present invention includes composition and methods that use carbohydrate derived toll like receptor agonists that stimulate Th1 immune response, increases the phagocytosis of the bacteria, enhances bacterial clearance useful in systemic bacterial infection, sepsis, lung infection, atopic dermatitis and skin wound infection. One such compound has the following Formula I:

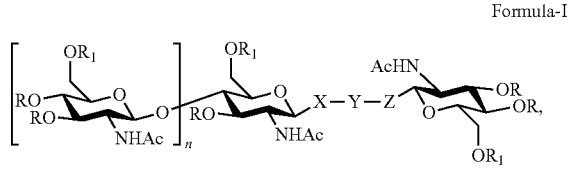

Formula-I where n=0-5;

X=NH, O, S;

Y=Phenyl group substituted with at least one methyl, a phenyl group substituted with at least one nitro, a phenyl group substituted with at least one nitrogen, a phenyl group substituted with at least one boron. Phenyl, aryl, substituted aryl, heteroaryl, cycloalkyl;

R=H, C(O)R$_2$, SO$_2$R$_2$;

R$_1$=H, C(O)R$_2$, SO$_2$R$_2$; and

R$_2$=Alkyl, substituted alkyl, aryl, substituted aryl, NHR$_3$

R$_3$=H, ethyl, methyl, isopropyl, n-propyl, t-butyl, n-butyl,

Z=None.

The present inventors have made the following representative compounds:

In some embodiments, the compounds of the present disclosure are incorporated into parenteral formulations. The term parenteral as used herein includes subcutaneous, intravenous, intramuscular, and intra-arterial injections with a variety of infusion techniques. Intra-arterial and intravenous injection as used herein includes administration through catheters. Preferred for certain indications are methods of administration that allow rapid access to the tissue or organ being treated, such as intravenous injections for the treatment of endotoxemia or sepsis.

The compounds of the present disclosure will be administered in dosages which will provide suitable inhibition or activation of TLR of the target cells; generally, these dosages are, preferably between 0.25-50 mg/patient, or from 1.0-100 mg/patient or from 5.0-200 mg/patient or from 100-500 mg/patient, more preferably, between 0.25-50 mg/patient and most preferably, between 1.0-100 mg/patient. The dosages are preferably once a day for 28 days, more preferably twice a day for 14 days or most preferably 3 times a day for 7 days.

Pharmaceutical compositions containing the active ingredient may be in any form suitable for the intended method of administration. Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2007; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000, and updates thereto; Martindale, The Extra Pharmacopoeia, Thirty-Second Edition (The Pharmaceutical Press, London, 1999); all of which are incorporated by reference, and the like, relevant portions incorporated herein by reference.

The present invention includes compositions and methods for making and generating aerosols for delivery of the active agents described herein at the specific doses. In one embodiment, the compounds are formulation to be aerosolized with an aerosol-generating device. A typical embodiment of this invention includes a liquid composition having predetermined physical and chemical properties that facilitate forming an aerosol of the formulation. Such formulations typically include three or four basic parameters, such as, (i) the active ingredient; (ii) a liquid carrier for the active ingredient; (iii) an aerosol properties adjusting material; and optionally, (iv) at least one excipient. The combination of these components provides a therapeutic composition having enhanced properties for delivery to a user by generating an inhalable aerosol for pulmonary delivery.

Aqueous suspensions of the compounds of the present invention contain the active materials in admixture with excipients suitable for the manufacture of aqueous suspensions. Such excipients include a suspending agent, such as sodium carboxymethylcellulose, methylcellulose, hydroxypropylmethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate.

The pharmaceutical compositions of the invention can be in the form of a sterile injectable preparation, such as a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenteral-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments the formulation comprises PLA or PLGA microparticles and may be further mixed with $Na_2HPO_4$, hydroxypropyl methylcellulose, polysorbate 80, sodium chloride, and/or edetate disodium.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders of the kind previously described.

It will be understood, however, that the specific dose level for any particular patient will depend on a variety of factors including the activity of the specific compound employed; the age, body weight, general health, and sex of the individual being treated; the time and route of administration; the rate of excretion; other drugs which have previously been administered; and the severity of the particular disease undergoing therapy.

In some embodiments the compositions of the present disclosure also contain from about 80% to about 99.5%, preferably from about 90 or 95% to about 98.5% of a compatible non-aqueous pharmaceutically acceptable topical vehicle. Some vehicles are described in U.S. Pat. No. 4,621,075, which is incorporated herein for this disclosure. Although it is preferred that these vehicles be free of water, the compositions of the present invention may contain up to about 5% water without significant adverse effects on the formation of the desired gels. These non-aqueous vehicle components are also well-known in the pharmaceutical arts, and they include (but are not limited to) short chain alcohols and ketones and emollients, such as hydrocarbon oils and waxes, lanolin and lanolin derivatives, silicone oils, monoglyceride, diglyceride, and triglyceride esters, fatty alcohols, alkyl and alkenyl esters of fatty acids, alkyl and alkenyl diesters of dicarboxylic acids, polyhydric alcohols and their ether and ester derivatives; wax esters and beeswax derivatives. Preferred vehicles incorporate methanol, ethanol, n-propanol, isopropanol, butanol, polypropylene glycol, polyethylene glycol and mixtures of these components. Particularly preferred vehicles include ethanol, n-propanol and butanol, especially ethanol. These preferred solvents may also be combined with other components, such as diisopropyl sebacate, isopropyl myristate, methyl laurate, silicone, glycerine and mixtures of these components, to provide non-aqueous vehicles which are also useful in the present invention. Of these additional components, diisopropyl sebacate is especially useful. In fact, preferred vehicles include mixtures of ethanol and diisopropyl sebacate in ratios, by weight, of from about 4:1 to about 1:4. Preferred vehicles contain from about 15% to about 35% diisopropyl sebacate and from about 65% to about 85% ethanol.

Compositions of the present invention may additionally contain, at their art-established usage levels, compatible adjunct components conventionally used in the formulation of topical pharmaceutical compositions. These adjunct components may include, but are not limited to, pharmaceutically-active materials (such as supplementary antimicrobial or anti-inflammatory ingredients, e.g., steroids) or ingredients used to enhance the formulation itself (such as excipients, dyes, perfumes, skin penetration enhancers, stabilizers, preservatives, and antioxidants). Examples of such agents include the pharmaceutically-acceptable acidic carboxy polymers, such as the Carbopol compounds commercially available from B. F. Goodrich Chemicals, Cleveland, Ohio.

In one embodiment, the compounds of the present invention may be formulate into a cream, lotion or gel packaged in a common trigger spray container will be firmly adhered to the area of interest as a regular cream does after it is sprayed out from the container. This is described in WO 98/51273, which is incorporated herein by reference. Accordingly, in one aspect, the present disclosure provides a pharmaceutical that can be incorporated into a non-aerosol spray composition for topical application, which comprises the compounds as described herein alone or in combination.

The compounds are present in an amount in the range of 0.1% to 20% or in some embodiments from 1 to 15% by weight, or in some embodiments from 2 to 10% by weight of cream, lotion or gel. The compounds of the present invention can be incorporated into a neutral hydrophilic matrix cream, lotion or gel. In a first preferred embodiment, the cream or lotion matrix for topical application is characterized by polyoxyethylene alkyl ethers. In a second preferred embodiment, the gel is characterized by high molecular weight polymer of cross-linked acrylic acid. Polyoxyethylene alkyl ethers are non-ionic surfactants widely used in pharmaceutical topical formulations and cosmetics primarily as emulsifying agents for water-in-oil and oil-in-water emulsions. It is characterized in this invention as a base for non-aerosol trigger sprayable cream or lotion. Cross-linked acrylic acid polymer (Carbomer) employed to form the gel is another object of this invention.

A particularly suitable base for non-aerosol spray is therefore a cream or lotion containing from 1 to 25% of polyoxyethylene alkyl ethers, 3 to 40% of humectant and 0.1 to 1% of preservative or preservatives and the balance to 100% being purified water. Aptly the polyoxyethylene alkyl ether can be one or any combination selected from the group consisting of polyoxyl 20 cetostearyl ether (Atlas G-3713), poloxyl 2 cetyl ether (ceteth-2), poloxyl 10 cetyl ether (ceteth-10), poloxyl 20 cetyl ether (ceteth-20), poloxyl 4 lauryl cetyl ether (laureth-4), poloxyl 23 lauryl cetyl ether (laureth-23), poloxyl 2 oleyl ether (oleth-2), poloxyl 10 oleyl ether (oleth-10), poloxyl 20 oleyl ether (oleth-20), poloxyl 2 stearyl ether (steareth-2), poloxyl 10 stearyl ether (steareth-10), poloxyl 20 stearyl ether (steareth-20), and poloxyl 100 stearyl ether (steareth-100). Suitable humectant can be one or any combination selected from the group consisting of propylene glycol, polyethylene glycol, sorbitol or glycerine. Suitable preservative is one or any combination selected from the group consisting of methylparaben, propylparaben, benzyl alcohol, benzoic acid, sodium benzoate, sorbic acid and its salt or phenylethyl alcohol.

Another suitable base for non-aerosol spray is a gel containing from 0.1 to 2.0% of Carbomer, 0.1 to 1% of alkaline solution, 3 to 40% of humectant and 0.1 to 1% of preservative or preservatives as and the balance to 100% being purified water. Aptly the Carbomer can be one or any combination selected from the group consisting of Carbomer 934, Carbomer 940 or Carbomer 941. The suitable humectant, preservative and purified water for the gel are same as that in the case or cream or lotion. Other sprayable formulations are described in US Pre-Grant Publication US2005/00255048, which is expressly incorporated herein by reference.

Ophthalmic formulation (topical and intravitreal dosing):

The compound of the invention will typically be a small percentage of the total ophthalmic composition. The compound of the invention will typically be at least 0.01 w/v %, more typically at least 0.1 w/v % and even more typically at least 0.5 w/v % of the ophthalmic composition. The compound of the invention will also typically be no greater than 5.0 w/v %, even more typically no greater that 3.0 w/v % and even more typically no greater than 1.5 w/v % of the ophthalmic composition.

The ophthalmic composition will also typically include a suitable ophthalmic vehicle for delivery of the compound to the eye. It is contemplated that the ophthalmic composition may be configured for topical or intravitreal application to the eye and the ophthalmic vehicle will likely be different depending upon the manner of application. Generally, for either topical or intravitreal applications, it is preferable that the ophthalmic composition be aqueous and include a substantial amount of water. Typically the composition will include at least 30 w/v %, more typically at least 80 w/v % and even more typically at least 90 w/v % water (e.g., purified water).

For intravitreal applications, particularly when the ophthalmic composition is applied to the eye with a syringe, the ophthalmic compositions may include, e.g., only, or consist essentially of, water and compound of the invention. For sustained drug release, PLGA or PLA macroparticle formulation of the compound of invention will be used as described by Shelke et al [Drug Deliv Transl Res. 2011, (1): 76-90]. Of course, the ophthalmic composition could include other ingredients as well such as $Na_2HPO_4$, hydroxypropyl methylcellulose, polysorbate 80, sodium chloride, and edentate disodium.

It could also be the case that the vehicle be only or consist essentially of water for a topical application, particularly if that topical application is performed shortly after water is combined with the test compound or the composition is packaged in a manner to prevent contamination. However, if the ophthalmic composition is to be applied as a multi-dose ophthalmic composition over an extended period of time (e.g., as drops from an eye-dropper once, twice, thrice or more per day for multiple days), the ophthalmic composition will likely include additional ingredients such as antimicrobial or preservative agents or systems, surfactants, buffering agents, tonicity agents, anti-oxidants, viscosity-modifying agents any combinations thereof or the like.

For topical application, the compositions of the present invention typically include antimicrobial agent. Potential antimicrobial agents include, without limitation, hydrogen peroxide, chlorine containing preservatives such as benzalkonium chloride or others. According to a preferred aspect, however, the composition of the present invention is entirely or substantially free of any non-polymeric quaternary anti-microbial agents such as benzalkonium chloride (BAK). Most preferred antimicrobial agent in the pharmaceutical composition includes polymeric quaternary ammonium compound.

As used herein, the phrase "substantially free of" as it refers to an ingredient of the ophthalmic composition means that it is contemplated that the ophthalmic composition can be either entirely devoid of that particular ingredient or includes only a nominal amount of that particular ingredient.

The polymeric quaternary ammonium compounds useful in the compositions of the present invention are those which have an antimicrobial effect and which are ophthalmically acceptable. Preferred compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.), which are expressly incorporated herein by reference. The most preferred polymeric ammonium compound is polyquaternium 1, otherwise known as POLYQUAD™ or ONAMERM™ with a number average molecular weight between 2,000 to 30,000. Preferably, the number average molecular weight is between 3,000 to 14,000.

The polymeric quaternary ammonium compounds are generally used in the suspensions of the present invention in an amount that is greater than about 0.00001 w/v %, more typically greater than about 0.0003 w/v % and even more typically greater than about 0.0007 w/v % of the suspension. Moreover, the polymeric quaternary ammonium compounds are generally used in the compositions of the present invention in an amount that is less than about 3 w/v %, more typically less than about 0.003 w/v % and even more typically less than about 0.0015 w/v % of the composition.

The antimicrobial agent of the composition of the present invention can additionally or alternatively include an antimicrobial system such as a borate/polyol complex system. As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts. Borate interacts with polyols, such as glycerol, propylene glycol, sorbitol and mannitol, to form borate polyol complexes. The type and ratio of such complexes depends on the number of OH groups of a polyol on adjacent carbon atoms that are not in trans configuration relative to each other. It shall be understood that weight/volume percentages of the ingredients polyol and borate include those amounts whether as part of a complex or not.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol.

When used, the borate/polyol complex antimicrobial system (i.e., the borate and polyol together) typically comprise at least 0.05 w/v %, more typically at least 0.5 w/v % and even possibly at least 1 or even at least 1.2 w/v % of the composition and also typically comprise less than 5 w/v %, more typically less than 2.2 w/v % and even possibly less than 1.6 w/v % of the composition. The borate to polyol ratio (weight to weight ratio) in the composition is typically between 1 to 1 and 1 to 10 and more typically is between 1 to 2 and 1 to 4 (e.g., about 1 to 3).

Tyloxapol, polysorbate-80 and polyoxyl hydrogenated castor oil are preferred surfactants. Tyloxapol is a highly preferred surfactant. When used, the surfactant is typically present in a concentration that is at least 0.01 w/v %, more typically at least 0.025 w/v % and even possibly at least 0.1 w/v % of the composition and also typically is less than 5 w/v %, more typically less than 2.0 w/v % and even possibly less than 1.0 w/v % of the composition.

The compositions of the present invention that are to be used for topical applications are typically formulated so as to be compatible with the eye. The ophthalmic compositions intended for direct application to the eye will be formulated so as to have a pH and tonicity that are compatible with the eye. The compositions will typically have a pH in the range of 4 to 9, preferably 5.5 to 8.5, and most preferably 5.5 to 8.0. Particularly desired pH ranges are 6.0 to 7.8 and more specifically 6.4 to 7.6. The compositions will have an osmolality of 200 to 400 or 450 milliosmoles per kilogram (mOsm/kg), more preferably 240 to 360 mOsm/kg.

Preferred compositions of the present invention are multi-dose ophthalmic compositions, for example, where the composition is in an eye dropper and can be administered as one or more drops once, twice, thrice or more times per day, topically to the eye. In that case, the compositions preferably have sufficient antimicrobial activity to allow the compositions to satisfy the USP preservative efficacy requirements, as well as other preservative efficacy standards for aqueous pharmaceutical compositions. There are two preservative efficacy standards in the European Pharmacopoeia "A" and "B".

The standards identified above for the USP 27 are substantially identical to the requirements set forth in prior editions of the USP, particularly USP 24, USP 25 and USP 26, each of which is incorporated herein by reference. As an added advantage, these ophthalmic compositions containing TLR4 antagonist compounds of the present invention are suitable for topical applications to the eye. The formulations described herein may also contain additional active ingredients, such as but not limited to anti-microbial agents as described above, pain reducing agents and the like.

Hyperoxia-induced inflammation is a cornerstone of the pathogenesis of BPD (Bhandari 2014) (i.e. secondary to production of reactive oxygen species or ROS) (Harijith and Bhandari 2016), as such, a variety of inflammatory molecules for, e.g., tumor necrosis factor-α (TNF-α), interleukin-1β (IL-1β), IL-6, inducible nitric oxide synthase (iNOS) have been implicated and/or associated with the development of BPD (Bhandari and Bhandari 2013). The toll-like receptor 4 (TLR-4) is one such signaling pathway involved in this process (Menden, Xia et al. 2016, Yao, Shi et al. 2017), especially with antenatal sepsis/inflammation leading to BPD (Glaser and Speer 2016).

Chitin and chitosan are high molecular weight oligosaccharides with diverse biological activities having hypocholesterolemic, antimicrobial, immunostimulating, antitumorigenic, accelerating calcium and iron absorption, anti-inflammatory, and antioxidant properties (Xia, Liu et al. 2011). These polysaccharides are known to activate alternate pathways and inhibit sepsis by gram-negative bacteria (Okawa, Kobayashi M Fau-Suzuki et al., Minami, Suzuki et al. 1998, Qiao, Bai et al. 2011, Solov, #039 et al. 2013). However, manipulation of chemical core structure of these high molecular weight polysaccharides to achieve optimum drug like properties have not been studied by any group.

The present invention provides for the first time a dual acting small molecule that can produce alternatively activated macrophages and competitively inhibit LPS induced inflammation leading to organ protection and limit tissue injury. One such compound is compound 1, which was designed and identified to bind differently to its target. Instead of binding to the TLR4-MD2 complex like other antagonists such as Eritoran (Kim, Park et al. 2007), it binds directly to the active site of TLR4, thus inhibiting the downstream components. In addition, a novel series of compounds were designed and identified by SAR study such as Compounds 1, 3, 8 and 32 that also inhibit TLR4 in an in vivo model system using neonatal pups with BPD.

Chitin and chitosan have excellent properties for ideal drugs delivery (Janes, Fresneau et al. 2001, Williams, Lansdown et al. 2003, Li, Zhuang et al. 2009). LMW chitosan are natural molecules with no systemic toxicity. These are excellent candidates for drug-like target with the ability to be delivered as polymeric nanoparticles The in silico model of binding of N-hexaacetyl chitohexaose to the TLR4 active site was presented in the inventors previous publication (Panda, Kumar et al. 2012). Based on preliminary results and molecular docking, the inventors designed and synthesized several compounds as shown above and screened in in vitro assays. Based on the optimal physicochemical property, the inventors have selected compounds 1, 3, 8 and 32 to be studied in the developmentally-appropriate hyperoxia-exposed BPD mouse model.

The novel compounds are innovative in both concept and methodology. The multifactorial pathology of ARDS cannot be counterattacked completely by monotherapy; hence, the present inventors developed a bifunctional molecule that will up-regulate the compensatory anti-inflammatory cytokine IL-10 via binding to TLR4 and improving pulmonary barrier function as well as suppress the inflammatory cytokines (TNF-α, IL-1β, IL-6) inflammation. Further, as a result of structure activity relationship (SAR) approach used herein, and the synthesizing a variety of compounds based on Formula I, the skilled artisan can perform systematic structural modifications of this amino sugar series of compounds to produce additional efficacious analogs. Thus, the present invention incudes SAR composition and methods for creation of derivatives of 1-O-substituted aminosaccharide analogs that have activity against hyper-inflammation caused in sepsis, ARDS as well as in ALI. FIG. 1 is a table that shows compounds with TLR2 and TLR4 inhibitory and activating activity in THP-1 cells at low and high concentrations.

Figure 2:
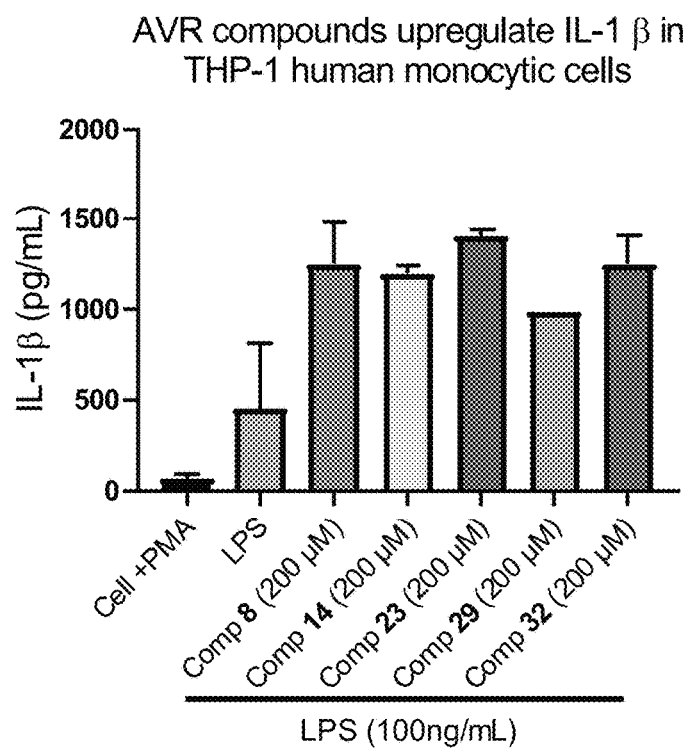
FIG. 2 shows that compounds with TLR4 agonist activity upregulate the inflammatory cytokine IL-1β indicating stimulation of innate immunity.
Figure 3:
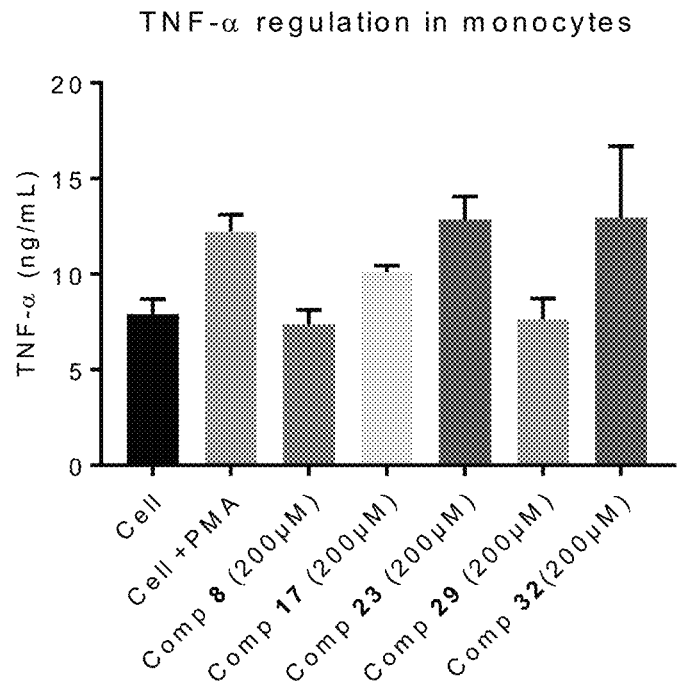
FIG. 3 shows compounds with TNF-α upregulating activity.

Compounds 1, 2, 3, 6, 7, 8, 14, 32 and 35 are potent TLR2/4 antagonists whereas compounds 17, 23, 28, –29, 30, 38, 39 and 40 are TLR4 agonists as shown in Table-1. Compounds 8, 32 and 35 shows concentration dependent TLR4 modulatory activity. Compounds with TLR4 agonist activity shows upregulation of inflammatory cytokines IL-1β (FIG. 2) and TNF-α (FIG. 3) indicating stimulation of innate immunity and shifting the Th1:Th2 ratio towards Th1. This class of TLR4 agonists could be useful as vaccine adjuvants, and in retract sepsis where the patient's immune system is suppressed and they are prone to secondary infection. Boosting the immune system will be useful with cancer as well as HIV patients where their innate immunity is compromised.

Figure 4:
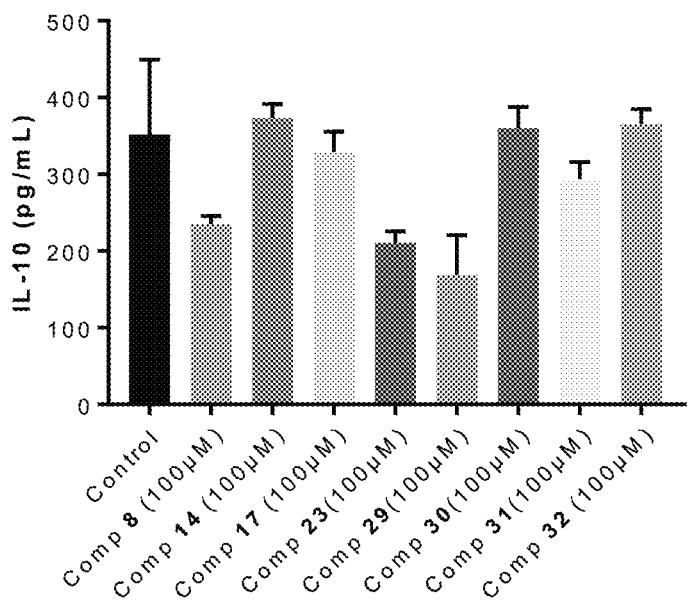
FIG. 4 shows the modulation of IL-10 production in monocytes.

When THP-1 (human monocytic) cells were treated with 100-200 µM of compounds 8, 14, 17, 23, 29, and 32, they produced an increased IL-1β and TNF-α response, decreased anti-inflammatory cytokine IL-10 (FIG. 4).

Figure 7:
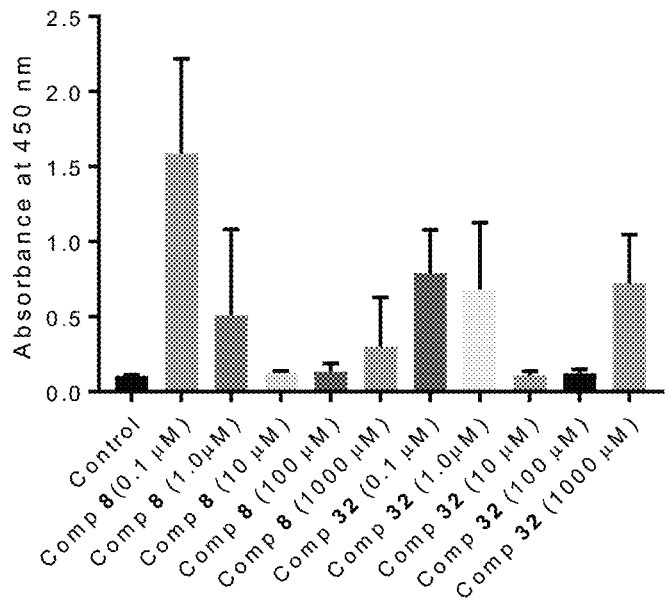
FIG. 7 shows compounds 8 and 32 with concentration dependent regulation of IL-10 production in monocytes.
Figure 8:
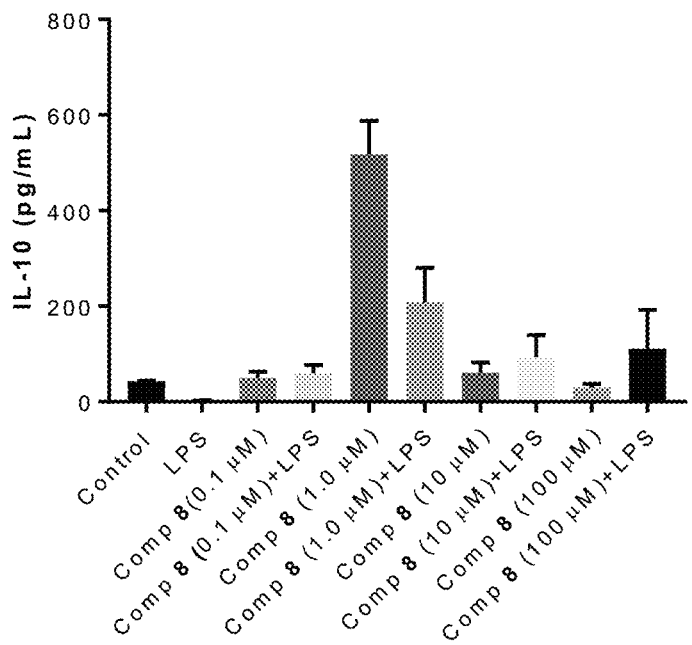
FIG. 8 shows compounds 8 with concentration dependent modulation of IL-10 production in monocytes in response to TLR4 ligand LPS.

Surprisingly, two of these compounds 8 and 32 dose dependently increase (stimulate Th2 macrophages at 0.1-1.0 µM concentration) or decrease (at 10-100 µM concentration) of IL-10 production in human peripheral blood monocytes after 48 h (FIGS. 7 and 8).

Figure 18:
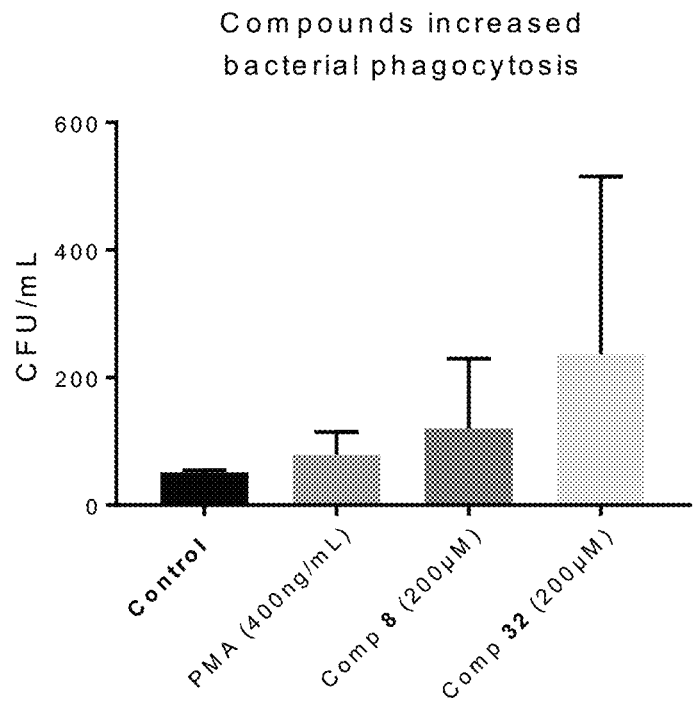
FIG. 18 shows treatment with AVR compounds increased the phagocytosis of *Pseudomonas aeruginosa* in THP-1 cells.
Figures 19, 20:
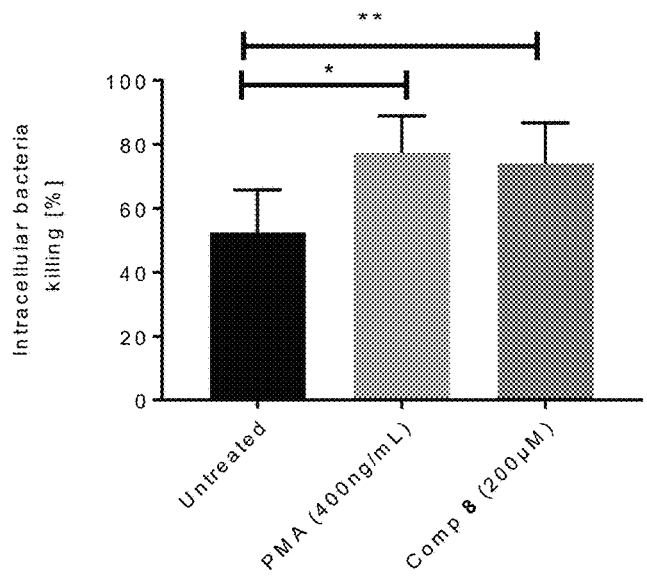
FIG. 19 shows treatment with compound 8 increased the intracellular killing of *Pseudomonas aeruginosa* in THP-1 cells.
FIG. 20 is a table that shows minimum inhibitory and fractional inhibitory concentrations of the compounds and synergistic activity with colistin against both gram positive and gram-negative bacteria.

Two of these compounds 8 and 32 stimulated monocyte differentiation into macrophages, increased phagocytosis of *Pseudomonas aeruginosa* (FIG. 18) and increased intracellular killing of bacteria (FIG. 19). These compounds have potential to be used as vaccine adjuvants and in combination with existing antibiotic for prophylactic treatment such as in cystic fibrosis patients.

Figure 5:
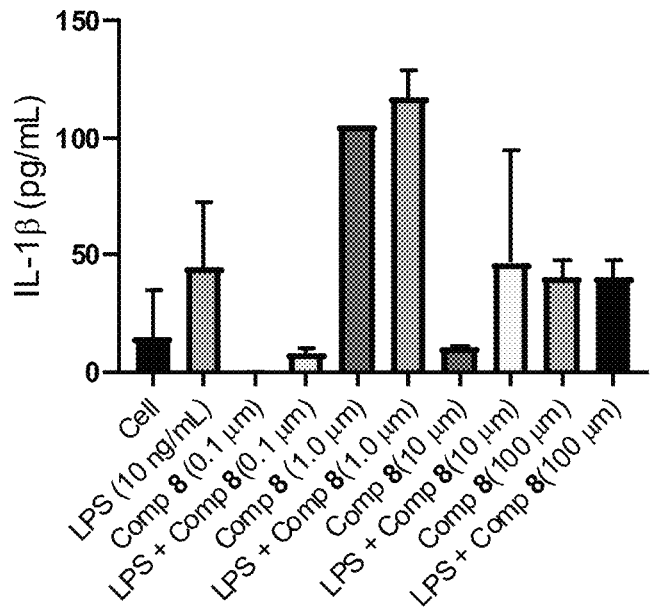
FIG. 5 shows compounds 8 with concentration dependent modulation of IL-1β production in monocytes in response to TLR4 ligand LPS.

Compound 8 modulates the TLR4 activities in a concentration dependent manner. At low concentrations (0.1 µM to <1 µM), compound 8 alone or in combination with TLR4 ligand LPS downregulate the IL-1β protein level in hPBMC after 24 h as detected by ELISA demonstrating TLR4 antagonist activity. However, at concentration of 1.0 µM, compound 8 alone and in combination with LPS significantly stimulated the production of IL-1β indicating TLR4 agonist activity (FIG. 5).

Figure 6:
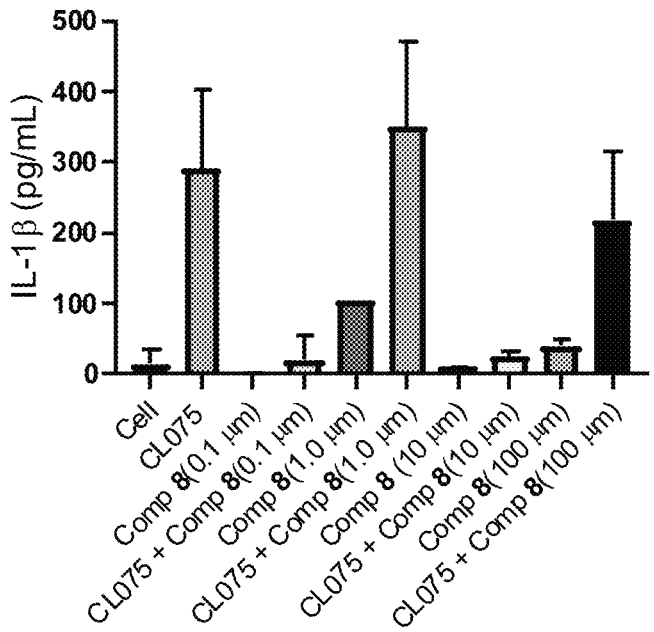
FIG. 6 shows compounds 8 with concentration dependent modulation of IL-1β production in monocytes in response to TLR7/8 ligand CL075.

Compound 8 modulates the TLR7/8 activities in a concentration dependent manner. At low concentrations (0.1 µM to <1 µM), compound 8 alone or in combination with TLR7/8 ligand CL075 downregulate the IL-1β protein level in hPBMC after 24 h as detected by ELISA demonstrating TLR7/8 antagonist activity. However, at concentration of 1.0 µM, compound 8 alone and in combination with CL075 significantly stimulated the production of IL-1β indicating TLR7/8 agonist activity (FIG. 6).

Figure 10:
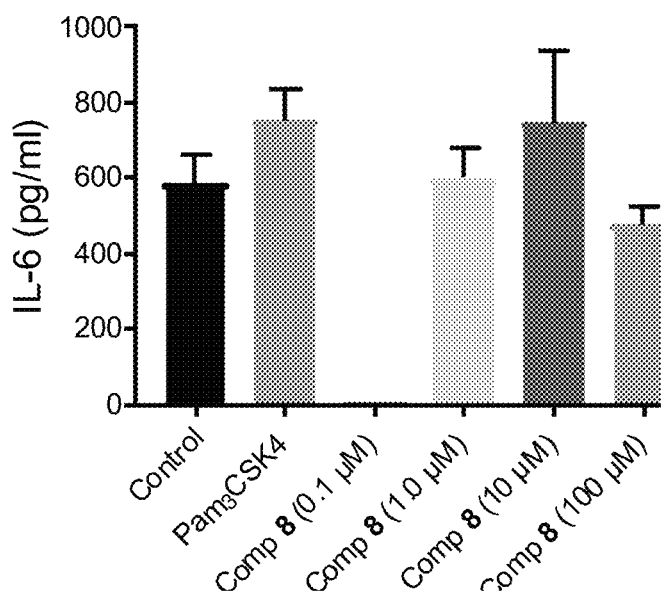
FIG. 10 shows compounds 8 with concentration dependent modulation of IL-6 production in monocytes in response to TLR1/2 ligand $Pam_3CSK4$.

Compound 8 modulates the TLR1/2 activities in a concentration dependent manner. At low concentrations (0.1 µM to <1 µM), compound 8 in combination with TLR1/2 ligand Pam₃CSK4 downregulate the IL-6 protein level in hPBMC after 24 h as detected by ELISA demonstrating TLR1/2 antagonist activity. However, at concentrations of 1.0, 10 and 100 µM, compound 8 in combination with CL075 significantly stimulated the production of IL-6 indicating TLR1/2 agonist activity (FIG. 10).

Figure 9:
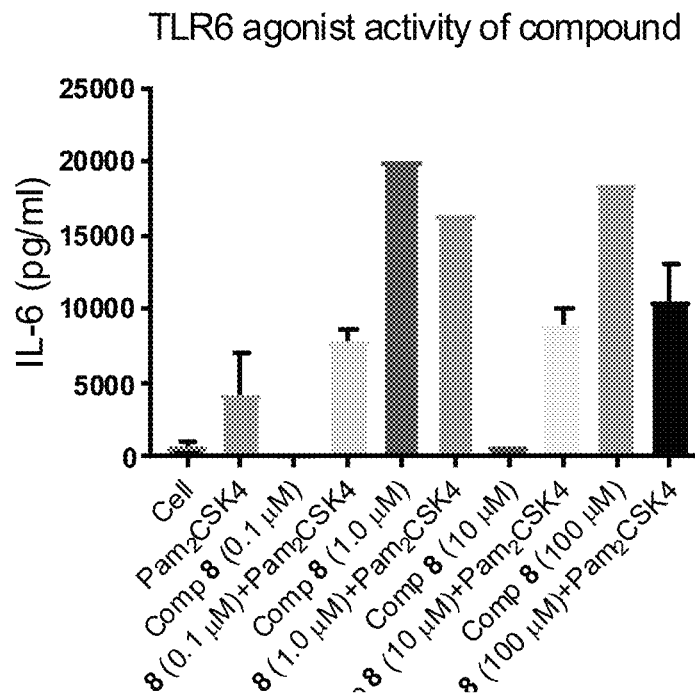
FIG. 9 shows compounds 8 upregulates IL-6 production in monocytes in response to TLR6 ligand $Pam_2CSK4$.

Compound 8 stimulates the TLR6 activities and upregulates the production of IL-6 cytokine in combination with TLR6 ligand Pam₂CSK4 in hPBMC after 24 h of treatment as detected by ELISA (FIG. 9).

Figure 11:
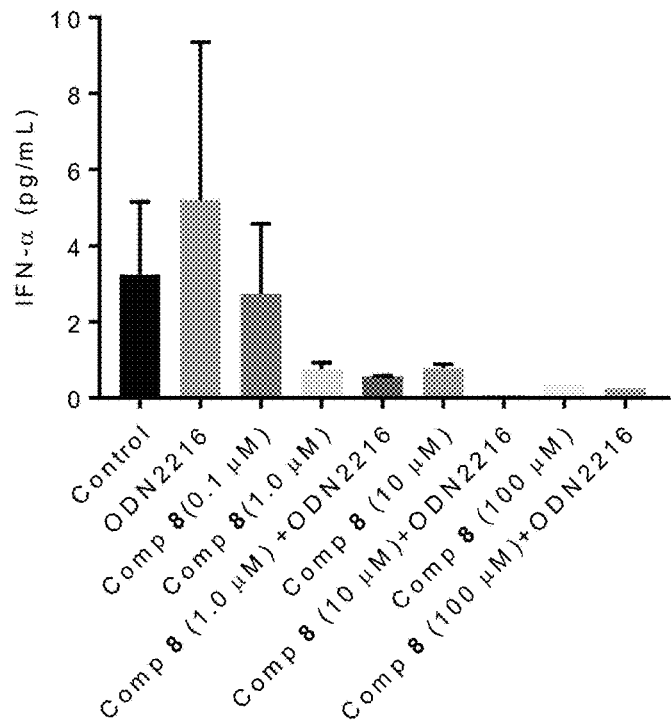
FIG. 11 shows compounds 8 downregulates the production of IFN-α in monocytes in response to TLR9 ligand ODN2216.

Compound 8 antagonizes the TLR9 activities and downregulates the production of IFN-α in combination with TLR9 ligand ODN2216 in hPBMC after 48 h of treatment as detected by ELISA (FIG. 11).

Figure 12:
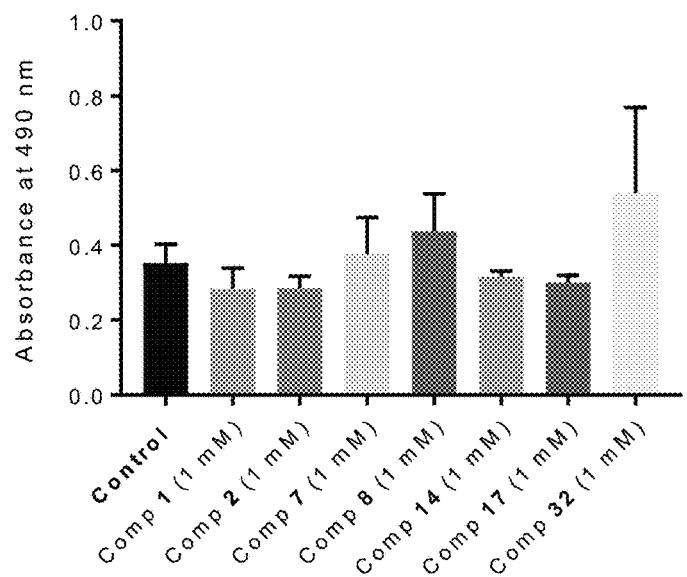
FIG. 12 shows no cytotoxicity of AVR compounds in human peripheral blood (hPBMC) monocytes.

Compounds 1, 2, 7, 8, 14, 17 and 32 were tested for cytotoxicity in hPBMC at concentrations of 0.1, 1.0, 10, 100 and 1000 µM. The cells were treated with compounds and incubated for 24 h. Cell viability was assessed using MTT cell proliferation kit (Promega). All the compounds were not toxic to hPMBC (FIG. 12).

Figure 13:
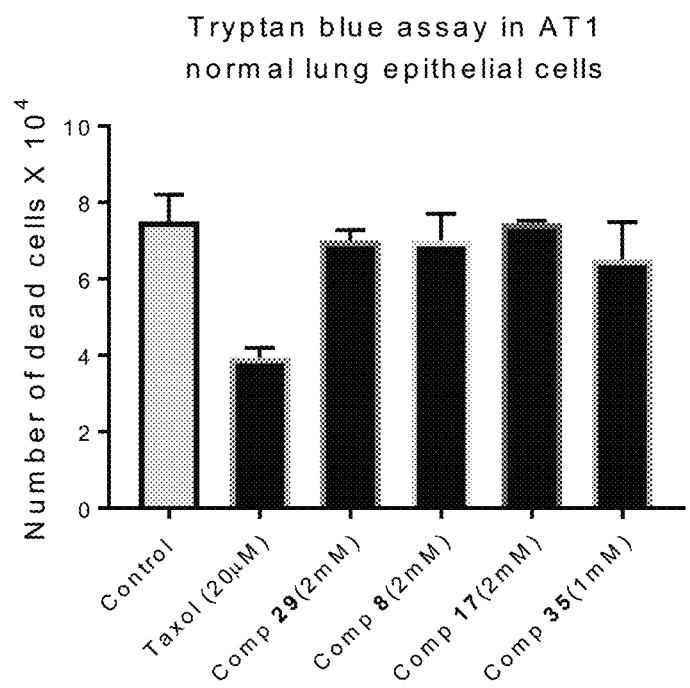
FIG. 13 shows no cytotoxicity of AVR compounds in human primary Alveolar Type-I (AT-1) lung epithelial cells.

Compounds 8, 17, 29 and 35 were tested for cytotoxicity in normal lung epithelial cells (AT-1) at concentrations of 1 mM and 2 mM. The cells were treated with compounds and incubated for 48 h. Cell viability was assessed using tryptan blue live/dead assay. All the compounds were not toxic to AT1 cells where the positive control Taxol was toxic (FIG. 13).

Figure 14:
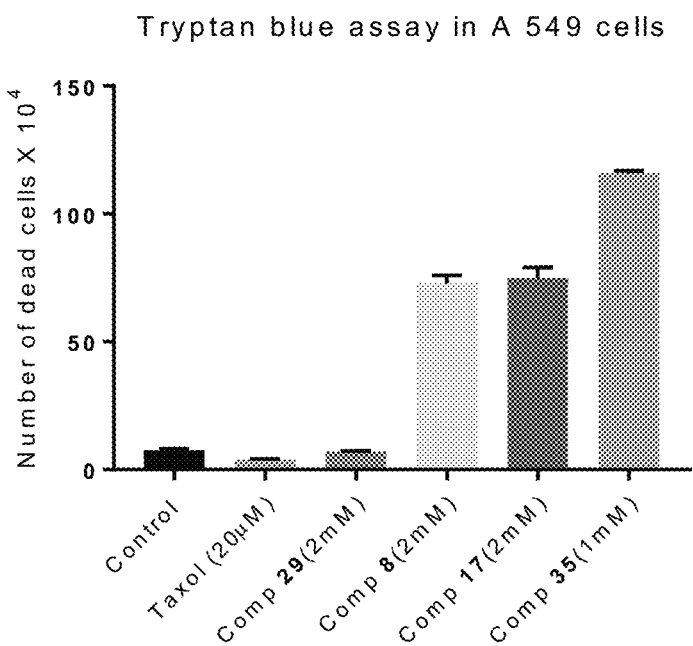
FIG. 14 shows the cytotoxicity activity of AVR compounds in human lung adenocarcinoma A549 cells.

Compounds 8, 17, 29 and 35 were tested for their cytotoxicity activity in A549 lung adenocarcinoma cells at concentrations of 1 mM and 2 mM. The cells were treated with compounds and incubated for 48 h. Cell viability was assessed using tryptan blue live/dead assay. Compounds 8, 17 and 35 were toxic to A549 cells and were superior in killing cancer cells where a standard anti-cancer drug taxol was not (FIG. 14).

Figure 15:
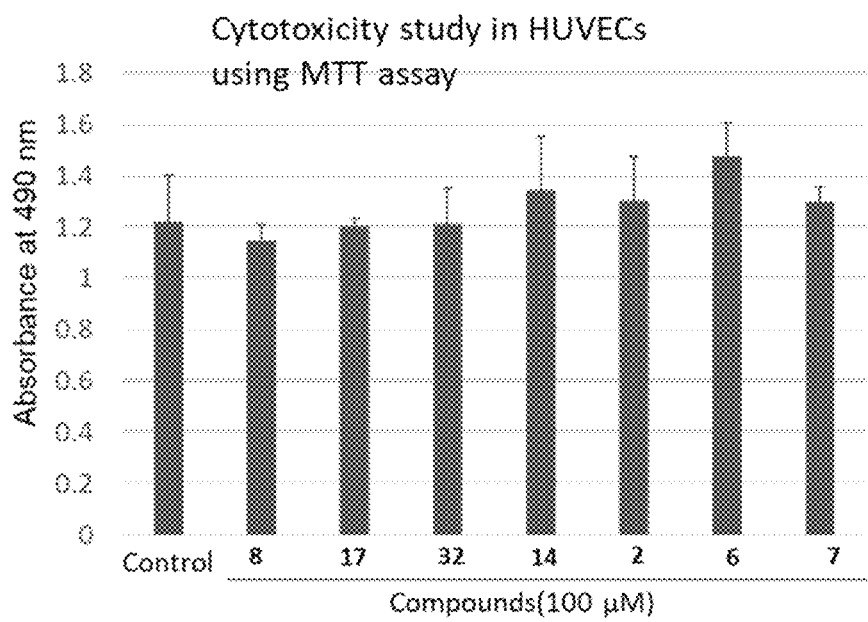
FIG. 15 shows no cytotoxicity of AVR compounds in human umbilical vascular endothelial cells (HUVECs).

Selected TLR2/4 antagonist compounds 2, 6, 7, 8, 14, 17 and 32 were evaluated for cytotoxicity in HUVECs at 100 µM concentration. The cells were treated with compounds and incubated for 24 h. Cell viability was assessed using MTT cell proliferation kit (Promega). All the compounds were not toxic to HUVECs (FIG. 15).

Figure 16:
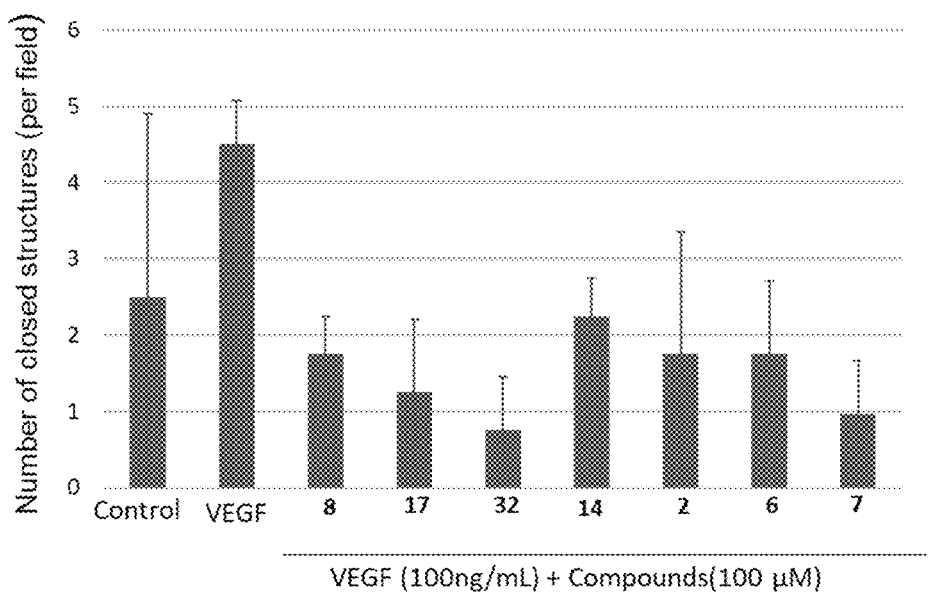
FIG. 16 shows AVR compounds decrease VEGF induced increase in number of closed tube structures in HUVECs.
Figure 17:
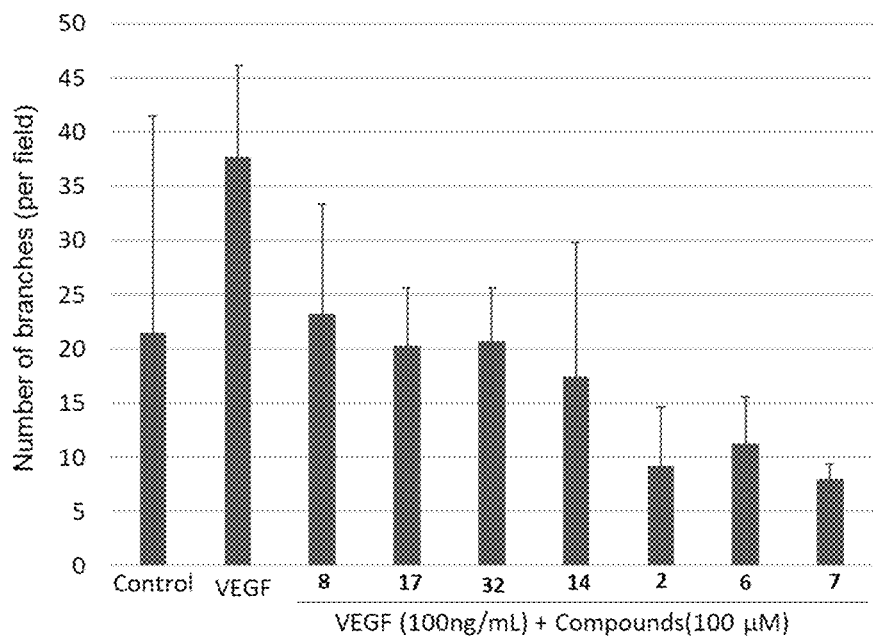
FIG. 17 shows AVR compounds decrease VEGF induced increase in number branched tube structures in HUVECs.

Selected TLR2/4 antagonist compounds 2, 6, 7, 8, 14, 17 and 32 were evaluated for anti-angiogenic activity using the Tube Formation kit (Cat #3470-096-K). VEGF (100 ng/mL) was used as positive control. All of the compounds significantly deceased the VEGF induced tube formation as shown in FIGS. 16 and 17. These compounds have potential applications in diseases associated with pathological angiogenesis such as solid tumor, retinitis of prematurity, diabetic retinopathy as well as AMD.

When screened against selected gram negative (*E. coli, P. aeruginosa, A. baumanni*) and gram positive (MRSA) bacteria (using broth dilution assay), compounds 1 and 8 showed bactericidal activity with $MIC_{90}$ of 50-200 mg/L. Unexpectedly, in combination with standard antibiotic colistin, the MIC of the compounds was lowered to 3.1-6.25 µg/mL (FIG. 20) demonstrating synergism and additive activity.

Based on the anti-inflammatory and antimicrobial activity, compounds 1 and 8 were evaluated in a murine study of skin wound infection. Both compounds 1 and 8 effectively closed *P. aeruginosa* (ATCC-10145 GFP) infected skin wounds in C57BL6 mice (n=4) when administered topically at a dose of 100 μM and decreased the CFU in tissues (FIG. 18).

Five groups of C57BL/6 mice (8-10 weeks old, n=4) were wounded on the dorsal surface. 25 ul containing $10^6$ CFU/mL P. aeruginosa in a PBS suspension were pipetted onto the wound and allowed to absorb for at least 3 min. Mice were then treated with either 25 μl of Colistin (4 μg/ml), or compounds 1 or 8 (100 μg/ml). Subsequently and for the next 13 days, infected wounds were treated each alternate day with colistin, or with test compounds. At day 13, the wounds of P. aeruginosa+colistin and P. aeruginosa+compound 1 or 8 groups reached complete closure, whereas eschars of P. aeruginosa+vehicle wounds were not.

Following infection with P. aeruginosa (13 days post infection), bacterial numbers from untreated control animals were significantly different from counts obtained from animals treated with P. aeruginosa+colistin and P. aeruginosa+compound 1. Compound 8 also showed statistically significant reduction in bacterial counts compared to control (FIG. 21).

Histological examination of H&E stained wounds isolated at day 13 post-injury indicated that P. aeruginosa+vehicle injected wounds presented a delayed healing phenotype with incomplete re-epithelialization and presence of focal inflammation at the wound bed. Re-epithelialization and granulation tissue were significantly enhanced in P. Aeruginosa (PA)+Colistin and PA+compound 1 group compared to controls (p=0.050). The same trend was observed for the compound 8 group, though differences were borderline non-significant (p=0.073). Along with that less focal inflammation is observed in compound treated groups vs PA group.

Two of the TLR4 modulators compounds 1 and 8 were delivered via Intraperitoneal (IP) injection and ameliorated LPS- and hyperoxia-induced lung inflammation in mice.

Male C57BL/6 mice (Jackson Laboratories,) 12-15 weeks old, 25-28 gms, housed up to 5 per cage were used.

Hyperoxia induced ALI model: The ARDS model consists of exposing adult mice in 100% oxygen for 48 h followed by injecting with test compounds. Adult mice (N=5) were housed in plexi chamber with a constant and continuous supply of 100% oxygen for 48 h. After 4 h of oxygen exposure, compounds 1 and 8 were injected, IP (10 mg/kg); the mice were returned back to the cages and again taken out for a 2nd dose of repeat injection after 12 h. The mice were sacrificed after 48 h to harvest lung tissues and collect (BAL) fluid.

LPS-induced ALI model: Adult mice (N=5) were injected with a single dose of LPS (100 μg/mice in 100 μl volume, intra tracheal) followed by IP. injection of compounds 1 or 8 (10 mg/kg body weight) at 4 h and 12 h post LPS injection, and then sacrificing the mice after 24 h to harvest lung tissues and collect BAL fluid. The lungs were sectioned for histopathological assessment after H/E staining while the BAL fluid was used to detect total cell counts (neutrophils and macrophages) and measure protein (that exudes by leakage). Lung lysates were made to quantify certain markers by western blotting after treatment with compounds 1 or 8, following hyperoxia exposure. Both the compounds demonstrated significant protection against both hyperoxia and LPS induced lung injury in the mouse models mimicking ARDS and bacterial pneumonia conditions, respectively.

FIGS. 22A, 22B, 22F, and 22G shows the total and neutrophil cell counts in bronchoalveolar lavage (BAL) fluid of LPS and hyperoxia-induced lung injury in mice treated with or without compounds 1 and 8. FIGS. 22C, 22D, 22E, 22H, 22I, and 22J show ELISA assays for IL-6, IL-1β and IL-10 in BAL fluid of LPS and hyperoxia-induced lung injury in mice treated with or without compounds 1 and 8.

Figure 23A:
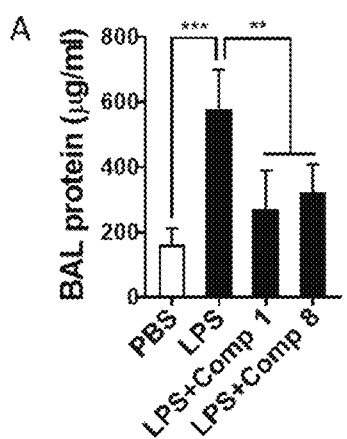
FIGS. 23A, 23B, 23D, and 23E shows pulmonary edema (as measured by total protein in the BAL fluid and Evans Blue dye concentration) in the lungs.
Figure 23B:
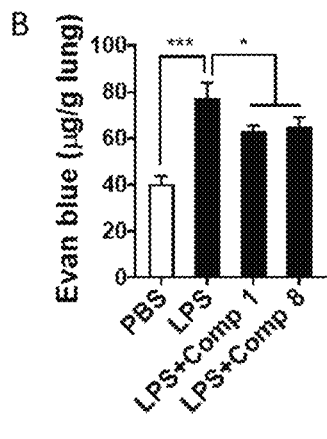
Figure 23C:
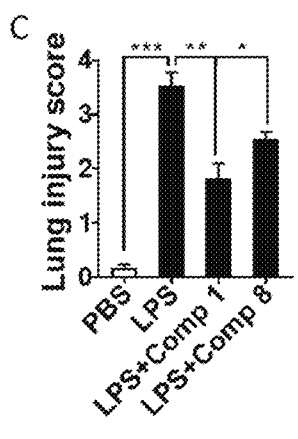
FIGS. 23C and 23F show lung injury score in mice treated with compounds 1 and 8 or controls. Data in both
Figure 23D:
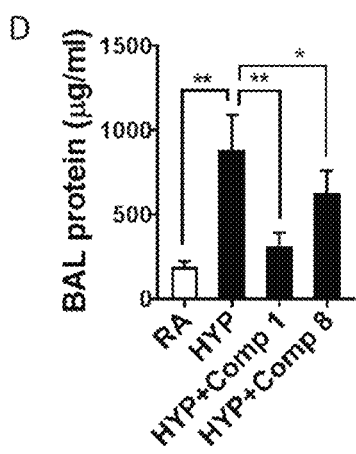
Figure 23E:
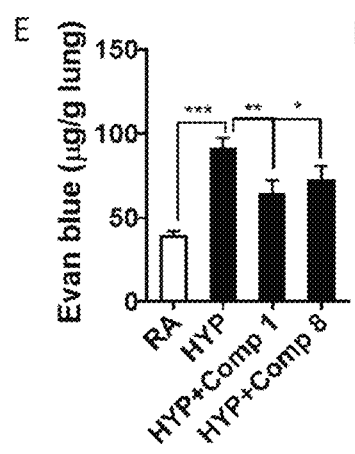
Figure 23F:
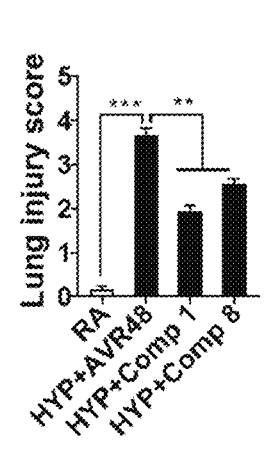

FIGS. 23A, 23B, 23D, and 23E shows pulmonary edema (as measured by total protein in the BAL fluid and Evans Blue dye concentration) in the lungs. FIGS. 23C and 23F show lung injury score in mice treated with compounds 1 and 8 or controls. Data in both FIGS. 22 and 23 are expressed as mean±SE (n=6-8,*p<0.05 p<0.01 and *p<0.001). The statistical significance was assessed using a one-way ANOVA followed by Tukey post hoc analysis.

Western blotting results showed junctional adherent proteins VE-cadherin, β-Catenin, and Src in the lungs in mice treated with compounds 1 or 8 or controls.

Next, the inventors demonstrated the protective effects of the compounds 1, 3, 8 and 32 in BPD lung injury model. To prove the concept and demonstrate the feasibility, the inventors tested compounds 1, 3, 8 and 32 in a mouse model of BPD and all compounds prevent lung injury in neonatal pups with BPD. Neonatal mice and humans undergo similar stages of lung development but differ with respect to the duration of each stage and its temporal relationship to gestational age. The lungs of the mouse born at term are in the saccular stage and are surfactant sufficient; this can be considered somewhat akin to a human preterm neonate in the same stage of lung development that has been exposed to a full complement of antenatal steroids (which is known to enhance surfactant production). In terms of mimicking the human condition, the most successful hyperoxia models are those that limit exposure to hyperoxia to the saccular stage of pulmonary development. The mouse BPD model involves exposing newborn mice (postnatal day 1 or PN1) to 100% oxygen till PN4 followed by recovery in room air (RA) for another 10 days. This model recapitulates the human model in the clinical scenario.

Each of the compounds 1 or 8 was injected intra-peritoneally (IP) or intravenously (IV) to newborn pups on PN2 and PN4 at a dose of 5 mg/kg or 10 mg/kg (FIG. 24). After the recovery period, their lungs were harvested and processed for quantitative PCR, western blotting, histopathology and ELISA.

Inflammatory cytokines are decreased in lung tissue and serum after compounds 1 and 8 injections. As inflammation is the characteristic feature of BPD, the inventors next determined if the compounds could suppress inflammation or not. By ELISA it was confirmed that there was decreased expression of several pro-inflammatory cytokines with concomitant increase in the anti-inflammatory marker, IL-10 after compound 8 treatment (FIGS. 26 A-H).

To test the feasibility of intranasal delivery of the compounds with a sustained drug release profile and avoid whole body exposure, each of the compounds 3, 8 or 32 was encapsulated in PLGA nanoparticles. The size of the nanoparticles was between 350-400 nm. The drug loading and drug release profile was determined using our earlier published method (Le et al, Nat Sci, Rep, 2017). The nanosuspension of the present invention showed slow drug release profile (FIGS. 27 A-C).

Each of the compounds 3, 8 or 32 encapsulated in PLGA nanoparticles referred as 3NP, 8NP and 32NP was instilled intranasally (IN) as nanosuspension to newborn pups on PN2 and PN4 at different doses (FIG. 28). After the recovery period, their lungs were harvested and processed for quantitative PCR, western blotting and histopathology and ELISA.

Lung morphology is improved in neonatal pups with BPD after treatment with test compounds. BPD is characterized by large simplified alveoli, inflammation, increased cell death, decreased cell proliferation, dysmorphic capillary configuration, and variable interstitial cellularity and/or fibroproliferation. The lung architecture is restored after treatment with compounds 3, 8 and 32 both in saline and nanosuspension formulation via IV and IN routes respectively. This is determined by measuring the alveolar chord length, septal thickness and radial alveolar count (RAC). In BPD, the alveolar area increases which is characterized by increase in the diameter of the alveolar sacs, the septa become thickened (thus interfering in gaseous exchange) and the RAC, a parameter used to assess the complexity of terminal respiratory unit by pulmonologists, decreases as a result of arrested lung development. All these changes are reverted to parameters of normal healthy lungs after treatment with the test compounds (FIGS. 25A-C).

Activation of Toll-Like Receptor 2 in Acne triggers inflammatory cytokine responses (J Immunol. 2002 Aug. 1; 169(3): 1535-1541) and hence blocking the TLR2 activity will be beneficial in treating skin conditions that is caused by gram positive bacterial infections including *Staphylococcus epidermis, Staphylococcus aureus* as well as *Propionibacterium acnes*.

THP-1 monocyte cells ($1\times10^5$) were stimulated with 200 nM of PMA for 48 h and treated with different concentrations of test compounds. The TLR2 activity was measured after 24 h from the cell lysate using ELISA.

Figure 29:
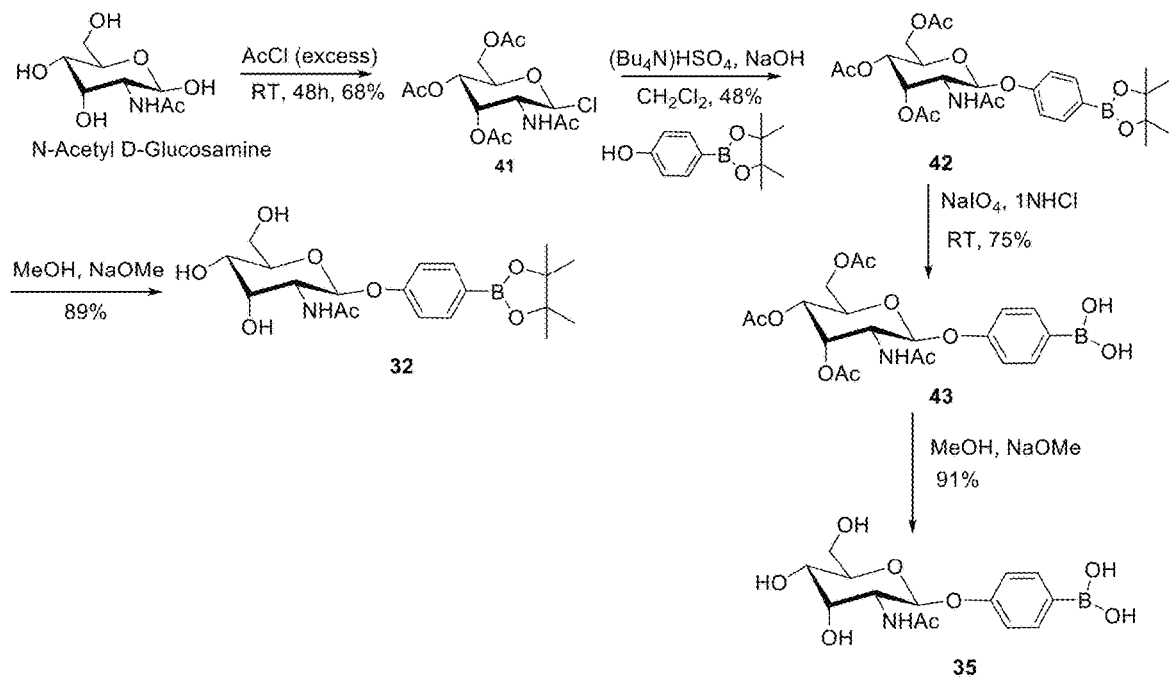
FIG. 29 shows the synthetic scheme for preparing compounds 32 and 35.

Synthesis of compound 32 (FIG. 29). 2-Acetamido-3,4, 6-tri-O-acetyl-2-deoxy-a-D-glucopyranosyl chloride 41: To a stirred solution of commercial 2-acetamido-2-deoxy-β-D-glucose (25 g, 0.113 mmol), acetyl chloride (50 mL) was added and the reaction mixture was stirred overnight. The reaction mixture was diluted with further portion of $CH_2Cl_2$ (100 mL) and poured into water-ice mixture. The organic phase was extracted with ice-cold saturated aqueous solution of $NaHCO_3$ (2×150 mL) and with ice-cold water (150 mL). The organic phase was dried, concentrated and run over a short column using EtOAc (15-50%) in hexane as an eluent to give pure product 41 in 68% of yield as a solid product. The NMR spectra were in compliance with literature reported (Sauerzapfe, Namdjou et al. 2008).

p-Pinacoloneboronatephenyl 2-acetamido-3,4,6-tri-O-acetyl-2-deoxy-β-D-glucopyranoside 42: A solution of 2-acetamido-3,4,6-tri-O-acetyl-2-deoxy-β-D-glucopyranosyl chloride 2 (5.0 g, 13.67 mmol), tetrabutylammonium hydrogen sulfate (4.65 g, 13.67 mmol), and 4-(4,4,5,5-tetramethyl-1,3,2-dioxaborolan-2-yl)phenol (3.15 g, 1.05 equiv.) in a mixture of $CH_2Cl_2$ (100 mL) and 1N NaOH (50 mL) was stirred vigorously for 1 h. The mixture was extracted with $CH_2Cl_2$ (2×125 mL), and washed with water and brine. The combined organic phase was dried over anhydrous $Na_2SO_4$, filtered, concentrated and purified by silica-gel column using EtOAc (15-50%) in hexane as an eluent to give pure product 42 in 48% of yield as a solid product.

p-Pinacoloneboronatephenyl 2-acetamido-2-deoxy-β-D-glucopyranoside 32: The above p-Pinacoloneboronatephenyl 2-acetamido-3,4,6-tri-O-acetyl-2-deoxy-β-D-glucopyranoside 42 (2.45 g, 4.45 mmol) was suspended in dry MeOH (70 mL) and methanolic solution of NaOMe (1M solution, 4.25 equivalent) was added and the mixture was stirred at RT until dissolution was complete (15 min). Dowex 50WX2-200 (5 g, previously washed in methanol) was added and removed by filtration after 15 min. The solution was evaporated in vacuo to dryness. White solid was dissolved in $CH_2Cl_2$ and MTBE was added to precipitate out white solid. The solid was filtered off and dried over high vacuum to provide compound 32 in 89% of yield. LC/MS=423.9 (M+1); $^1$H NMR ($CD_3OD$, 500 MHz): δ 1.41; (s, 12H), 2.01; (s, 3H), 3.41-3.45; (m, 1H), 3.58-3.64; (m, 2H), 3.68-3.80; (m, 1H), 3.90-4.15; (m, 2H), 5.19; (d, 1H), 7.10; (d, 2H), 7.65; (d, 2H).

p-Boronic acid phenyl 2-acetamido-2-deoxy-β-D-glucopyranoside 35: The above compound p-pinacoloneboronatephenyl 2-acetamido-3,4,6-tri-O-acetyl-2-deoxy-β-D-glucopyranoside 42 (1.5 g, 2.73 mmol) in acetone/$H_2O$ (4:1) was treated with $NaIO_4$ (2.5 equiv.), $NH_4OAc$ (1.5 equiv) and was stirred at RT for 24 hrs. pH of the reaction mixture was adjusted to 3 by adding 1N HCl and stirred for additional 30 mins. The reaction mixture was extracted with DCM and washed with brine, dried over anhydrous $Na_2SO_4$, filtered off. The combine filtrate was concentrated to give crude boronic acid and purified by silica-gel column using EtOAc (0-50%) in hexane as an eluent to give product 43 in 75% yield as a solid product. This product was then treated with NaOMe in accordance with the procedure above for 32, to give compound 35 in 91% of yield as a white solid. The NMR and MS spectra confirmed the structure of the above product. $^1$H NMR ($D_2O$+DMSO$_6$, 500 MHz): δ 1.21; (s, 3H), 2.6-2.8; (m, 4H), 3.15; (m, 2H), 3.68-3.80; (m, 1H), 4.35; (m, 1H), 6.25; (d, 2H), 7.01; (d, 2H).

Figure 30:
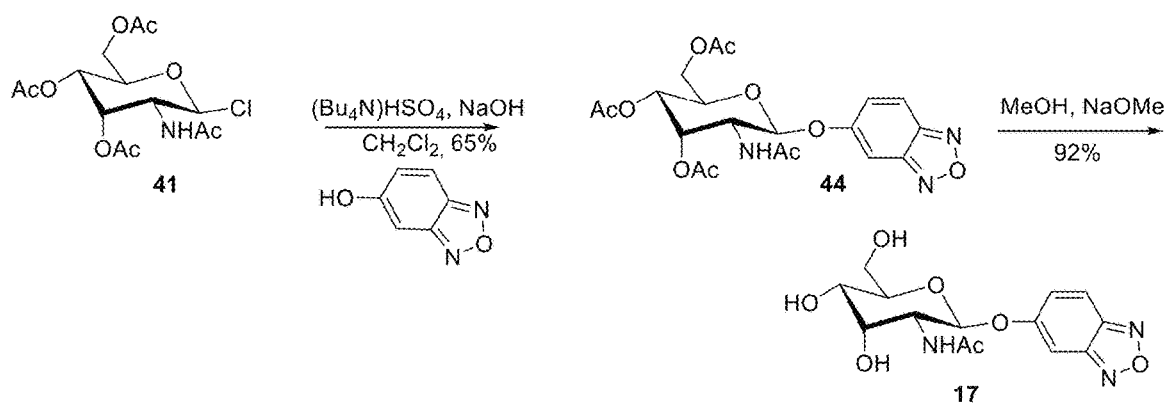
FIG. 30 shows the synthetic scheme for preparing compound 17.

Synthesis of compound 17 (FIG. 30). 2R,3S,4S,5R,6S)-5-acetamido-2-(acetoxymethyl)-6-(benzo[c][1,2,5]oxadiazol-5-yloxy)tetrahydro-2H-pyran-3,4-diyl diacetate 44: In accordance with the procedure above for compound 32, compound 2-acetamido-3,4,6-tri-O-acetyl-2-deoxy-β-D-glucopyranosyl chloride 41 (1.0 g, 2.73 mmol) was reacted with commercial benzo[c][1,2,5]oxadiazol-5-ol (1.05 equiv.) to provide the intermediate 44 in 65% of yield as a white solid. The NMR spectra confirmed the structure of the above product.

N-((2S,3R,4S,5S,6R)-2-(benzo[c][1,2,5]oxadiazol-5-yloxy)-4,5-dihydroxy-6-(hydroxymethyl)tetrahydro-2H-pyran-3-yl)acetamide 17: Following the same procedure as described for compound 32, the intermediate 44 (0.25 g, 0.53 mmol) was converted to compound 17 in 92% of yield as white solid. The NMR and MS spectra confirmed the structure of the above product. LC/MS=339.9 (M+1); $^1$H NMR ($CD_3OD$, 500 MHz): δ 2.01; (s, 3H), 3.41-3.45; (m, 1H), 3.58-3.64; (m, 2H), 3.68-3.80; (m, 1H), 3.90-4.15; (m, 2H), 5.25; (d, 1H), 7.21; (d, 1H), 7.32; (s, 1H), 7.83; (s, 1H).

Figure 31:
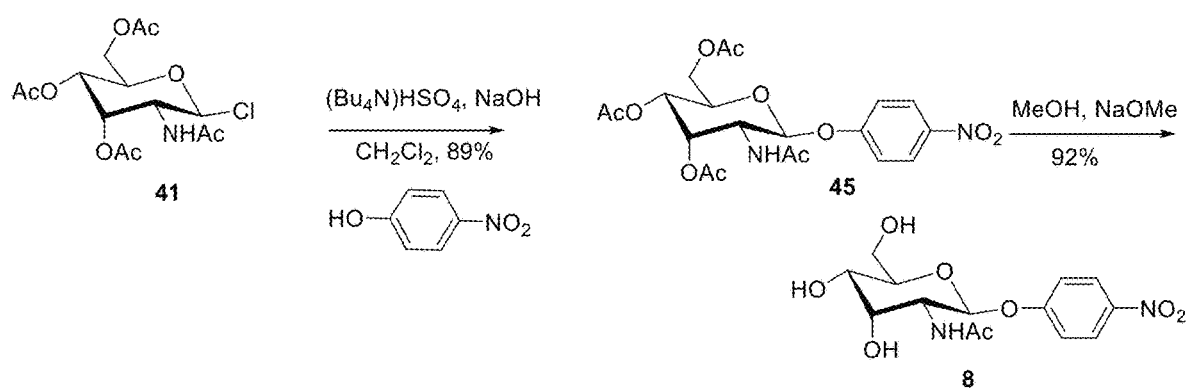
FIG. 31 shows the synthetic scheme for preparing compound 8.

Synthesis of compound 8 (FIG. 31). p-Nitrophenyl 2-acetamido-3,4,6-tri-O-acetyl-2-deoxy-β-D-glucopyranoside intermediate 45: Following the procedure for compound 42, compound 2-acetamido-3,4,6-tri-O-acetyl-2-deoxy-β-D-glucopyranosyl chloride 41 (1.0 g, 2.73 mmol) was coupled with commercial p-nitro-phenol (1.05 equiv.) to give intermediate 45 in 89% of yield as a white solid. $^1$H NMR p-Nitrophenyl 2-acetamido-2-deoxy-β-D-glucopyranoside 8: Following the same procedure as used for synthesizing 32, the above intermediate 45 (0.25 g, 0.53 mmol) was converted to compound 8 in 92% of yield as pure white solid. LC/MS=343.1 (M+1); $^1$H NMR ($D_2O$)+$CD_3OD$, 500 MHz): δ 2.01; (s, 3H), 3.46; (t, 1H), 3.60-3.65; (m, 2H), 3.68-3.81; (dd, 1H), 3.90-4.15; (m, 2H), 5.24; (d, 2H), 7.20; (d, 2H), 8.23; (d, 2H).

Figure 33:
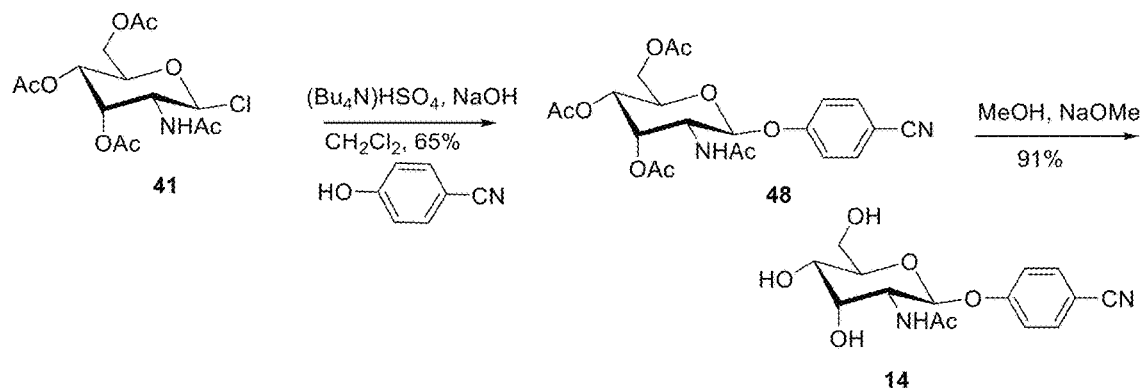
FIG. 33 shows the synthetic scheme for preparing compound 17.

Synthesis of compound 14 (FIG. 33). p-Cyanophenyl-2-acetamido-3,4,6-tri-O-acetyl-2-deoxy-β-D-glucopyranoside intermediate 48: Following the procedure for compound 42, compound 2-acetamido-3,4,6-tri-O-acetyl-2-deoxy-β-D-glucopyranosyl chloride 41 (1.0 g, 2.73 mmol) was coupled with commercial p-cyanophenol (1.05 equiv.) to provide compound 48 in 65% of yield as a white solid. $^1$H NMR ($CD_3OD$, 500 MHz): δ 1.65; (s, 3H), 2.18; (s, 12H), 3.88;

(m, 1H), 4.15-4.22; (m, 2H), 4.25; (m, 1H), 5.19; (m, 1H), 5.45; (m, 2H), 5.80; (m, 1H), 7.15; (d, 2H), 7.65; (d, 2H).

p-Cyanophenyl 2-acetamido-2-deoxy-β-D-glucopyranoside 14: Following the procedure for compound 32, the above intermediate 48 (0.25 g, 0.53 mmol) was converted to compound 14 in 91% of yield as pure white solid. LC/MS=323.1 (M+1); $^1$H NMR (D$_2$O+CD$_3$OD, 600 MHz): δ 2.01; (s, 3H), 3.52; (t, 1H), 3.60-3.68; (m, 2H), 3.75-3.81; (dd, 1H), 3.90-4.15; (m, 2H), 5.24; (d, 2H), 7.20; (d, 2H), 7.75; (d, 2H).

Figure 32:
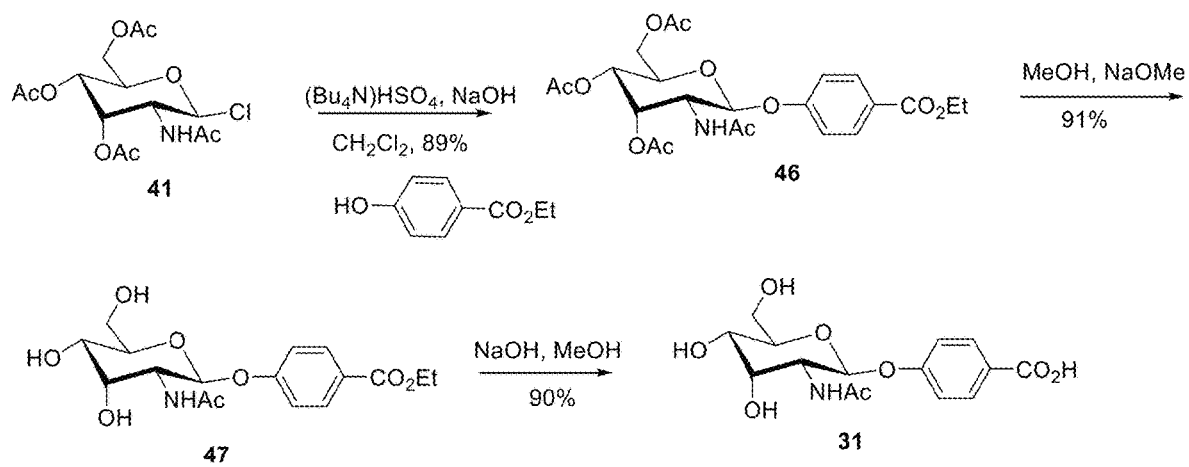
FIG. 32 shows the synthetic scheme for preparing compound 31.

Synthesis of compound 31 (FIG. 32). 4-Ethylcarboxylatephenyl-2-acetamido-3,4,6-tri-O-acetyl-2-deoxy-β-D-glucopyranoside intermediate 46: Following the procedure for compound for 42, compound 2-acetamido-3,4,6-tri-O-acetyl-2-deoxy-β-D-glucopyranosyl chloride 41 (1.0 g, 2.73 mmol) was coupled with commercial 4-hydroxyethylbenzoate (1.05 equiv.) to give intermediate 46 in 89% of yield as an oil.

4-Carboxylatephenyl 2-acetamido-2-deoxy-β-D-glucopyranoside compound 31: Following the procedure for compound for 32, the above intermediate 46 (0.25 g, 0.53 mmol) was converted to compound 31 in 90% of yield as pure white solid. $^1$H NMR (D$_2$O, 500 MHz): δ 1.85; (s, 3H), 3.41-3.45; (m, 1H), 3.58-3.64; (m, 3H), 3.80-3.95; (m, 2H), 5.19; (d, 2H), 6.95; (m. 2H), 7.85; (m, 2H).

Figure 34:
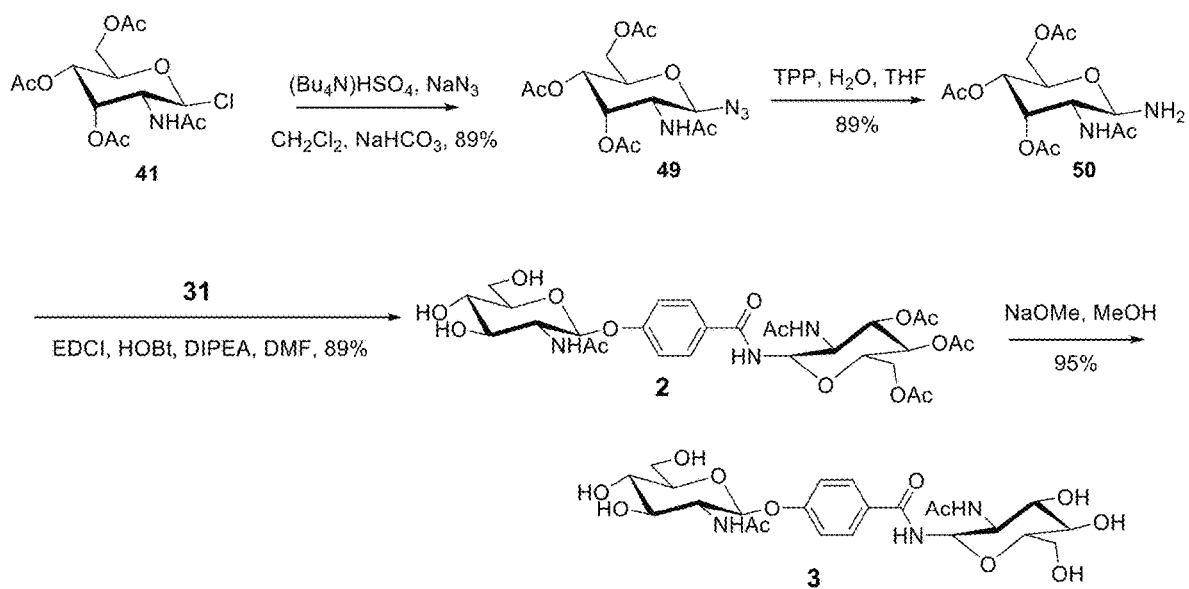
FIG. 34 shows the synthetic scheme for preparing compounds 2 and 3.

2-acetamido-3,4,6-tri-O-acetyl-2-deoxy-β-D-glucopyranoside azide intermediate 49 (FIG. 34): 2-acetamido-3,4,6-tri-O-acetyl-2-deoxy-β-D-glucopyranosyl chloride 41 was converted to sugar azide 49 following literature protocol, which was converted to amine 50 using TPP, and H$_2$O in 89% yield as a white solid.

Di-saccharide compound 2: To a stirred solution of amine 50 (0.25 g, 0.72 mmol) in anhydrous DMF were added compound 31 (0.197 g, 0.72 mmol), EDCI (0.179 g, 1.44 mmol), HOBt (0.089 g, 0.866 mmol) and DIPEA (0.195 g, 1.8 mmol) and the reaction mixture was stirred for overnight. The reaction mixture was quenched by adding water and all solvent were removed under high vacuum. The crude solid mass was purified by silica-gel column using MeOH (0-20%) in EtOAc as an eluent to give pure product 2 in 89% of yield as a solid. $^1$H NMR (CD$_3$OD+D$_2$O, 500 MHz): δ 1.90 (d, 3H), 2.0-2.11; (m, 12H), 3.45-3.58; (m, 2H), 3.60-3.68; (m, 1H), 3.68-3.80; (m, 1H), 3.82-4.05; (m, 3H), 4.110-4.21; (m, 1H), 4.35-4.45; (m, 1H), 5.08-5.10; (m, 2H), 5.20; (m, 1H), 5.42; (m, 1H), 5.45; (m, 1H), 7.12; (d, 2H), 7.80; (d, 2H).

Di-sugar analog compound 3: Following the procedure for 32, the compound 2 (0.21 g, 0.313 mmol) was converted to compound 3 in 95% of yield as pure white solid. LC/MS=544.2 (M+1); 1H NMR (CD$_3$OD+D$_2$O, 600 MHz): δ 1.80; (d, 6H), 3.30-3.45; (m, 3H), 3.45-3.60; (m, 4H), 3.60-3.68; (m, 2H), 3.71-3.90; (m, 4H), 5.10; (m, 2H), 6.90; (d, 2H), 7.55; (d, 2H).

Compound 23 was synthesized following same procedure as described for compound 17: $^1$H NMR (CD$_3$OD, 500 MHz): δ 1.01; (s, 12H), 1.65; (s, 3H), 3.20; (m, 1H), 3.31; (m, 1H), 3.40-3.51; (m, 2H), 3.60; (m, 1H), 3.75; (m, 1H), 5.20; (d, 1H), 6.8; (d, 1H), 7.05; (t, 1H), 7.21; (d, 1H), 7.8; (bs, 1H).

Figure 35:
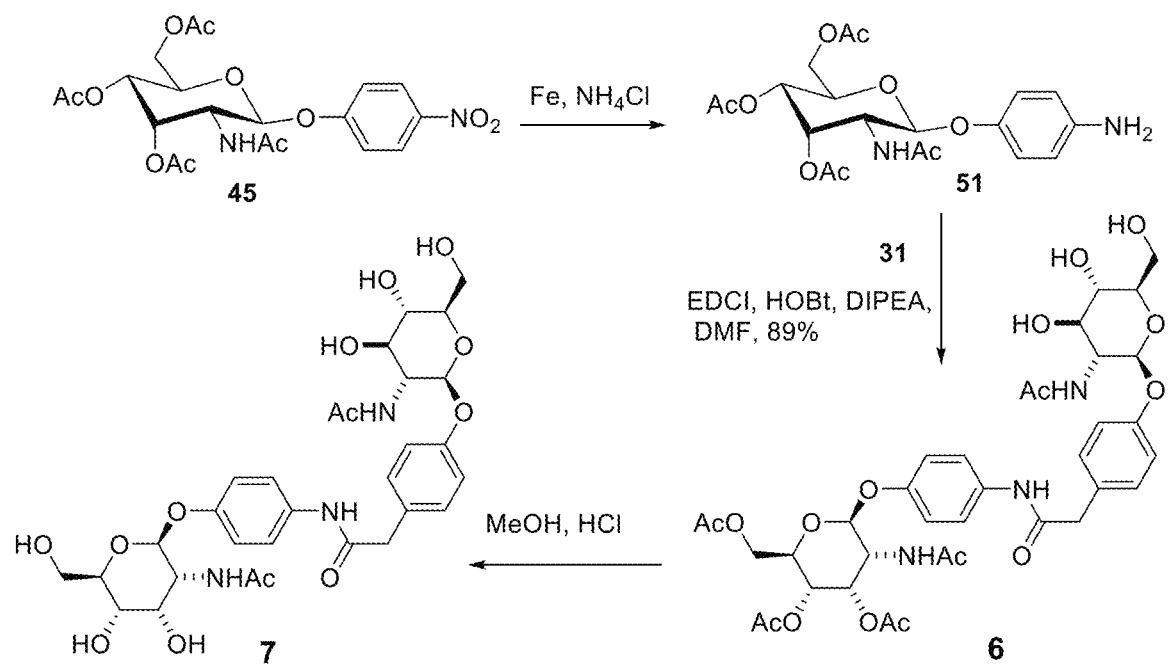
FIG. 35 shows the synthetic scheme for preparing compounds 6 and 7.

Di-sugar analog compound 6 (FIG. 35). Using well know literature procedure for reduction of —NO$_2$ to amine using Fe, NH$_4$Cl, compound 45 was converted to amine 51 in 91% yield as semi-solid product which was directly coupled with compound 31 following the same procedure above as described for compound 2 to provide di-sugar amide compound 6 in 89% yield. $^1$H NMR (CD$_3$OD+D$_2$O, 500 MHz): δ 1.80-2.2; (m, 15H), 3.40-3.65; (m, 4H), 3.75-3.85; (m, 1H), 3.85-4.25; (m, 4H), 5.08-5.10; (m, 2H), 5.20; (m, 1H), 5.42; (m, 1H), 5.45; (m, 1H), 7.0-7.20; (dd, 4H), 7.60; (d, 2H), 7.90; (d, 2H).

Following the same procedure as described for 32, compound 6 was converted to compound 7 in 92% of yield as pure white solid. $^1$H NMR (CD$_3$OD+D$_2$O, 500 MHz): δ 1.80-2.2; (2s, 6H), 3.30-3.45; (m, 7H), 3.55-3.85; (m, 5H), 5.08-5.10; (m, 2H), 7.0-7.20; (dd, 4H), 7.60; (d, 2H), 7.90; (d, 2H).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Luster, A. D., The role of chemokines in linking innate and adaptive immunity. Current Opinion in Immunology 2002, 14, 129-135.
2. Safdieh, J. E.; Mead, P. A.; Sepkowitz, K. A.; Kiehn, T. E.; Abrey, L. E., Bacterial and fungal meningitis in patients with cancer. Neurology 2008, 70, 943-7.
3. Broad, A.; Jones, D. E.; Kirby, J. A., Toll-like receptor (TLR) response tolerance: a key physiological "damage limitation" effect and an important potential opportunity for therapy. Current medicinal chemistry 2006, 13, 2487-502.
4. Cavaillon, J. M.; Adrie, C.; Fitting, C.; Adib-Conquy, M., Endotoxin tolerance: is there a clinical relevance? Journal of endotoxin research 2003, 9, 101-7.
5. Cross, A. S., Endotoxin tolerance-current concepts in historical perspective. Journal of endotoxin research 2002, 8, 83-98.
6. Murphey, E. D.; Fang, G.; Sherwood, E. R., Endotoxin pretreatment improves bacterial clearance and decreases mortality in mice challenged with Staphylococcus aureus. Shock (Augusta, Ga.) 2008, 29, 512-8.
7. Wy, C. A.; Goto, M.; Young, R. I.; Myers, T. F.; Muraskas, J., Prophylactic treatment of endotoxic shock with monophosphoryl lipid A in newborn rats. Biology of the neonate 2000, 77, 191-5.
8. Wynn, J. L.; Scumpia, P. O.; Winfield, R. D.; Delano, M. J.; Kelly-Scumpia, K.; Barker, T.; Ungaro, R.; Levy, O.; Moldawer, L. L., Defective innate immunity predisposes murine neonates to poor sepsis outcome but is reversed by TLR agonists. Blood 2008, 112, 1750-8.
9. Thoelen, S.; Van Damme, P.; Mathei, C.; Leroux-Roels, G.; Desombere, I.; Safary, A.; Vandepapeliere, P.; Slaoui, M.; Meheus, A., Safety and immunogenicity of a hepatitis B vaccine formulated with a novel adjuvant system. Vaccine 1998, 16, 708-14.
10. Romero, C. D.; Varma, T. K.; Hobbs, J. B.; Reyes, A.; Driver, B.; Sherwood, E. R., The Toll-Like Receptor 4 Agonist Monophosphoryl Lipid A Augments Innate Host Resistance to Systemic Bacterial Infection. Infection and Immunity 2011, 79, 3576-3587.
11. Adanitsch, F.; Shi, J.; Shao, F.; Beyaert, R.; Heine, H.; Zamyatina, A., Synthetic glycan-based TLR4 agonists targeting caspase-4/11 for the development of adjuvants and immunotherapeutics. Chemical Science 2018, 9, 3957-3963.
12. Rubenfeld, G. D.; Caldwell, E.; Peabody, E.; Weaver, J.; Martin, D. P.; Neff, M.; Stern, E. J.; Hudson, L. D., Incidence and outcomes of acute lung injury. N Engl J Med 2005, 353, 1685-93.
13. Villar, J.; Blanco, J.; Kacmarek, R. M., Current incidence and outcome of the acute respiratory distress syndrome. Current opinion in critical care 2016, 22, 1-6.
14. Salim, A.; Martin, M.; Constantinou, C.; Sangthong, B.; Brown, C.; Kasotakis, G.; Demetriades, D.; Belzberg, H., Acute respiratory distress syndrome in the trauma intensive care unit: Morbid but not mortal. Arch Surg 2006, 141, 655-8.
15. Bhandari, A.; Bhandari, V., "New" Bronchopulmonary Dysplasia: A clinical review. Clin Pulm Med 2011, 18, 137-143.
16. Bhandari, A.; Bhandari, V., Pitfalls, problems, and progress in bronchopulmonary dysplasia. Pediatrics 2009, 123, 1562-73.
17. Jensen, E. A.; Schmidt, B., Epidemiology of bronchopulmonary dysplasia. Birth defects research. Part A, Clinical and molecular teratology 2014, 100, 145-57.
18. Trembath, A.; Laughon, M. M., Predictors of bronchopulmonary dysplasia. Clin Perinatol 2012, 39, 585-601.
19. Bancalari, E.; Claure, N., Bronchopulmonary dysplasia: definitions and epidemiology. In Bronchopulmonary Dysplasia, First ed.; Bhandari, V., Ed. Springer International Publishing: Switzerland, 2016; pp 167-182.
20. Smith, V. C.; Zupancic, J. A.; McCormick, M. C.; Croen, L. A.; Greene, J.; Escobar, G. J.; Richardson, D. K., Trends in severe bronchopulmonary dysplasia rates between 1994 and 2002. J Pediatr 2005, 146, 469-73.
21. Russell, R. B.; Green, N. S.; Steiner, C. A.; Meikle, S.; Howse, J. L.; Poschman, K.; Dias, T.; Potetz, L.; Davidoff, M. J.; Damus, K.; Petrini, J. R., Cost of hospitaliza- 22. Bhandari, A.; McGrath-Morrow, S., Long-term pulmonary outcomes of patients with bronchopulmonary dysplasia. Semin Perinatol 2013, 37, 132-7.
23. Natarajan, G.; Pappas, A.; Shankaran, S.; Kendrick, D. E.; Das, A.; Higgins, R. D.; Laptook, A. R.; Bell, E. F.; Stoll, B. J.; Newman, N.; Hale, E. C.; Bara, R.; Walsh, M. C., Outcomes of extremely low birth weight infants with bronchopulmonary dysplasia: impact of the physiologic definition. Early Hum Dev 2012, 88, 509-15.
24. Raju, T. N. K.; Buist, A. S.; Blaisdell, C. J.; Moxey-Mims, M.; Saigal, S., Adults born preterm: a review of general health and system-specific outcomes. Acta Paediatr 2017, 106, 1409-1437.
25. Balany, J.; Bhandari, V., Understanding the Impact of Infection, Inflammation, and Their Persistence in the Pathogenesis of Bronchopulmonary Dysplasia. Front Med (Lausanne) 2015, 2, 90.
26. Bhandari, V., Postnatal inflammation in the pathogenesis of bronchopulmonary dysplasia. Birth defects research. Part A, Clinical and molecular teratology 2014, 100, 189-201.
27. Harijith, A.; Bhandari, V., Hyperoxia in the pathogenesis of bronchopulmonary dysplasia. In Bronchopulmonary Dysplasia, First ed.; Bhandari, V., Ed. Springer International Publishing: Switzerland, 2016; pp 3-26.
28. Li, Z.; Choo-Wing, R.; Sun, H.; Sureshbabu, A.; Sakurai, R.; Rehan, V. K.; Bhandari, V., A potential role of the JNK pathway in hyperoxia-induced cell death, myofibroblast transdifferentiation and TGF-beta1-mediated injury in the developing murine lung. BMC Cell Biol 2011, 12, 54.
29. Choo-Wing R, S. M., Harijith A, Bowen B, Pryhuber G, Janer C, Andersson S, Homer R J, Bhandari V, Hyperoxia and interferon-γ-induced injury in developing lungs occur via cyclooxygenase-2 and the endoplasmic reticulum stress-dependent pathway Am J Respir Cell Mol Biol 2013, 48, 749-757.
30. Sureshbabu, A.; Syed, M.; Das, P.; Janer, C.; Pryhuber, G.; Rahman, A.; Andersson, S.; Homer, R. J.; Bhandari, V., Inhibition of RPTOR Prevents Hyperoxia-induced Lung Injury by Enhancing Autophagy and Reducing Apoptosis in Neonatal Mice. Am J Respir Cell Mol Biol 2016.
31. Sureshbabu, A.; Syed, M. A.; Boddupalli, C. S.; Dhodapkar, M. V.; Homer, R. J.; Minoo, P.; Bhandari, V., Conditional overexpression of TGFbeta1 promotes pulmonary inflammation, apoptosis and mortality via TGF-betaR2 in the developing mouse lung. Respir Res 2015, 16, 4.
32. Sun H, C.-W. R., Sureshbabu A, Fan J, Leng L, Yu S, Jiang D, Noble P, Homer R J, Bucala R, Bhandari V, A critical regulatory role for macrophage migration inhibitory factor in hyperoxia-induced injury in the developing murine lung. PLoS ONE 2013, 8.
33. Sun H, C.-W. R., Fan J, Leng L, Syed M A, Hare A A, Jorgensen W L, Bucala R, Bhandari V, Small molecular modulation of macrophage migration inhibitory factor in the hyperoxia-induced mouse model of bronchopulmonary dysplasia. Respir Res 2013, 14.
34. Bhandari, V.; Choo-Wing, R.; Lee, C. G.; Yusuf, K.; Nedrelow, J. H.; Ambalavanan, N.; Malkus, H.; Homer, R. J.; Elias, J. A., Developmental regulation of NO-mediated VEGF-induced effects in the lung. Am J Respir Cell Mol Biol 2008, 39, 420-30.
35. Syed, M. A.; Choo-Wing, R.; Homer, R. J.; Bhandari, V., Role of Nitric Oxide Isoforms in Vascular and Alveolar Development and Lung Injury in Vascular Endothelial Growth Factor Overexpressing Neonatal Mice Lungs. PLoS One 2016, 11, e0147588.
36. Bhandari, V., Drug therapy trials for the prevention of bronchopulmonary dysplasia: current and future targets. Front Pediatr 2014, 2, 76.
37. McEvoy, C. T.; Jain, L.; Schmidt, B.; Abman, S.; Bancalari, E.; Aschner, J. L., Bronchopulmonary dysplasia: NHLBI Workshop on the Primary Prevention of Chronic Lung Diseases. Annals of the American Thoracic Society 2014, 11 Suppl 3, S146-53.
38. Densmore, J. C.; Signorino, P. R.; Ou, J.; Hatoum, O. A.; Rowe, J. J.; Shi, Y.; Kaul, S.; Jones, D. W.; Sabina, R. E.; Pritchard, K. A., Jr.; Guice, K. S.; Oldham, K. T., Endothelium-derived microparticles induce endothelial dysfunction and acute lung injury. Shock 2006, 26, 464-71.
39. Moore, K. W.; Rousset, F.; Banchereau, J., Evolving principles in immunopathology: interleukin 10 and its relationship to Epstein-Barr virus protein BCRF1. Springer seminars in immunopathology 1991, 13, 157-66.
40. Kapur, R.; Kim, M.; Rebetz, J.; Rondina, M. T.; Porcelijn, L.; Semple, J. W., Low levels of interleukin-10 in patients with transfusion-related acute lung injury. Annals of Translational Medicine 2017, 5, 339.
41. Bi, M. H.; Wang, B. E.; Zheng, X. X.; Li, M.; Mayer, K.; Zhang, S. W., [The effect of recombinant interleukin-10/Fc fusion protein on lipopolysaccharide-induced acute lung injury in mice]. Zhongguo wei zhong bing ji jiu yi xue=Chinese critical care medicine=Zhongguo weizhongbing jijiuyixue 2008, 20, 461-4.
42. Lee, H.-S.; Kim, C.-K., Effect of recombinant IL-10 on cultured fetal rat alveolar type II cells exposed to 65%-hyperoxia. Respiratory Research 2011, 12, 68-68.
43. Bhandari, V., Molecular mechanisms of hyperoxia-induced acute lung injury.
Frontiers in bioscience: a journal and virtual library 2008, 13, 6653-61.
44. Li, H. D.; Zhang, Q. X.; Mao, Z.; Xu, X. J.; Li, N. Y.; Zhang, H., Exogenous interleukin-10 attenuates hyperoxia-induced acute lung injury in mice. Experimental physiology 2015, 100, 331-40.
45. Bhandari, A.; Bhandari, V., Biomarkers in bronchopulmonary dysplasia. Paediatr Respir Rev 2013, 14, 173-9.
46. Menden, H. L.; Xia, S.; Mabry, S. M.; Navarro, A.; Nyp, M. F.; Sampath, V., Nicotinamide Adenine Dinucleotide Phosphate Oxidase 2 Regulates LPS-Induced Inflammation and Alveolar Remodeling in the Developing Lung. Am J Respir Cell Mol Biol 2016, 55, 767-778.
47. Yao, L.; Shi, Y.; Zhao, X.; Hou, A.; Xing, Y.; Fu, J.; Xue, X., Vitamin D attenuates hyperoxia-induced lung injury through downregulation of Toll-like receptor 4. Int J Mol Med 2017, 39, 1403-1408.
48. Glaser, K.; Speer, C. P., Pre and Postnatal inflammation in the pathogenesis of bronchopulmonary dysplasia. In Bronchopulmonary Dysplasia, First ed.; Bhandari, V., Ed. Springer International Publishing: Switzerland, 2016; pp 55-77.
49. Xia, W.; Liu, P.; Zhang, J.; Chen, J., Biological activities of chitosan and chitooligosaccharides. Food Hydrocolloids 2011, 25, 170-179.
50. Minami, S.; Suzuki, H.; Okamoto, Y.; Fujinaga, T.; Shigemasa, Y., Chitin and chitosan activate complement via the alternative pathway. Carbohydrate Polymers 1998, 36, 151-155.
51. Qiao, Y.; Bai, X.-F.; Du, Y.-G., Chitosan oligosaccharides protect mice from LPS challenge by attenuation of inflammation and oxidative stress. International Immunopharmacology 2011, 11, 121-127.
52. Okawa, Y.; Kobayashi M Fau—Suzuki, S.; Suzuki S Fau—Suzuki, M.; Suzuki, M., Comparative study of protective effects of chitin, chitosan, and N-acetyl chitohexaose against *Pseudomonas aeruginosa* and Listeria monocytogenes infections in mice.
53. Solov; #039; eva, T.; Davydova, V.; Krasikova, I.; Yermak, I., Marine Compounds with Therapeutic Potential in Gram-Negative Sepsis. Marine Drugs 2013, 11, 2216-2229.
54. Kim, H. M.; Park, B. S.; Kim, J.-I.; Kim, S. E.; Lee, J.; Oh, S. C.; Enkhbayar, P.; Matsushima, N.; Lee, H.; Yoo, O. J.; Lee, J.-O., Crystal Structure of the TLR4-MD-2 Complex with Bound Endotoxin Antagonist Eritoran. Cell 2007, 130, 906-917.
55. Li, N.; Zhuang, C.; Wang, M.; Sun, X.; Nie, S.; Pan, W., Liposome coated with low molecular weight chitosan and its potential use in ocular drug delivery. International Journal of Pharmaceutics 2009, 379, 131-138.
56. Janes, K. A.; Fresneau, M. P.; Marazuela, A.; Fabra, A.; Alonso, M. a. J., Chitosan nanoparticles as delivery systems for doxorubicin. Journal of Controlled Release 2001, 73, 255-267.
57. Williams, J.; Lansdown, R.; Sweitzer, R.; Romanowski, M.; LaBell, R.; Ramaswami, R.; Unger, E., Nanoparticle drug delivery system for intravenous delivery of topoisomerase inhibitors. Journal of Controlled Release 2003, 91, 167-172.
58. Panda, S. K.; Kumar, S.; Tupperwar, N. C.; Vaidya, T.; George, A.; Rath, S.; Bal, V.; Ravindran, B., Chitohexaose Activates Macrophages by Alternate Pathway through TLR4 and Blocks Endotoxemia. PLoS Pathog 2012, 8, e1002717.
59. Sauerzapfe, B.; Namdjou, D. J.; Schumacher, T.; Linden, N.; Křenek, K.; Křen, V.; Elling, L., Characterization of recombinant fusion constructs of human β1,4-galactosyltransferase 1 and the lipase pre-propeptide from *Staphylococcus hyicus*. Journal of Molecular Catalysis B: Enzymatic 2008, 50, 128-140.

What is claimed is:

1. A composition that modulates an immune response, the composition comprising:
at least one compound selected from 1, 2, 3, 6, 7, 11, 14, 23, 32, 35, or 38, wherein the composition is formulated to inhibit a TLR4 receptor, a TLR2 receptor, or both the TLR2 and the TLR4 receptor and has the formula and concentration below:

| Compound Number | Structure | Concentration (μM) | % inhibition over control TLR4 | TLR2 |
|---|---|---|---|---|
| 1 | 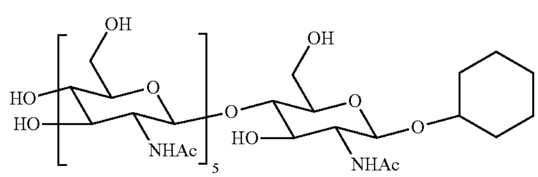 | 1-10 | +++ | |
| | | 75-100 | +++ | |
| 2 | 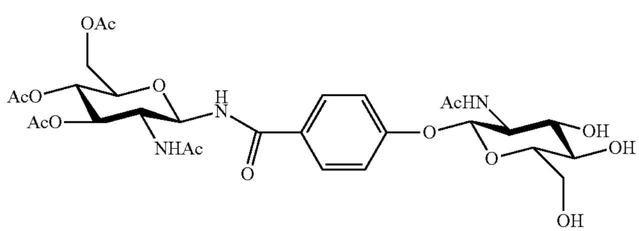 | 1-10 | ++ | + |
| | | 75-100 | +++ | +++ |
| 3 | 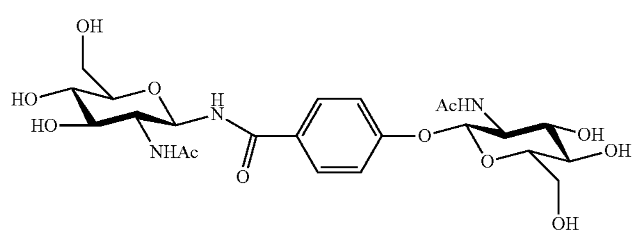 | 1-10 | ++ | ++ |
| | | 75-100 | +++ | +++ |

-continued

| Compound Number | Structure | Concentration (μM) | % inhibition over control TLR4 | TLR2 |
|---|---|---|---|---|
| 6 | 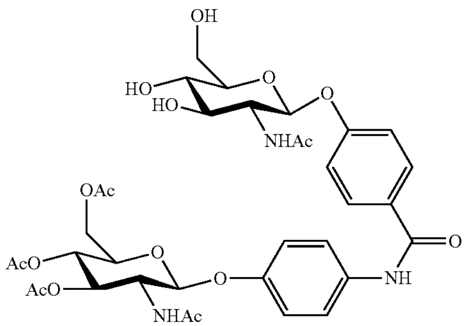 | 1-10<br>75-100 | ++<br>+++ | |
| 7 | 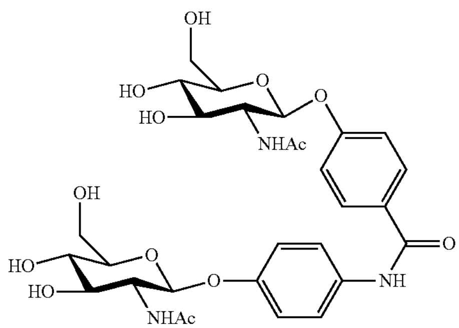 | 1-10<br>75-100 | +++<br>+++ | ++<br>+++ |
| 11 | 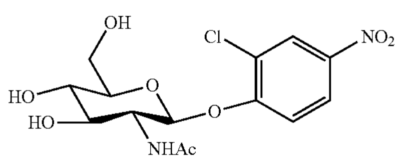 | 1-10<br>75-100 | +<br>+ | |
| 14 | 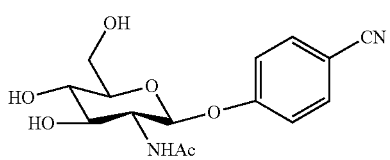 | 1<br>100 | +++<br>+++ | |
| 23 | 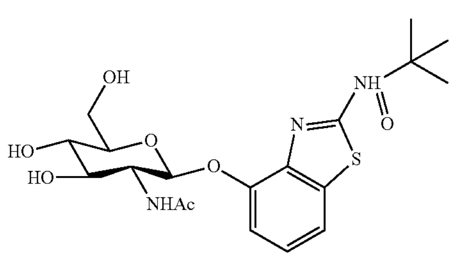 | 1-10<br>75-100 | +<br>+ | |
| 32 | 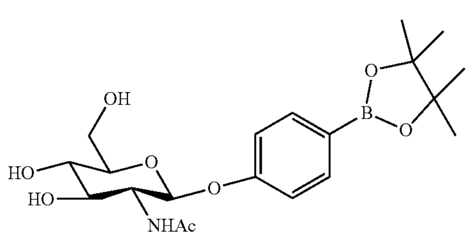 | 1-10<br>75-100 | +++<br>+++ | +++<br>+ |

| Compound Number | Structure | Concentration (μM) | % inhibition over control TLR4 | TLR2 |
|---|---|---|---|---|
| 35; or | 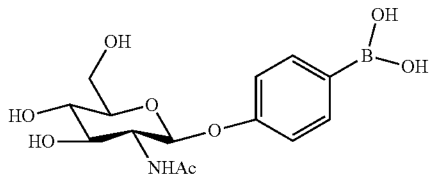 | 1-10 75-100 | +++ | |
| 38 | 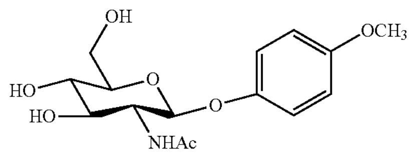 | 1-10 75-100 | | ++. |

2. The composition of claim 1, wherein the composition is formulated into a pharmaceutical composition in an amount to treat hyperinflammation selected from lung injury, lung cancer, irritable bowel disease, arthritis, psoriasis, acne, BPD, arthritis, necrotizing enterocolitis or sepsis, and is provided at a low concentration to inhibit an immune response, wherein the compound is selected from:

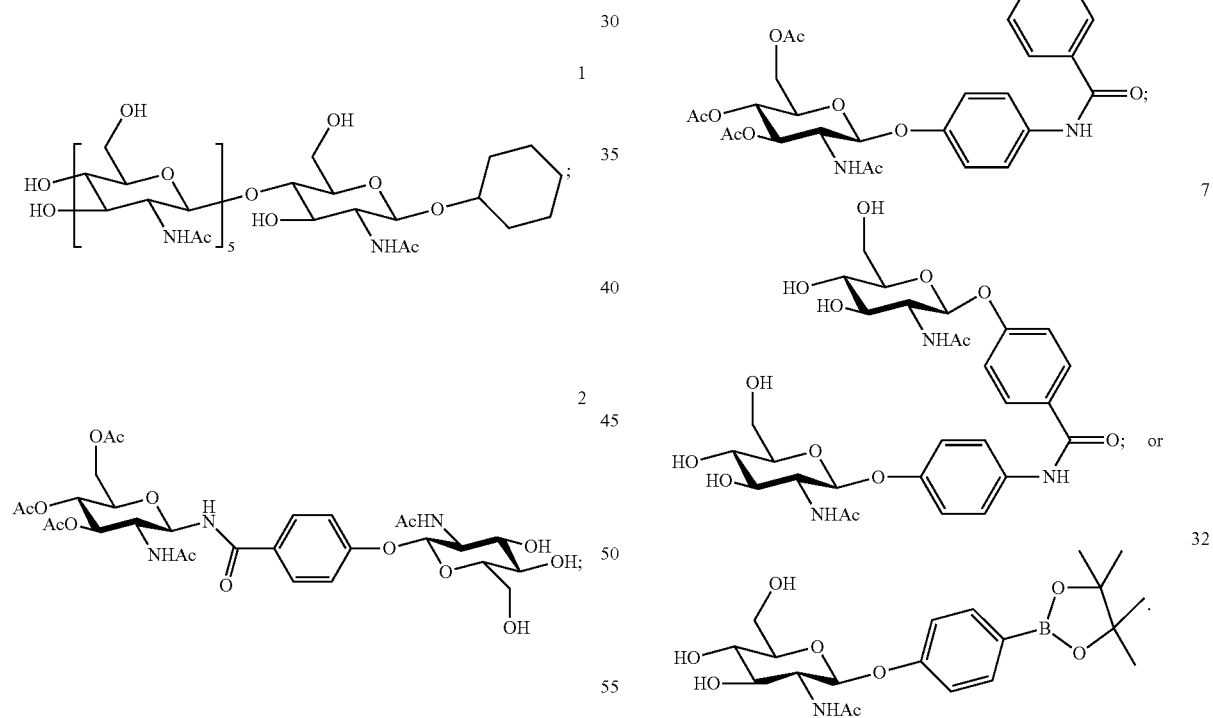

3. The composition of claim 1, wherein the composition is formulated into a pharmaceutical composition comprising one or more pharmaceutically acceptable excipients, buffers, or salts.

4. The composition of claim 1, wherein the composition is formulated into a pharmaceutical composition adapted for pulmonary, alveolar, enteral, parenteral, intravenous, topical, or oral administration.

5. The composition of claim 1, wherein the composition is formulated into an aerosol, a nebulizer, or an inhaler.

6. The composition of claim 1, wherein the composition further comprises one or more liposomes, polymers, surfactants, salts, or buffers.

7. The composition of claim 1, wherein the composition further comprises an additional therapeutic agent selected from the group consisting of corticosteroids, bronchodilators, anticholinergics, vasodilators, diuretics, anti-hypertensive agents, acetazolamide, antibiotics, antivirals, immunosuppressive drugs, and surfactants.

8. The composition of claim 1, wherein the composition is provided in an amount that competitively inhibits inflammation and activates macrophages to protect lung tissue damage or limit lung tissue injury.

9. The composition of claim 1, wherein the compound is provided in an amount that is a TLR4 modulator and upregulates IL-10.

10. The composition of claim 1, wherein the compound is provided in an amount that is a TLR2, TLR4, TLR7 and TLR8 inhibitor and downregulates IL-1β.

11. The composition of claim 1, wherein the compound is a TLR9 inhibitor and down regulates IFN-α.

12. A compound formulated into a composition that modulates an immune response, the composition comprising:

at least one compound is selected from compound 8, 17, 28, 29, 30, or 35, wherein the composition is formulated to inhibit a TLR4 receptor, a TLR2 receptor, or both the TLR2 and the TLR4 receptor, wherein the composition is formulated to inhibit the immune response at a first concentration, and activate the immune response at a second concentration, wherein the compound is formulated into a low or a high dose composition comprising:

| Compound Number | Structure | Concentration (μM) | % inhibition over control TLR4 | % inhibition over control TLR2 | % activation over control TLR4 | % activation over control TLR2 |
|---|---|---|---|---|---|---|
| 8 | 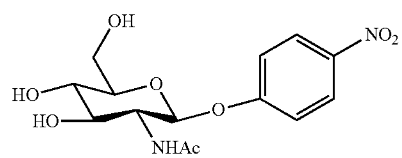 | 1-10 | +++ | + | | |
|   | | 75-100 | | ++ | ++ | ++ |
| 17 | 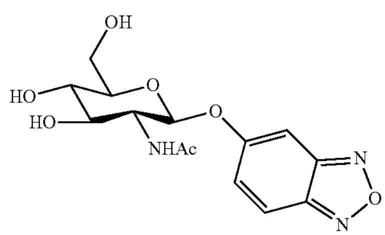 | 1-10 | --- | ++ | | |
|   | | 75-100 | ----- | +++ | ++ | |
| 28 | 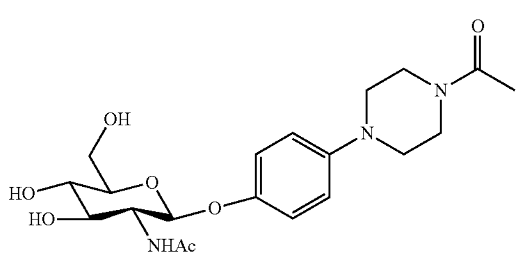 | 1-10 | + | | | |
|   | | 75-100 | | | | ++ |
| 29 | 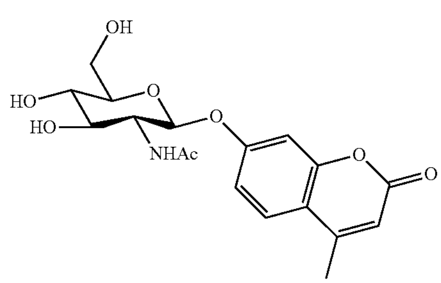 | 1-10 | | | | ++ |
|   | | 75-100 | | | + | + |

-continued

| Compound Number | Structure | Concentration (μM) | % inhibition over control TLR4 | % inhibition over control TLR2 | % activation over control TLR4 | % activation over control TLR2 |
|---|---|---|---|---|---|---|
| 30; or | (structure shown) | 1-10 75-100 | + | | + | |
| 35 | (structure shown) | 1-10 75-100 | +++ | | ++ | +. |

13. The composition of claim 12, wherein the compound has the formula

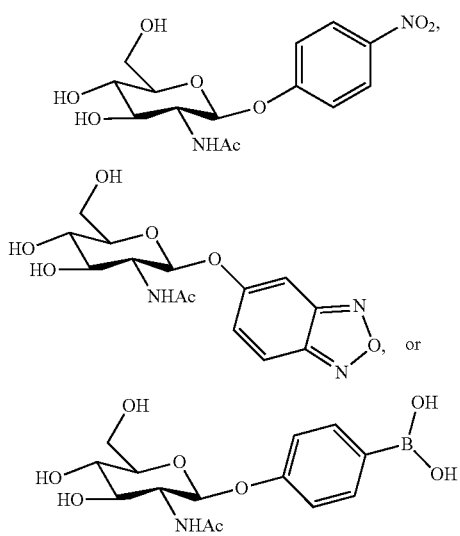

and the composition is dosed at a concentration of between 0.1-50 milligrams/kg to inhibit an immune response.

14. The composition of claim 12, wherein the compound has the formula

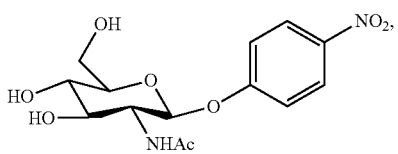

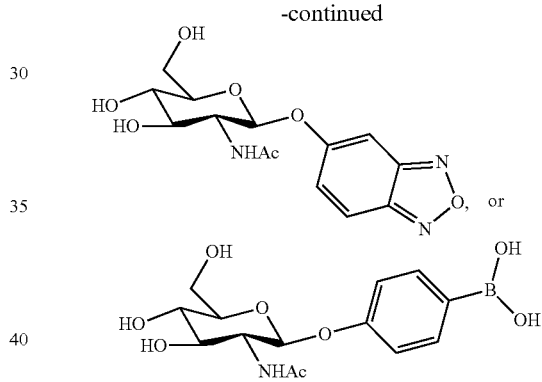

and is formulated is dosed at concentration greater than 50 milligrams/kg to activate an immune response.

15. The composition of claim 12, wherein the composition is formulated into a pharmaceutical composition comprising one or more pharmaceutically acceptable excipients, buffers, or salts.

16. The composition of claim 12, wherein the composition is formulated into a pharmaceutical composition adapted for pulmonary, alveolar, enteral, parenteral, intravenous, topical, or oral administration.

17. The composition of claim 12, wherein the composition is formulated into an aerosol, a nebulizer, or an inhaler.

18. The composition of claim 12, wherein the composition further comprises one or more liposomes, polymers, surfactants, salts, or buffers.

19. The composition of claim 12, wherein the composition further comprises an additional therapeutic agent selected from the group consisting of corticosteroids, bronchodilators, anticholinergics, vasodilators, diuretics, antihypertensive agents, acetazolamide, antibiotics, antivirals, immunosuppressive drugs, and surfactants.

20. The composition of claim 12, wherein the compound is provided in an amount that competitively inhibits inflammation and activates macrophages to protect lung tissue damage or limit lung tissue injury.

21. The composition of claim 12, wherein the compound is provided in an amount that is a TLR4 modulator and upregulates IL-10.

22. The composition of claim 12, wherein the compound is provided in an amount that is a TLR2, TLR4, TLR7 and TLR8 inhibitor and downregulates IL-1β.

23. The composition of claim 12, wherein the compound is a TLR9 inhibitor and down regulates IFN-α.

24. A pharmaceutical composition comprising a compound in an amount that activates the immune response as a vaccine adjuvant, antimicrobial, antibacterial, antiviral or immune stimulator, wherein the compound is selected from:

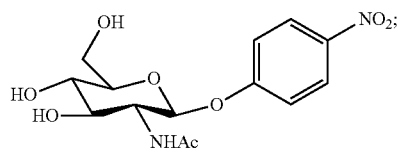

8

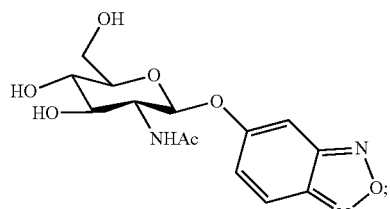

17

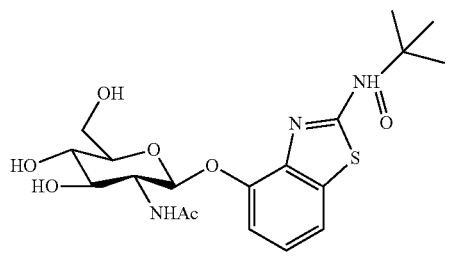

23

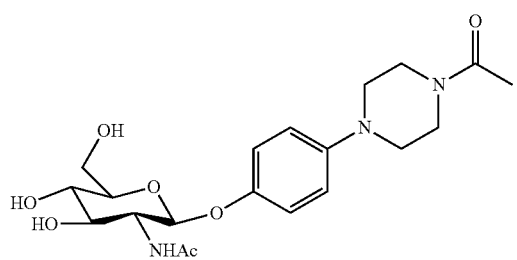

28

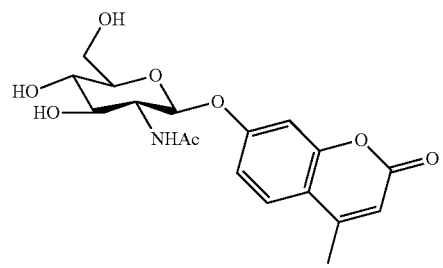

29

-continued

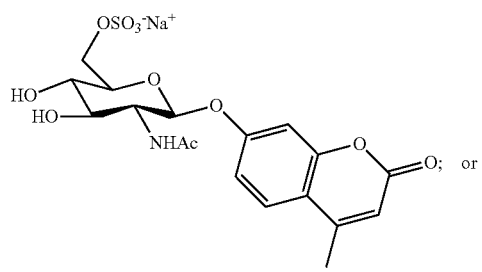

30

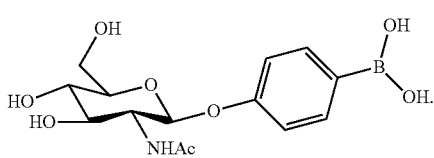

35

25. A composition comprising a compound to treat hyper-inflammation-lung injury, irritable bowel disease, or sepsis, provided at a concentration that inhibits an immune response, wherein the compound is selected from:

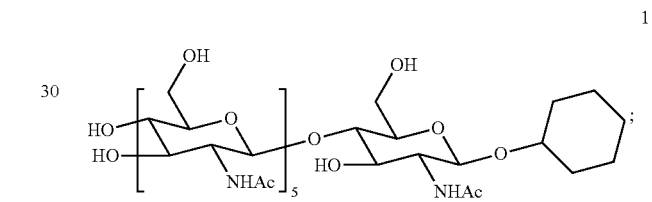

1

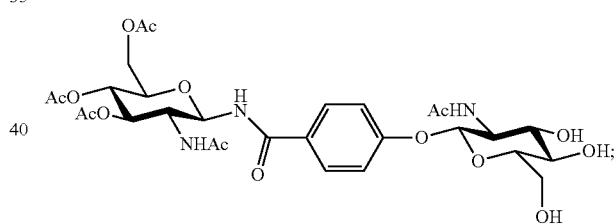

2

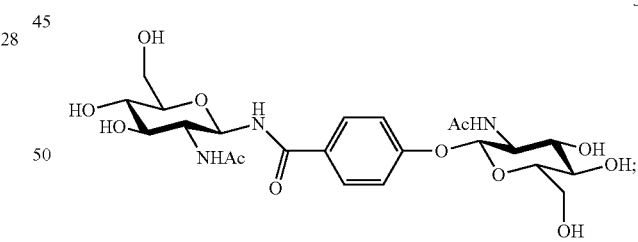

3

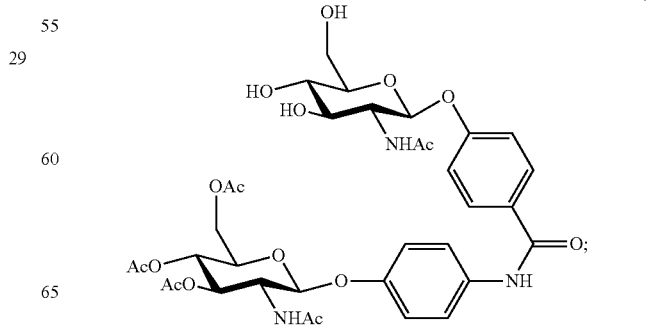

6

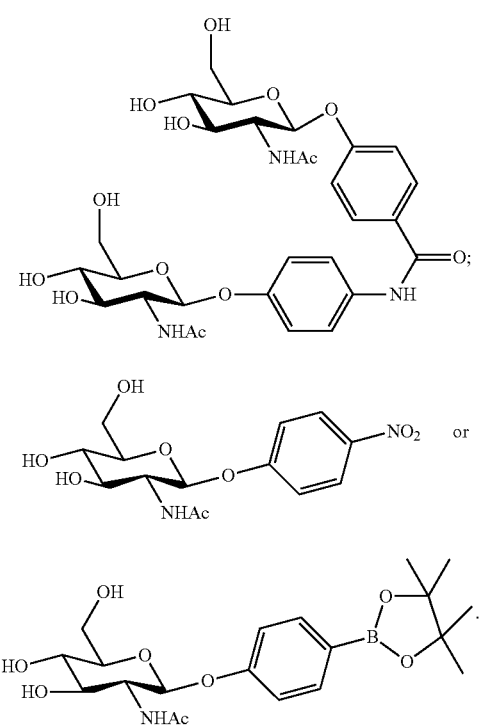

26. A composition that activates the immune response as a vaccine adjuvant, antimicrobial, or immune stimulator, wherein the composition comprise a compound selected from:

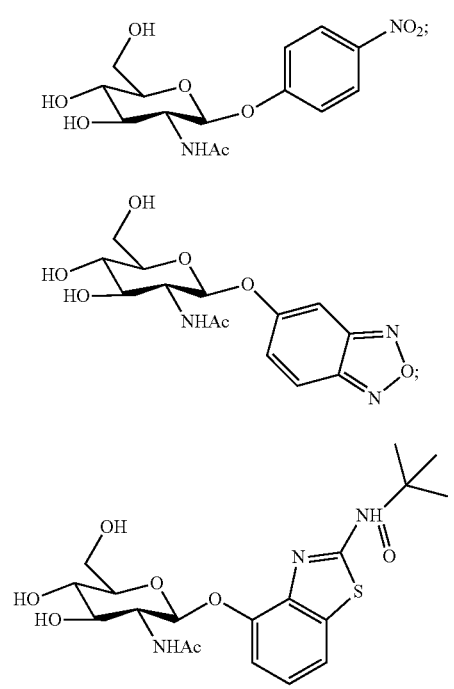

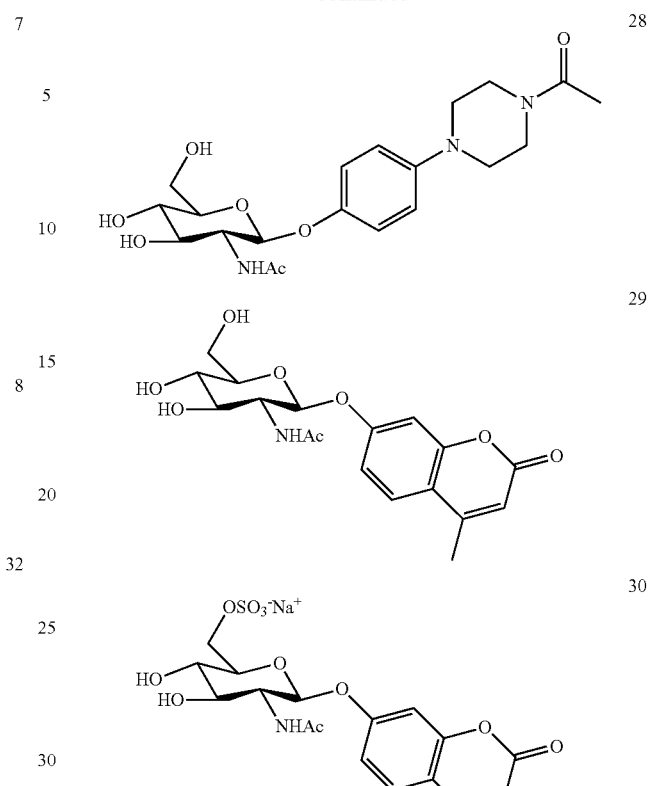

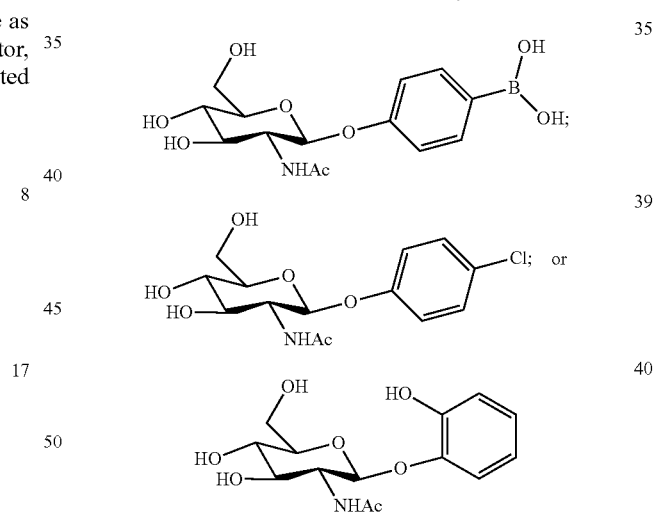

27. A method of treating a subject in need of immunomodulation comprising:

identifying a subject in need of immunomodulation; and providing the subject an effective amount of a composition comprising at least one compound selected from 1, 2, 3, 6, 7, 11, 14, 23, 32, 35, or 38, wherein the composition is formulated to inhibit a TLR4 receptor, a TLR2 receptor, or both the TLR2 and the TLR4 receptor and has the formula and concentration below:

| Compound Number | Structure | Concentration (µM) | % inhibition over control | |
|---|---|---|---|---|
| | | | TLR4 | TLR2 |
| 1 | 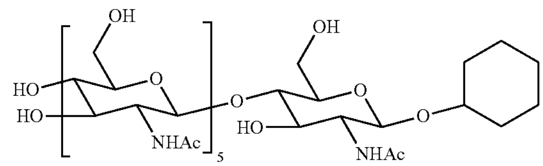 | 1-10 | +++ | |
| | | 75-100 | +++ | |
| 2 | 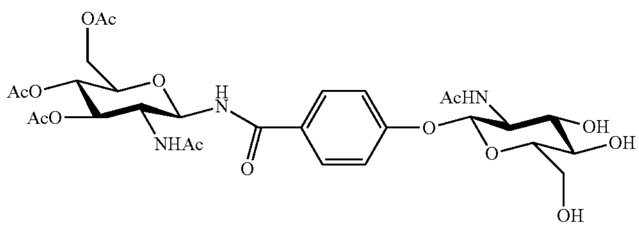 | 1-10 | ++ | + |
| | | 75-100 | +++ | +++ |
| 3 | 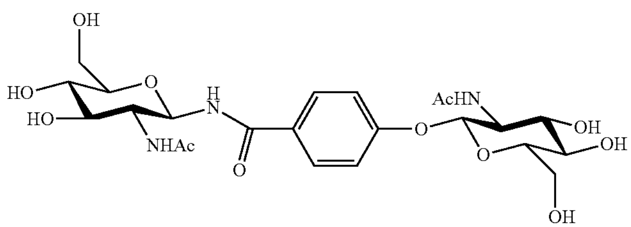 | 1-10 | ++ | ++ |
| | | 75-100 | +++ | +++ |
| 6 | 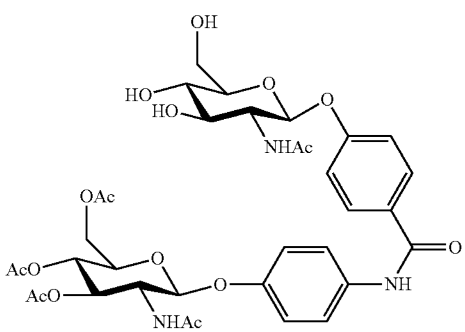 | 1-10 | ++ | |
| | | 75-100 | +++ | |
| 7 | 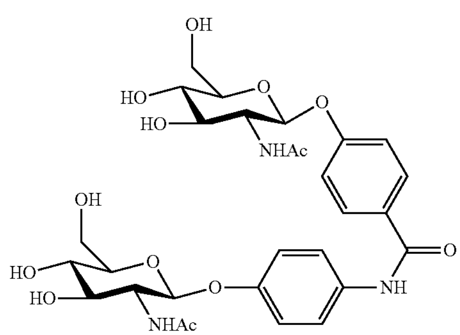 | 1-10 | +++ | ++ |
| | | 75-100 | +++ | +++ |
| 11 | 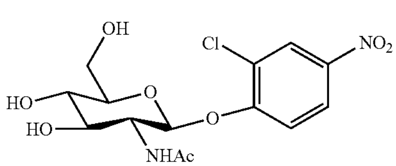 | 1-10 | + | |
| | | 75-100 | + | |

-continued

| Compound Number | Structure | Concentration (μM) | % inhibition over control TLR4 | TLR2 |
|---|---|---|---|---|
| 14 | [structure: GlcNAc-O-phenyl-CN] | 1<br>100 | +++<br>+++ | |
| 23 | [structure: GlcNAc-O-benzothiazole-NH-C(=O)-C(CH3)3] | 1-10<br>75-100 | +<br>+ | |
| 32 | [structure: GlcNAc-O-phenyl-Bpin] | 1-10<br>75-100 | +++<br>+++ | +++<br>+ |
| 35; or | [structure: GlcNAc-O-phenyl-B(OH)2] | 1-10<br>75-100 | +++ | |
| 38 | [structure: GlcNAc-O-phenyl-OCH3] | 1-10<br>75-100 | | ++. |

28. The method of claim 27, wherein the composition is formulated into a pharmaceutical composition comprising one or more pharmaceutically acceptable excipients, buffers, or salts.

29. The method of claim 27, wherein the composition is formulated into a pharmaceutical composition adapted for pulmonary, alveolar, enteral, parenteral, intravenous, topical, or oral administration.

30. The method of claim 27, wherein the composition is formulated into an aerosol, a nebulizer, or an inhaler.

31. The method of claim 27, wherein the composition further comprises one or more liposomes, polymers, surfactants, salts, or buffers.

32. The method of claim 27, wherein the composition further comprises an additional therapeutic agent selected from the group consisting of corticosteroids, bronchodilators, anticholinergics, vasodilators, diuretics, anti-hypertensive agents, acetazolamide, antibiotics, immunosuppressive drugs, and surfactants.

33. The method of claim 27, wherein the compound competitively inhibits inflammation and activates macrophages to protect lung tissue damage or limit lung tissue injury.

34. The method of claim 27, wherein the subject has a pulmonary disorder selected from Acute Respiratory Distress Syndrome (ARDS), Adult Respiratory Distress Syndrome (Adult RDS), hyperoxic lung injury, or Bronchopulmonary dysplasia (BPD), chronic obstructive pulmonary disease (COPD), exacerbated COPD, Cystic Fibrosis, Asthma, severe Asthma, exacerbated Asthma, allergic Asthma, Acute lung injury, Idiopathic pulmonary fibrosis, Airway remodeling, or Bronchiolitis obliterans syndrome.

35. The method of claim 27, wherein the composition is formulated into a pharmaceutical composition adapted for pulmonary, alveolar, enteral, parenteral, intravenous, topical, or oral administration.

36. The method of claim 27, wherein the composition is administered by a nebulizer or an inhaler, the compound is inhaled in an aerosolized form, or the compound is inhaled in an aerosolized form that comprises droplets less than 10 micrometers in diameter, wherein the droplets comprise the compound in a suitable pharmacologically acceptable liquid carrier.

37. The method of claim 27, wherein the subject is a premature infant born at an age of about 24 to about 32 weeks gestation, an infant and the weight of the infant at birth is about 1500 grams or less, an infant and the weight of the infant at birth is about 1000 grams or less, or an infant and the at least one additional agent or therapy is selected from the group consisting of oxygen therapy, ventilator therapy, and a bronchodilator.

38. The method of claim 27, further comprising administering an additional therapeutic agent selected from the group consisting of corticosteroids, bronchodilators, anticholinergics, vasodilators, diuretics, anti-hypertensive agents, acetazolamide, antibiotics, immunosuppressive drugs, surfactants and supplemental oxygen.

39. The method of claim 27, wherein the compound is provided in an amount sufficient to competitively inhibit inflammation and activate an alternate pathway of macrophages activation that protects lung tissue damage or limits lung tissue injury.

40. The method of claim 27, wherein the compound is a TLR4 inhibitor and upregulates IL-10.

41. The method of claim 27, wherein the compound is a TLR7/8/9 inhibitor at low concentration and TLR7/8 activator at high concentration.

42. The method of claim 27, wherein the compound is a TLR6 activator.

43. The method of claim 27, wherein the composition inhibits cancer cell proliferation and induces cancer cell death.

44. The method of claim 27, wherein the composition inhibits angiogenesis.

45. The method of claim 27, wherein the composition is provided in an amount sufficient to competitively inhibit inflammation and angiogenesis and protect from ocular angiogenesis related injury.

46. A method of treating a subject in need of immunomodulation comprising:
identifying a subject in need of immunomodulation; and
providing the subject an effective amount of a composition comprising at least one compound selected from compound 8, 17, 28, 29, 30, or 35, wherein the composition is formulated to inhibit a TLR4 receptor, a TLR2 receptor, or both the TLR2 and the TLR4 receptor, wherein the composition is formulated to inhibit the immune response at a first concentration, and activate the immune response at a second concentration, wherein the compound is formulated into a low or a high dose composition comprising:

| Compound Number | Structure | Concentration (μM) | % inhibition over control TLR4 | % inhibition over control TLR2 | % activation over control TLR4 | % activation over control TLR2 |
|---|---|---|---|---|---|---|
| 8 | (structure: sugar-O-phenyl-NO₂ with NHAc) | 1-10<br>75-100 | +++ | + | ++ | ++ |
| 17 | (structure: sugar-O-benzofurazan with NHAc) | 1-10<br>75-100 | | ++<br>+++ | | ++ |
| 28 | (structure: sugar-O-phenyl-piperazine-acetyl with NHAc) | 1-10<br>75-100 | + | | | ++ |

-continued

| Compound Number | Structure | Concentration (μM) | % inhibition over control TLR4 | % inhibition over control TLR2 | % activation over control TLR4 | % activation over control TLR2 |
|---|---|---|---|---|---|---|
| 29 | (structure: HO, HO, NHAc sugar linked to 4-methylcoumarin with CH2OH) | 1-10 | | | | ++ |
| | | 75-100 | | | + | + |
| 30; or | (structure: OSO3⁻Na⁺ sugar with NHAc linked to 4-methylcoumarin) | 1-10 | | | + | + |
| | | 75-100 | | | | |
| 35 | (structure: NHAc sugar linked via O to phenyl-B(OH)2) | 1-10 | +++ | | | |
| | | 75-100 | | | ++. | |

47. The method of claim 46, wherein the composition is formulated into a pharmaceutical composition comprising one or more pharmaceutically acceptable excipients, buffers, or salts.

48. The method of claim 46, wherein the composition is formulated into a pharmaceutical composition adapted for pulmonary, alveolar, enteral, parenteral, intravenous, topical, or oral administration.

49. The method of claim 46, wherein the composition is formulated into an aerosol, a nebulizer, or an inhaler.

50. The method of claim 46, wherein the composition further comprises one or more liposomes, polymers, surfactants, salts, or buffers.

51. The method of claim 46, wherein the composition further comprises an additional therapeutic agent selected from the group consisting of corticosteroids, bronchodilators, anticholinergics, vasodilators, diuretics, anti-hypertensive agents, acetazolamide, antibiotics, immunosuppressive drugs, and surfactants.

52. The method of claim 46, wherein the compound competitively inhibits inflammation and activates macrophages to protect lung tissue damage or limit lung tissue injury.

53. The method of claim 46, wherein the subject has a pulmonary disorder selected from Acute Respiratory Distress Syndrome (ARDS), Adult Respiratory Distress Syndrome (Adult RDS), hyperoxic lung injury, or Bronchopulmonary dysplasia (BPD), chronic obstructive pulmonary disease (COPD), exacerbated COPD, Cystic Fibrosis, Asthma, severe Asthma, exacerbated Asthma, allergic Asthma, Acute lung injury, Idiopathic pulmonary fibrosis, Airway remodeling, or Bronchiolitis obliterans syndrome.

54. The method of claim 46, wherein the composition is formulated into a pharmaceutical composition adapted for pulmonary, alveolar, enteral, parenteral, intravenous, topical, or oral administration.

55. The method of claim 46, wherein the composition is administered by a nebulizer or an inhaler, the compound is inhaled in an aerosolized form, or the compound is inhaled in an aerosolized form that comprises droplets less than 10 micrometers in diameter, wherein the droplets comprise the compound in a suitable pharmacologically acceptable liquid carrier.

56. The method of claim 46, wherein the subject is a premature infant born at an age of about 24 to about 32 weeks gestation, an infant and the weight of the infant at birth is about 1500 grams or less, an infant and the weight of the infant at birth is about 1000 grams or less, or an infant and the at least one additional agent or therapy is selected from the group consisting of oxygen therapy, ventilator therapy, and a bronchodilator.

57. The method of claim 46, further comprising administering an additional therapeutic agent selected from the group consisting of corticosteroids, bronchodilators, anticholinergics, vasodilators, diuretics, anti-hypertensive agents, acetazolamide, antibiotics, immunosuppressive drugs, surfactants and supplemental oxygen.

58. The method of claim 46, wherein the compound is provided in an amount sufficient to competitively inhibit inflammation and activate an alternate pathway of macrophages activation that protects lung tissue damage or limits lung tissue injury.

59. The method of claim 46, wherein the compound is a TLR4 inhibitor and upregulates IL-10.

60. The method of claim 46, wherein the compound is a TLR7/8/9 inhibitor at low concentration and TLR7/8 activator at high concentration.

61. The method of claim 46, wherein the compound is a TLR6 activator.

62. The method of claim 46, wherein the composition inhibits cancer cell proliferation and induces cancer cell death.

63. The method of claim 46, wherein the composition inhibits angiogenesis.

64. The method of claim 46, wherein the composition is provided in an amount sufficient to competitively inhibit inflammation and angiogenesis and protect from ocular angiogenesis related injury.

* * * * *

UNITED STATES PATENT AND TRADEMARK OFFICE
CERTIFICATE OF CORRECTION

PATENT NO. : 11,364,253 B2
APPLICATION NO. : 16/460211
DATED : June 21, 2022
INVENTOR(S) : Acharya et al.

Page 1 of 1

It is certified that error appears in the above-identified patent and that said Letters Patent is hereby corrected as shown below:

In the Specification

Column 1, Lines 13-14:
Replace "This research is partly funded by NIH/NIAID federal grant 1 R43 AI129164-01 awarded to AyuVis Research." with --None.--

Signed and Sealed this
Eighteenth Day of November, 2025

John A. Squires
*Director of the United States Patent and Trademark Office*